United States Patent
Coffey et al.

(10) Patent No.: US 8,168,659 B2
(45) Date of Patent: May 1, 2012

(54) 1, 5-DIPHENYL-3-BENZYLAMINO-1, 5-DIHYDROPYRROLIDIN-2-ONE AS CB1 RECEPTOR MODULATORS

(75) Inventors: David Scott Coffey, Fishers, IN (US); Jingdan Hu, Carmel, IN (US); Stacy Jo Keding, Zionsville, IN (US); Joseph Herman Krushinski, Jr., Brownsburg, IN (US); John Mehnert Schaus, Zionsville, IN (US); David Edward Tupper, Basingstoke (GB)

(73) Assignee: Eli Lilly and Company, Indianapolis, IN (US)

( * ) Notice: Subject to any disclaimer, the term of this patent is extended or adjusted under 35 U.S.C. 154(b) by 255 days.

(21) Appl. No.: 12/441,570

(22) PCT Filed: Oct. 22, 2007

(86) PCT No.: PCT/US2007/082042
§ 371 (c)(1), (2), (4) Date: Mar. 17, 2009

(87) PCT Pub. No.: WO2008/070306
PCT Pub. Date: Jun. 12, 2008

(65) Prior Publication Data
US 2009/0275618 A1    Nov. 5, 2009

Related U.S. Application Data

(60) Provisional application No. 60/862,540, filed on Oct. 23, 2006.

(51) Int. Cl.
A61K 31/4439    (2006.01)
C07D 401/12    (2006.01)
(52) U.S. Cl. .................................... 514/343; 546/278.4
(58) Field of Classification Search ............... 546/278.4; 514/343
See application file for complete search history.

(56) References Cited

FOREIGN PATENT DOCUMENTS
WO    WO 2005/077911 A    8/2005
WO    WO 2005/080345 A    9/2005
WO    WO 2007/020502 A    2/2007

OTHER PUBLICATIONS

Piomelli, et al., "Review—The endocannabinoid system as a target for therapeutic drugs", *TIPS*—vol. 21—218-224 (2000).
Goya, et al., "Recent advances in cannabinoid receptor agonists and antagonists" *Exp. Opin. Ther. Patents* vol. 10 (10), 1529-1538 (2000).
Xiang, et al., "Pharamacology of Cannabinoid Receptor Agonists and Antagonists". *Annual Report in Medicinal Chemistry—Academic Press*, NY—vol. 34. 199-208.
Francis Barth, "Cannabinoid receptor agonists and antagonists", *Expert Opinion on Therapeutic Patents*—vol. 8(3) 301-313 (1998).
Andreichikov, et al. "Five membered 2,3-dioxo heterocycles, I. Synthesis and structure of 1,5-d", *Zhurnal Organicheskoi Khimii*—22(10) 2208-13 (1986).

*Primary Examiner* — Patricia Morris
(74) *Attorney, Agent, or Firm* — R. Craig Tucker

(57) ABSTRACT

Compounds and pharmaceutical compositions comprising compounds of the Formula

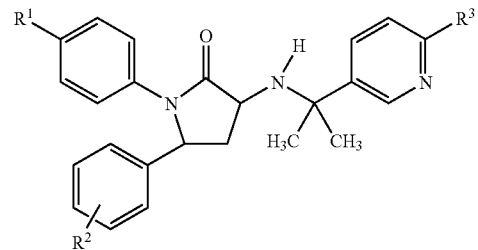

as $CB_1$ receptor inverse agonists useful for reducing body weight in mammals, treating cognitive impairment associated with schizophrenia, and mitigating treatment emergent weight gain observed during treatment with antipsychotics.

3 Claims, No Drawings

1, 5-DIPHENYL-3-BENZYLAMINO-1, 5-DIHYDROPYRROLIDIN-2-ONE AS CB1 RECEPTOR MODULATORS

This U.S. national stage application of International Application PCT/US2007/082042, filed Oct. 22, 2007, claims priority to U.S. provisional application Ser. No. 60/862,540, filed Oct. 23, 2006.

BACKGROUND OF THE INVENTION

The $CB_1$, receptor family is primarily found in the central and peripheral nervous systems and to a lesser extent in several peripheral organs. The $CB_2$ receptor is found primarily in the immune system. The pharmacology and therapeutic potential for cannabinoid receptor ligands has been reviewed (Exp. Opin. Ther. Patents 1998, 8, 301-313; Ann. Rep. Med. Chem., A. Doherty, Ed.; Academic Press, NY 1999, Vol. 34, 199-208; Exp. Opin. Ther. 2000, 10, 1529-1538; Trends in Pharma. Sci. 2000, 21, 218-224). $CB_1$, receptor agonists have been associated with stimulation of feeding, anemetic properties, analgesia, reduction in intraocular pressure in glaucoma, and alleviation of muscle spasms in multiple sclerosis. Conversely, $CB_1$ receptor antagonists have been shown effective for reducing feeding and body weight in animal models of obesity. However, most compounds that modulate $CB_1$ receptor activity have the pharmacological property of inverse agonism which reduces basal $CB_1$ receptor signal transduction as well as the activity of blocking $CB_1$ agonist dependent receptor stimulation.

A number of selective, centrally acting $CB_1$ receptor compounds are currently in development for the treatment of obesity. Nevertheless, there still remains a need for $CB_1$ receptor compounds which have increased in vivo potency which are low molecular weight, and have pharmacokinetic and pharmacodynamic properties that provide therapeutic benefit while minimizing adverse events. See for example WO 2007/020502.

In addition to appentency disorders, $CB_1$ inverse agonists have been shown to further potentiate the activity of antipsychotic agents in assays. Although current antipsychotic therapies are more or less effective at controlling positive symptoms, such therapies are not as effective in treating the negative and cognitive symptoms, rendering many patients incapable of leading normal lives. Convergent evidence suggests drugs that enhance neuronal activation in specific brain areas, hippocampal, striatal, and cortical areas in particular, would be effective in treating both negative and cognitive symptoms. In addition, the weight loss effects of $CB_1$ receptor compounds have been demonstrated in animal models of antipsychotic treatment-induced weight gain and therefore may also be effective in controlling the treatment-emergent weight gain and metabolic syndrome seen with current antipsychotic therapies.

Moreover, $CB_1$ receptor compounds have been shown to reduce alcohol consumption in animal models of alcohol drinking and therefore may be useful in the treatment of substance abuse.

While oral administration is a preferred route of drug delivery, many $CB_1$ receptor compounds suffer from poor oral bioavailability as a consequence of their limited solubility in aqueous media and their metabolic lability. Because of the high lipophilicity of the endogenous cannabinoid ligands and the complementary site to which they bind in the $CB_1$ receptor, known $CB_1$ receptor compounds are also highly lipophilic. This high lipophilicity leads to poor solubility in aqueous media which limits oral absorption and bioavailability. See for example WO 2007/020502.

In addition, compounds which are rapidly metabolized by the liver may undergo metabolic conversion following absorption from the small intestine and prior to reaching the general circulation. During this process, reactive metabolic intermediate (s) may be formed and subsequently may react with other nucleophiles in the body (such as proteins, DNA, RNA, etc.). This could lead to toxicity issues. This so-called "first pass effect" also limits drug bioavailability. See for example WO 2007/020502.

In conclusion, there is a need for $CB_1$ receptor compounds that have good bioavailability, have increased in vivo potency, are highly selective over $CB_2$, are more readily soluble than previous molecules, and do not form reactive metabolites which could subsequently cause toxicity issues. The present invention satisfies this need and provides related advantages as well.

SUMMARY OF THE INVENTION

The present invention provides a compound of Formula (I)

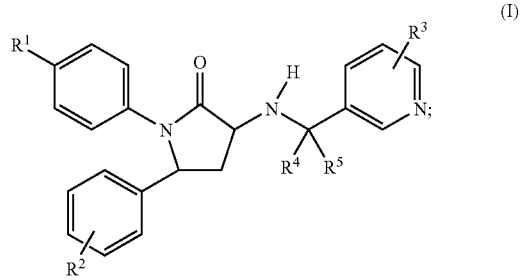

(I)

wherein:
$R^1$ is selected from the group consisting of:
  a) —H,
  b) halo,
  c) —OCF$_3$,
  d) —OCH$_3$,
  e) methyl,
  f) —SO$_2$CH$_3$,
  g) —CF$_3$, and
  h) —CN;
$R^2$ is at least one substituent independently selected from the group consisting of:
  (a) —H,
  (b) halo,
  (c) —CF$_3$,
  (d) —(C$_1$-C$_4$) alkyl,
  (e) cyclopropyl,
  (f) —O-cyclopropyl,
  (g) —SCF$_3$,
  (h) —OCF$_3$
  (i) —OCH$_2$CF$_3$,
  (j) —CN, and
  (k) —O—(C$_1$-C$_3$)alkyl;
$R^3$ is at least one substituent independently selected from selected from the group consisting of:
  a) —H,
  b) —CF$_3$,
  c) —(C$_1$-C$_4$) alkyl,
  d) cyclopropyl,
  e) —OCH$_3$,
  f) halo, and
  g) phenyl;

each $R^4$ and $R^5$ is independently selected from the group consisting of hydrogen, methyl, and ethyl, or both $R^4$ and $R^5$ may be taken together with the carbon to which each is attached to form a cyclopropyl ring; or a pharmaceutically acceptable salt thereof.

A preferred embodiment of the present invention relates to the compound, wherein $R^1$ is —$OCF_3$ or —$OCH_3$.

Another preferred embodiment of the present invention relates to the compound, wherein $R^1$ is selected from the group consisting of hydrogen, halo, methyl, —$CF_3$, and cyano.

In yet another preferred embodiment, the present invention relates to the compound, wherein $R^2$ is selected from the group consisting of hydrogen, halo, —$CF_3$, —$(C_1$-$C_4)$ alkyl, —$SCF_3$, —O-cyclopropyl, —$OCF_3$, and cyano.

Another preferred embodiment of the present invention relates to the compound, wherein $R^3$ is —$CF_3$.

In yet another preferred embodiment, the present invention relates to the compound, wherein $R^3$ is selected from the group consisting of —$CF_3$, cyclopropyl, and halo.

The present invention provides a compound of Formula (Ia)

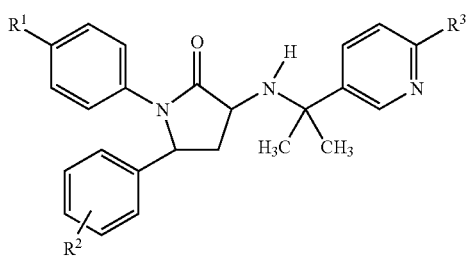

wherein:
$R^1$ is selected from the group consisting of:
  a) —H,
  b) halo,
  c) —$OCF_3$,
  d) —$OCHF_2$,
  e) —$OCH_3$,
  f) methyl,
  g) isopropyl,
  h) cyclopropyl,
  i) —$CF_3$, and
  j) —CN;
$R^2$ is one or two substituents independently selected from the group consisting of:
  a) —O-cyclopropyl,
  b) —$SCF_3$,
  c) —$OCF_3$,
  d) —$OCHF_2$
  e) —$OCH_2CF_3$, and
  f) —$OCF_2CF_2H$;
$R^3$ is selected from:
  a) —$CF_3$, or
  b) -cyclopropyl;
or a pharmaceutically acceptable salt thereof.

The present invention provides a compound of Formula (Ib)

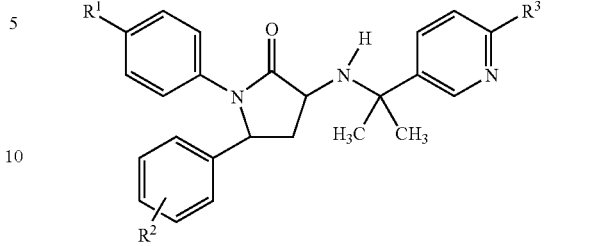

wherein:
$R^1$ is selected from the group consisting of:
  a) —$OCF_3$ and
  b) —$OCHF_2$;
$R^2$ is one or two substituents independently selected from the group consisting of:
  a) —H,
  b) halo,
  c) -fluorosubstituted $(C_1$-$C_3)$ alkyl,
  d) —$(C_1$-$C_4)$ alkyl, and
  e) —CN;
$R^3$ is selected from selected from the group consisting of:
  a) —$CF_3$,
  b) -cyclopropyl, and
  c) halo;
or a pharmaceutically acceptable salt thereof.

In one aspect, the present invention provides a compound of Formula (Ic)

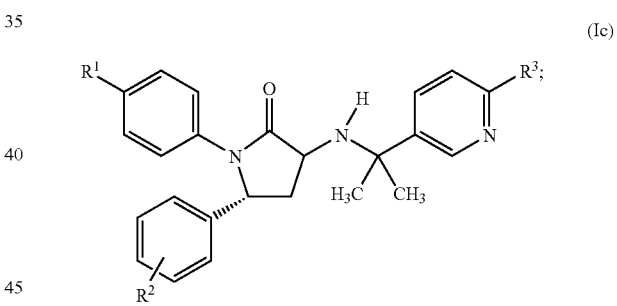

wherein:
$R^1$ is selected from the group consisting of:
  a) —H,
  b) halo,
  c) —$OCF_3$,
  d) —$OCHF_2$,
  e) —$OCH_3$,
  f) methyl,
  g) isopropyl,
  h) cyclopropyl,
  i) —$CF_3$, and
  j) —CN;
$R^2$ is one or two substituents independently selected from the group consisting of:
  a) —O-cyclopropyl,
  b) —$SCF_3$,
  c) —$OCF_3$,
  d) —$OCHF_2$,
  e) —$OCH_2CF_3$, and
  f) —$OCF_2CF_2H$;

$R^3$ is selected from the group consisting of:
a) —H,
b) —$CF_3$,
c) —($C_1$-$C_4$) alkyl,
d) -cyclopropyl,
e) —$OCH_3$,
f) halo, and
g) phenyl;
or a pharmaceutically acceptable salt thereof.

The present invention provides a compound of Formula (Id)

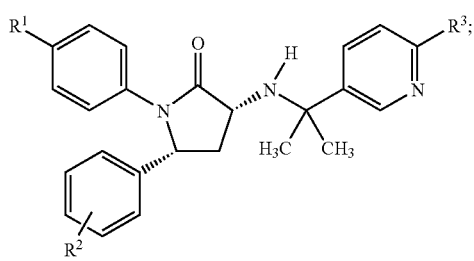

wherein:
$R^1$ is selected from the group consisting of:
a) —H,
b) halo,
c) —$OCF_3$,
d) —$OCHF_2$,
e) —$OCH_3$,
f) methyl,
g) isopropyl,
h) cyclopropyl,
i) —$CF_3$, and
j) —CN;
$R^2$ is one or two substituents independently selected from the group consisting of:
a) —O-cyclopropyl,
b) —$SCF_3$,
c) —$OCF_3$,
d) —$OCHF_2$,
e) —$OCH_2CF_3$, and
f) —$OCF_2CF_2H$;
$R^3$ is selected from the group consisting of:
a) —H,
b) —$CF_3$,
c) —($C_1$-$C_4$) alkyl,
d) -cyclopropyl,
e) —$OCH_3$,
f) halo, and
g) phenyl;
or a pharmaceutically acceptable salt thereof.

The present invention provides a compound of Formula (Ie)

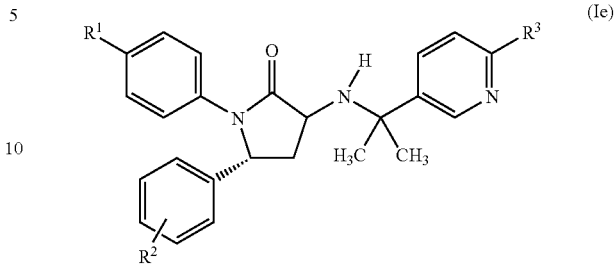

wherein:
$R^1$ is selected from the group consisting of:
a) —$OCF_3$ and
b) —$OCHF_2$;
$R^2$ is one or two substituents independently selected from the group consisting of:
a) —H,
b) halo,
c) -fluorosubstituted ($C_1$-$C_3$) alkyl,
d) —($C_1$-$C_4$) alkyl, and
e) —CN;
$R^3$ is selected from the group consisting of:
a) —H,
b) —$CF_3$,
c) —($C_1$-$C_4$) alkyl,
d) -cyclopropyl,
e) —$OCH_3$,
f) halo, and
g) phenyl;
or a pharmaceutically acceptable salt thereof.

The present invention provides a compound of Formula (If)

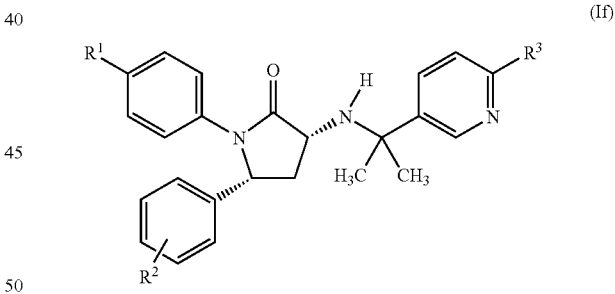

wherein:
$R^1$ is selected from the group consisting of:
a) —$OCF_3$ and
b) —$OCHF_2$;
$R^2$ is one or two substituents independently selected from the group consisting of:
a) —H,
b) halo,
c) -fluorosubstituted ($C_1$-$C_3$) alkyl,
d) —($C_1$-$C_4$) alkyl, and
e) —CN;
$R^3$ is selected from the group consisting of:
a) —H,
b) —$CF_3$,
c) —($C_1$-$C_4$) alkyl,
d) -cyclopropyl, e) —OCH$_3$,
f) halo, and
g) phenyl;

or a pharmaceutically acceptable salt thereof.

The present invention provides an intermediate of Formula (XIVc)

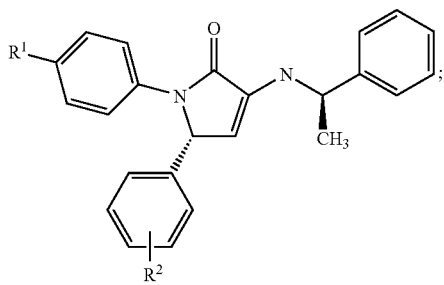

(XIVc)

wherein:
R$^1$ is selected from the group consisting of:
a) H,
b) halo,
c) —OCF$_3$,
d) —OCH$_3$,
e) methyl,
f) —SO$_2$CH$_3$,
g) —CF$_3$, and
h) —CN;

R$^2$ is one or two substituents independently selected from the group consisting of:
a) H,
b) halo,
c) —CF$_3$,
d) —(C$_1$-C$_4$) alkyl,
e) cyclopropyl,
f) —O-cyclopropyl,
g) —SCF$_3$,
h) —OCF$_3$,
i) —OCH$_2$CF$_3$,
j) —CN, and
k) —O—(C$_1$-C$_3$)alkyl.

The present invention provides a an intermediate of Formula (XIVd)

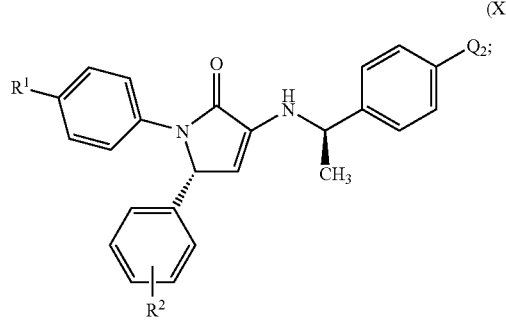

(XIVd)

wherein:
R$^1$ is selected from the group consisting of:
a) —H,
b) halo,
c) —OCF$_3$,
d) —OCHF$_2$,
e) —OCH$_3$,
f) methyl,
g) isopropyl,
h) cyclopropyl,
i) —CF$_3$, and
j) —CN;

R$^2$ is one or two substituents selected from the group consisting of:
a) —O-cyclopropyl,
b) —SCF$_3$,
c) —OCF$_3$,
d) —OCHF$_2$,
e) —OCH$_2$CF$_3$, and
f) —OCF$_2$CF$_2$H;

Q$_2$ is selected from the group consisting of:
a) —H,
b) halo, and
c) —O(C$_1$-C$_3$) alkyl.

The present invention provides an intermediate of Formula (XIVe)

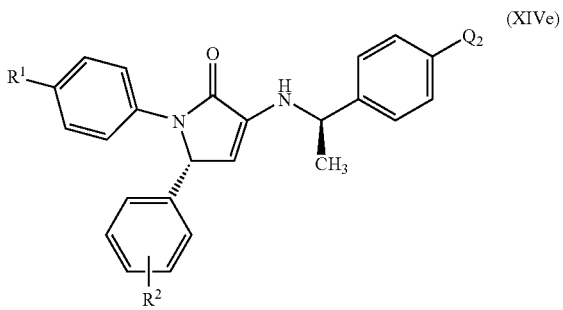

(XIVe)

wherein:
R$^1$ is selected from the group consisting of:
a) —OCF$_3$ and
b) —OCHF$_2$;

R$^2$ is one or two substituents independently selected from the group consisting of:
a) —H,
b) halo,
c) -fluorosubstituted (C$_1$-C$_3$) alkyl,
d) —(C$_1$-C$_4$) alkyl, and
e) —CN;

Q$_2$ is selected from the group consisting of:
a) —H,
b) halo, and
c) —O(C$_1$-C$_3$) alkyl.

The present invention provides a compound selected the group consisting of Examples 1-61.

In another embodiment, the present invention provides an intermediate of formula

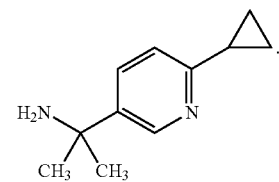

The present invention provides a pharmaceutical composition comprising a compound according to any one of Formulas (I) to (If), or a pharmaceutically acceptable salt thereof, and a pharmaceutically acceptable carrier, diluent, or excipient.

An embodiment of present invention provides the pharmaceutical composition, wherein the compound of Formula (Id) or (If), or a pharmaceutically acceptable salt thereof, is present in optical purity greater than 90% ee.

An embodiment of present invention provides the pharmaceutical composition, wherein the compound of Formulas (Id) or (If), or a pharmaceutically acceptable salt thereof, is present in optical purity greater than 95% ee.

The present invention provides a compound according to any one of Formula (I) to (If), or a pharmaceutically acceptable salt thereof, for use therapy.

The present invention provides a compound according to any one of Formulas (I) to (If), or a pharmaceutically acceptable salt thereof, for use in the treatment of a disorder selected from: an eating disorder associated with excessive food intake, obesity, schizophrenia, cognitive impairment associated with schizophrenia, substance abuse or alcohol dependence, smoking cessation and treatment emergent weight gain observed during treatment with an atypical antipsychotic.

The present invention provides a compound according to any one of Formulas (I) to (If), or a pharmaceutically acceptable salt thereof, for use in simultaneous, separate, or sequential combination with an antipsychotic agent in the treatment of a disorder selected from: weight gain, obesity, schizophrenia, cognitive impairment associated with schizophrenia, substance abuse or alcohol dependence, smoking cessation and treatment emergent weight gain observed during treatment with an atypical antipsychotic.

The present invention provides the use of a compound according to any one of Formulas (I) to (If), or a pharmaceutically acceptable salt thereof, in the manufacture of a medicament for the treatment of a disorder selected from: an eating disorder associated with excessive food intake, obesity, schizophrenia, cognitive impairment associated with schizophrenia, substance abuse or alcohol dependence, smoking cessation and treatment emergent weight gain observed during treatment with an atypical antipsychotic.

The present invention provides the use of a compound according to any one of Formulas (I) to (If), or a pharmaceutically acceptable salt thereof, in the manufacture of a medicament for use in combination therapy for the treatment of a disorder selected from: weight gain, obesity, schizophrenia, cognitive impairment associated with schizophrenia, substance abuse or alcohol dependence, smoking cessation and treatment emergent weight gain observed during treatment with an atypical antipsychotic, wherein said medicament is to be administered in simultaneous, separate or sequential combination with an antipsychotic agent.

The present invention provides a method of treating a condition, wherein the condition is obesity, schizophrenia, cognitive impairment associated with schizophrenia, substance abuse or alcohol dependence, smoking cessation, treatment emergent weight gain observed during smoking cessation, in a mammal comprising administering to the mammal an effective amount of a compound, according to any one of Formulas (I) to (If), or a pharmaceutically acceptable salt thereof, in simultaneous, separate, or sequential combination with an antipsychotic agent.

An embodiment of the invention provides the method, wherein the condition is an eating disorder associated with excessive food intake.

In yet another embodiment, the present invention provides the method, wherein the condition is obesity.

In yet another embodiment, the present invention provides the method, wherein the condition is schizophrenia.

In yet another embodiment, the present invention provides the method, wherein the condition is cognitive impairment associated with schizophrenia.

An embodiment of the present invention provides the method, wherein the condition is substance abuse or alcohol dependence.

Another embodiment of the invention provides the method, wherein the condition is smoking cessation.

In yet another embodiment, the present invention provides the method, wherein the condition is treatment emergent weight gain observed during smoking cessation.

The present invention provides a method of treating a condition, wherein the condition is schizophrenia, weight gain, obesity, cognitive impairment associated with schizophrenia, substance abuse or alcohol dependence, smoking cessation, treatment emergent weight gain observed during treatment with an atypical antipsychotic, in a mammal comprising administering to the mammal an effective amount of a compound, according to any one of Formulas (I) to (If), or a pharmaceutically acceptable salt thereof.

An embodiment of the present invention provides the method, wherein the condition is schizophrenia.

In yet another embodiment, the present invention provides the method, wherein the condition is weight gain.

In yet another embodiment, the present invention provides the method, wherein the condition is obesity.

In yet another embodiment, the present invention provides the method, wherein the condition is cognitive impairment associated with schizophrenia.

In yet another embodiment, the present invention provides the method, wherein the condition is substance abuse or alcohol dependence.

An embodiment of the present invention provides the method, wherein the condition is smoking cessation.

In yet another embodiment, the present invention provides the method, wherein the condition is treatment emergent weight gain observed during treatment with an atypical antipsychotic.

The present invention provides a method of treating a condition in a mammal which is treatable by blockade of $CB_1$ receptors via an inverse agonism mechanism, the method comprising administering to a patient an effective amount of a compound according to any one of Formula (I) or (Ia), or a pharmaceutically acceptable salt thereof.

The present invention provides a method of treating a condition in a mammal which is treatable by blockade of $CB_1$ receptors via an inverse agonism mechanism in simultaneous, separate or sequential combination with an antipsychotic agent, the method comprising administering to a patient an effective amount of a compound according to any one of Formula (I) or (Ia), or a pharmaceutically acceptable salt thereof.

Compounds of Formulas (I), (Ia), (Ib), (Ic) and (Ie) may contain one or more asymmetric centers and can thus occur as diastereomeric mixtures, racemic mixtures, single enantiomers, and individual diastereomers. All such isomeric forms of the compounds of Formulas (I), (Ia), (Ib), (Ic) and (Ie) are contemplated as aspects of the present invention.

While compounds of Formulas (I), (Ia), (Ib), (Ic) and (Ie) in their racemic form are useful agents, it is generally preferable to administer compounds of Formulas (I), (Ia), (Ib), (Ic) and (Ie) in which one of the enantiomeric forms has been enriched. A preferred aspect of this invention provides compounds of Formulas (Id), or (If) that are substantially pure enantiomers. As such, each of the following specific classes of compounds of Formulas (I), (Ia), (Ib), (Ic), (Id), (Ie) and (If) are contemplated as aspects of the present invention:

(a) Those where enantiomeric purities are greater than 80% enantiomeric excess;
(b) Those where enantiomeric purities are greater than 90% enantiomeric excess;
(c) Those where enantiomeric purities are greater than 95% enantiomeric excess; and
(d) Those where enantiomeric purities are greater than 99% enantiomeric excess.

These enantiomerically pure compounds may be prepared by purification of the desired enantiomer of a compound of Formula (I), (Ia), (Ib), (Ic) and (Ie) from a mixture of enantiomers of this compound. The desired enantiomer of a compound of Formula (I), (Ia), (Ib), (Ic) and (Ie) may also be prepared by synthesis according to the following general schemes by using precursors that are substantially enantiomerically pure. Those skilled in the art will recognize that either resolution of final compounds or of intermediates will provide compounds of Formula (I), (Ia), (Ib), (Ic) and (Ie) in substantially enantiomerically pure form, to yield for example, compounds of Formulas (Id), or (If) and will employ the method which is most convenient.

It will be further recognized that a substantially pure diastereomer may be isolated from a mixture of diastereomers using methods known in the art. Methods for purification of diastereomers include the use of chromatography and crystallization. A mixture of enantiomers may be separated into the individual substantially pure enantiomers by the process known as resolution. Enantiomers may be resolved through the use of chromatography using a chiral stationary phase. Suitable chiral solid phases include polysaccharide-based stationary phases such as Chiralpak AD and Chiracel OJ (sold by Chiral Technologies, Inc.). Additionally, enantiomers of basic compounds may be resolved by conversion to a mixture of diastereomeric salts by treatment with a chiral acid. The desired diastereomeric salt is isolated by, for example, crystallization. The substantially enantiomerically pure basic compound may be isolated by treatment with base. Examples of chiral acids include (−)-tartaric acid, (+)-tartaric acid, (−)-mandelic acid, (+)-mandelic acid, (−)-ditoluoyltartaric acid and (+)-ditoluoyltartaric acid. Enantiomers of acidic compounds may be resolved in an analogous manner using a substantially enantiomerically pure base. Examples of such bases include R-alpha-methylbenzylamine, S-alpha-methylbenzylamine, and brucine. Another method for the resolution of a racemic mixture involves reaction with a substantially enantiomerically pure chiral reagent (referred to here as a chiral auxiliary) to form a covalent bond. This reaction results in a mixture of diastereomers, which is purified according to methods known in the art. All, or a portion, of the chiral auxiliary may then be cleaved from the molecule to generate a compound which is substantially enantiomerically pure. In some cases, the asymmetric center introduced by the chiral auxiliary may be retained in the final product.

One of ordinary skill in the art will recognize that certain disclosed intermediate compounds may exist with different points of attachment of hydrogen, and is thus considered tautomeric. The individual tautomers as well as mixtures thereof are contemplated as an aspect of the present invention. Each of the forms of the tautomer may exist, interconvert, and undergo the tautomerization under the conditions specified.

Compounds of Formulas (I), (Ia), (Ib), (Ic), (Id), (Ie) and (If) are selective for the $CB_1$ receptor in preference to the $CB_2$ receptor. There is evidence suggesting that these $CB_1$ receptor ligands act as inverse agonists.

Compounds of Formulas (I), (Ia), (Ib), (Ic), (Id), (Ie) and (If) are modulators of the $CB_1$ receptor, and as such are useful for prevention and treatment of conditions associated with the $CB_1$ receptor. Such conditions include, for example, memory deficits, cognitive disorders, negative symptoms of schizophrenia, anxiety disorders, depression, stress, Parkinson's disease, substance use disorders (particularly to opiates, alcohol, and nicotine), obesity, metabolic disorders, and eating disorders associated with excessive food intake. See DSM-IV-TR., *Diagnostic and Statistical Manual of Mental Disorders. Revised*, 4$^{th}$ Ed., Text Revision (2000). See also DSM-IV, *Diagnostic and Statistical Manual of Mental Disorders* 4$^{th}$ Ed., (1994). The DSM-IV and DSM-IV-TR were prepared by the Task Force on Nomenclature and Statistics of the American Psychiatric Association, and provides descriptions of diagnostic categories. The skilled artisan will recognize that there are alternative nomenclatures, nosologies, and classification systems for pathologic psychological conditions and that these systems evolve with medical scientific progress.

The compounds of Formulas (I), (Ia), (Ib), (Ic), (Id), (Ie) and (If) can also be used to ameliorate weight gain, whether or not the associated weight gain subject can be classified as clinically obese.

An effective amount of the compounds of Formulas (I), (Ia), (Ib), (Ic), (Id), (Ie) and (If) may be administered to a patient in need of such treatment or prophylaxis in order to practice the present methods of therapy. The need for a prophylactic administration according to the methods of the present invention is determined via the use of well-known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment. The magnitude of prophylactic or therapeutic dose of a compound of Formula (I), (Ia), (Ib), (Ic), (Id), (Ie) or (If) will, of course, vary with the nature of the severity of the condition to be treated and with the particular compound of Formula (I), (Ia), (Ib), (Ic), (Id), (Ie) or (If) and its route of administration.

The dose may be administered in a single daily dose or the total daily dosage may be administered in divided doses of two, three or four times daily. Furthermore, based on the properties of the individual compound selected for administration and/or the characteristics of the dosage form (i.e., modified release), the dose may be administered less frequently, e.g., weekly, twice weekly, monthly, etc. The unit dosage may be correspondingly larger for the less frequent administration. When administered via, transdermal routes, or through a continual intravenous solution, the dosage administration will, of course, be continuous rather than intermittent throughout the dosage regimen.

DETAILED DESCRIPTION

As used above and throughout the description of the invention, the following terms, unless otherwise indicated, shall be defined as follows:

As used herein the term "$(C_1-C_4)$alkyl" refers to a straight or branched, monovalent, saturated aliphatic chain of 1 to 4 carbon atoms and includes, but is not limited to, methyl, ethyl, propyl, isopropyl, butyl, isobutyl, and t-butyl. The term "$(C_1-C_4)$ alkyl" includes within its definition the term "$(C_1-C_3)$ alkyl".

As used herein, the term "Halo" refers to a chlorine, bromine, or fluorine atom, unless otherwise specified herein.

As used herein, the term "Ph" refers to a phenyl group.

As used herein the term "—O—($C_1$-$C_3$)alkyl" refers to a straight or branched, monovalent, saturated aliphatic chain having from 1 to 3 carbon atoms attached to an oxygen atom. Typical "—O—($C_1$-$C_3$)alkyl" groups include methoxy, ethoxy, propoxy, isopropoxy, and the like.

As used herein, the term "fluorosubstituted ($C_1$-$C_3$) alkyl" refers to a straight or branched, monovalent, saturated aliphatic chain having from 1 to 3 carbon atoms wherein 1 to 7 hydrogen(s) have been replaced with a fluorine atom and includes, but is not limited to (—$CF_3$), (—$CF_2CF_3$), (—$CHF_2$), (—$CF_2CH_3$) and (—$CH_2CF_3$).

"Agonist(s)" shall refer to those compounds which stimulate the functional response of a receptor.

"Neutral antagonist(s)" shall refer to those compounds which do not alter the basal activity of a receptor but block the functional activity of agonists and inverse agonists by returning the functional response to that of the basal state.

"Inverse agonist(s)" shall refer to those compounds which possess negative intrinsic activity by reversing the constitutive activity of the receptor. Inverse agonists act to inhibit or reverse the activity of agonists.

"Antagonist(s)" shall refer to those compounds which are neutral antagonists.

"Obesity" refers to the condition of having a high amount of body fat. A person is considered obese if he or she has a body mass index (BMI) of 30 kg/$m^2$ or greater. A person with BMI=27-30 is generally considered overweight. Conventionally, those persons with normal weight have a BMI of 19.9 to 25.9. The obesity may be due to any cause, whether genetic or environmental. Examples of disorders that may result in obesity or be the cause of obesity include overeating, decreased physical activity and pathological conditions showing reduced metabolic activity.

"Pharmaceutically acceptable salts" and "salts" refer to the relatively non-toxic, inorganic and organic acid addition salts, and base addition salts, of compounds of the present invention. See, for example S. M. Berge, et al., "Pharmaceutical Salts," J. Pharm. Sci., 66, 1-19 (1977).

"Pharmaceutical composition" and "composition" are intended to encompass a product comprising the active ingredient, preferably present in pharmaceutically effective amounts, and the inert ingredient(s) (pharmaceutically acceptable excipients) that make up the carrier, as well as any product which results, directly or indirectly from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula (I), (Ia), (Ib), (Ic), (Id), (Ie) or (If) and any pharmaceutically acceptable excipients.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity (e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis).

"Solvate" means a physical association of a compound with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

"Treating," as used herein, unless otherwise indicated, means reversing, alleviating, inhibiting the progress of, or preventing the disorder or condition to which such term applies, or one or more symptoms of such disorder or condition. The term "treatment" as used herein, unless otherwise indicated, refers to the act of treating as "treating" is defined immediately above.

"TFA," as used herein, unless otherwise indicated, means trifluoroacetic acid.

"p.o.," as used herein, unless otherwise indicated, means orally.

"THF," as used herein, unless otherwise indicated, means tetrahydrofuran.

"DMAP," as used herein, unless otherwise indicated, means 4-(N,N-dimethylamino)pyridine.

"MTBE," as used herein, unless otherwise indicated, means methyl tert-butyl ether.

"TBTU," as used herein, unless otherwise indicated, means O-(Benzotriazol-1-yl)-N,N,N',N'-tetramethyluronium tetrafluoroborate.

"EDCI," as used herein, unless otherwise indicated, means 1-(3-dimethylaminopropyl)-3-ethylcarbodiimide hydrochloride.

"DMF," as used herein, unless otherwise indicated, means dimethylformamide.

"psig," as used herein, unless otherwise indicated, means pounds per square inch gauge.

"NaOtBu" and "KOtBu," as used herein, unless otherwise indicated, means sodium tert-butoxide and potassium tert-butoxide respectively.

"TosCl," as used herein, unless otherwise indicated, means p-toluenesulfonylchloride.

"MeOH," as used herein, unless otherwise indicated, means methanol.

"EtOAc," as used herein, unless otherwise indicated, means ethyl acetate.

"HOBt," as used herein, unless otherwise indicated, means N-Hydroxybenzotriazole.

"DMEA," as used herein, unless otherwise indicated, means N,N dimethylethanolamine.

"Ret.," as used herein, unless otherwise indicated, mean retention.

"DMSO," as used herein, unless otherwise indicated, means dimethyl sulfoxide.

"Hex," as used herein, unless otherwise indicated, means hexanes.

For the therapeutic utility taught herein, the salt of the claimed compounds must be pharmaceutically acceptable. For further details on pharmaceutically acceptable salts, see *Journal of Pharmaceutical Science*, 66, 1 (1977).

It will be understood that the compounds of the present invention described below may exist as distinct crystal forms prepared by crystallization under controlled conditions.

Scheme I

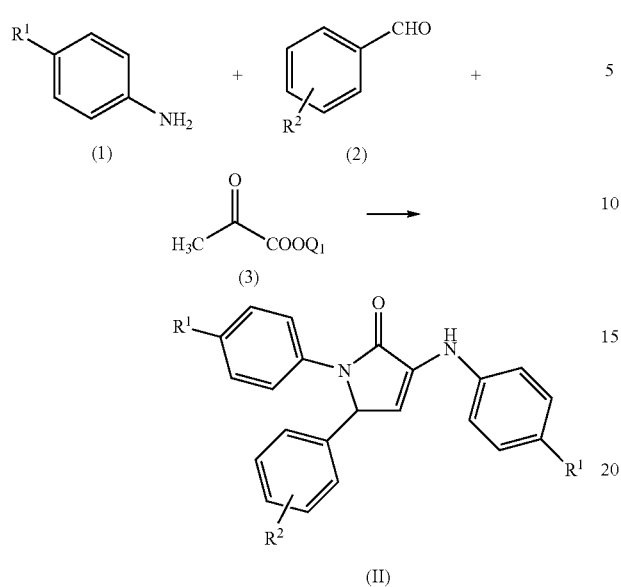

In Scheme I, a compound of Formula (II) may be prepared by the method described by Andreichikov and coworkers (Andreichikov, et al. Zhurnal Organicheskoi Khimii 22(10), 2208-13 (1986)), in which a mixture of an amine of Formula (1) and an aldehyde of Formula (2) is treated with an ester of pyruvic acid (3), where $Q_1$ is a $C_{1-3}$ alkyl group, in a suitable solvent. Suitable solvents include glacial acetic acid, dioxane, tetrahydrofuran, benzene, and toluene. This reaction may also be performed in the presence of solvent mixtures containing these solvents. Suitable esters of pyruvic acid include ethyl pyruvate. The reaction may proceed at temperatures between room temperature and the boiling point of the solvent or solvent mixture. In some cases, the product (II) may precipitate during the course of the reaction or upon addition of a solvent in which the product is not highly soluble. These solvents include diethylether, heptane, MTBE, acetone, water, toluene, and pentane and mixtures thereof. If a precipitate is formed, the compound of Formula (II) may be isolated by filtration and vacuum drying. Alternatively, the compound may be isolated by concentration of the reaction and chromatography of the residue or by aqueous workup and concentration and chromatography of the organic extracts.

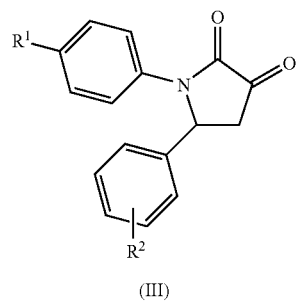

In Scheme II, a compound of formula (III) may be prepared by treatment of a compound of formula (II) with water, optionally in the presence of an acid or a mixture of acids. This reaction may also optionally be performed in the presence of additional solvents such as tetrahydrofuran, methanol, acetic acid and toluene. Suitable acids include hydrochloric acid, sulfuric acid, acetic acid and trifluoroacetic acid. Suitable reaction conditions include treatment of a compound of Formula (II) with acetic acid, water and trifluoroacetic acid at about ambient temperature for around 1 hour or treatment of a compound of Formula (II) in a mixture of acetic acid and hydrochloric acid at around room temperature for about 22 hours. Also, the compound of Formula (III) can be prepared by hydrolysis with acetic acid at around 80° C. for about 8 hours. Also, the compound of Formula (III) can be prepared by hydrolysis with mixing with Dowex 50-2X200 ion exchange resin in aqueous methanol at about ambient temperature for around 5 hours. Also, the compound of Formula (III) can be prepared by hydrolysis with trifluoroacetic acid in a biphasic mixture with the solvents toluene and water for around 1 hour at about room temperature. It is often advantageous to perform this reaction in the presence of at least one equivalent of 2,5-dimethoxytetrahydrofuran. Once the compound of formula (III) has formed, it can be isolated by pouring into water and extraction with organic solvents such as dichloromethane, diethylether, ethyl acetate, isopropyl acetate and toluene. The extract may be dried over a desiccant such as sodium sulfate and concentrated to provide the product as a crude mixture. It is often advantageous to use this compound directly in the next reaction rather than to purify it further. In some cases, pouring the reaction onto ice/water allows precipitation and isolation of the compound of formula (III) through filtration.

Scheme II

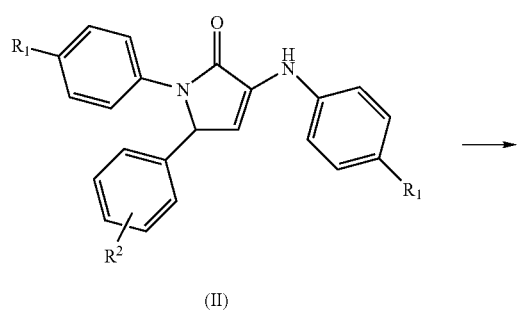

Scheme III

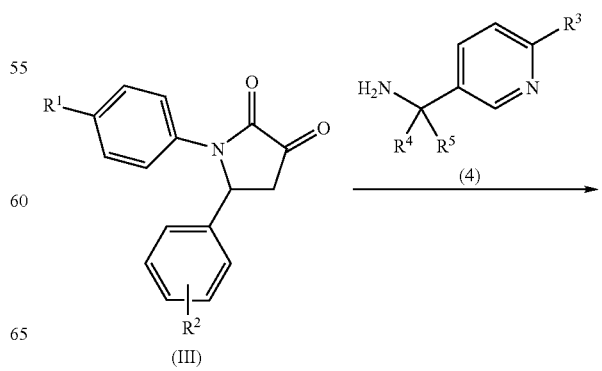

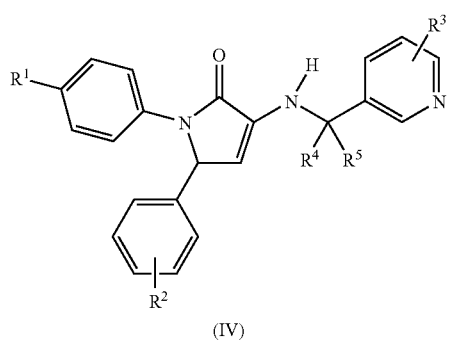

(IV)

In Scheme III, a compound of Formula (IV) may be prepared by treatment of a solution of a compound of Formula (III) with a compound of Formula (4). Suitable solvents include dichloromethane, tetrahydrofuran, or toluene and may be performed at temperatures ranging from room temperature to around 80° C. This reaction may be promoted by removal of water as it is formed by treatment with a dehydrating agent such as $Na_2SO_4$ or $MgSO_4$ or 4A molecular sieves or azeotropic removal of water. This reaction may also be performed in the presence of a catalyst such as p-toluenesulfonic acid, acetic acid or other acidic compound. The compound of Formula (IV) can be isolated, if desired, by methods known in the art such as by precipitation with a solvent such as isopropyl acetate or by silica gel chromatography.

Scheme IV

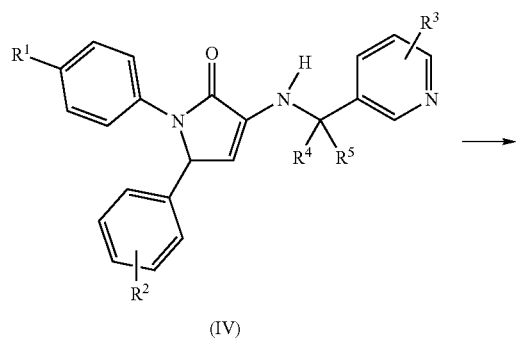

(IV)

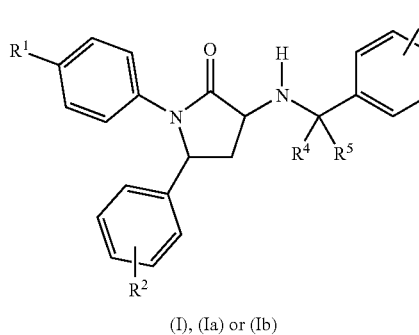

(I), (Ia) or (Ib)

In Scheme IV, a compound of formula (I), (Ia), and (Ib) may be formed by treatment of a compound of formula (IV) under suitable reducing conditions. Suitable reducing conditions include treatment with $NaCNBH_3$ in the presence of acetic acid with an optional solvent such as dichloromethane at around room temperature for about 30 minutes to about 12 hours, treatment with $NaBH_4$ in an alcoholic solvent, treatment with $Na(OAc)_3BH$ in the presence of trifluoroacetic acid in a suitable solvent such a toluene at room temperature for about 23 hours, and hydrogenation conditions in which a solution of compound of formula (IV) is treated with a suitable metal catalyst under a hydrogen atmosphere. Suitable solvents include methanol, ethanol, ethyl acetate and tetrahydrofuran. Suitable metal catalysts include palladium on carbon and platinum oxide. Compound of Formula (IV) is dissolved in ethanol and methanol mixture and subjected to a hydrogen atmosphere in the presence of a suitable catalyst such as Pd/C at around room temperature for about 24 hours. The reaction is filtered and concentrated in vacuo to obtain the compound of Formula (I), (Ia), or (Ib). The compound of Formula (I), (Ia), or (Ib) can be isolated by means such as aqueous workup or precipitation of the product. Further purification may be performed by use of such techniques as SCX-2 ion exchange chromatography, silica gel chromatography, SuperCritical Fluid Chromatography, reverse phase chromatography and crystallization. Purification may also be performed by treatment of mixtures containing a compound of Formula (I), (Ia), or (Ib) with an acid to provide the salt of compound of Formula (I), (Ia), or (Ib) which may then be purified by crystallization to provide the purified salt of the compound of Formula (I), (Ia), or (Ib). Preferred salts include those formed by addition with hydrochloric acid and p-toluenesulfonic acid.

In the synthesis of a compound of Formula (I), (Ia), or (Ib), either of the intermediates of Formula (III) or Formula (IV) may be used directly in subsequent reactions without purification of the crude intermediates.

Single enantiomers of compounds of Formula (I), (Ia), or (Ib) are generally preferred over the corresponding racemates. These enantiomers may be prepared by resolution of a compound of Formula (I), (Ia), or (Ib) using techniques such as preparative chromatography employing a chiral stationary phase. The enantiomers may also be prepared by resolution which comprises formation of a salt of the racemic mixture with an optically active acid and purification of the desired diastereomeric salt. The desired diastereomeric salt may be purified by crystallization. Alternatively, any of the intermediates of formula (II), (III), or (IV) may be resolved to provide substantially a single enantiomer which may then be converted using the methods described above to provide a compound of Formula (I), (Ia), or (Ib) in its enantiomerically purified form such as compounds of Formula (Ic), (Id), (Ie) or (If). The intermediates of formula (II), (III), or (IV) may be prepared by resolution of compounds of the corresponding racemic compound using techniques such as preparative chromatography employing a chiral stationary phase.

Scheme V

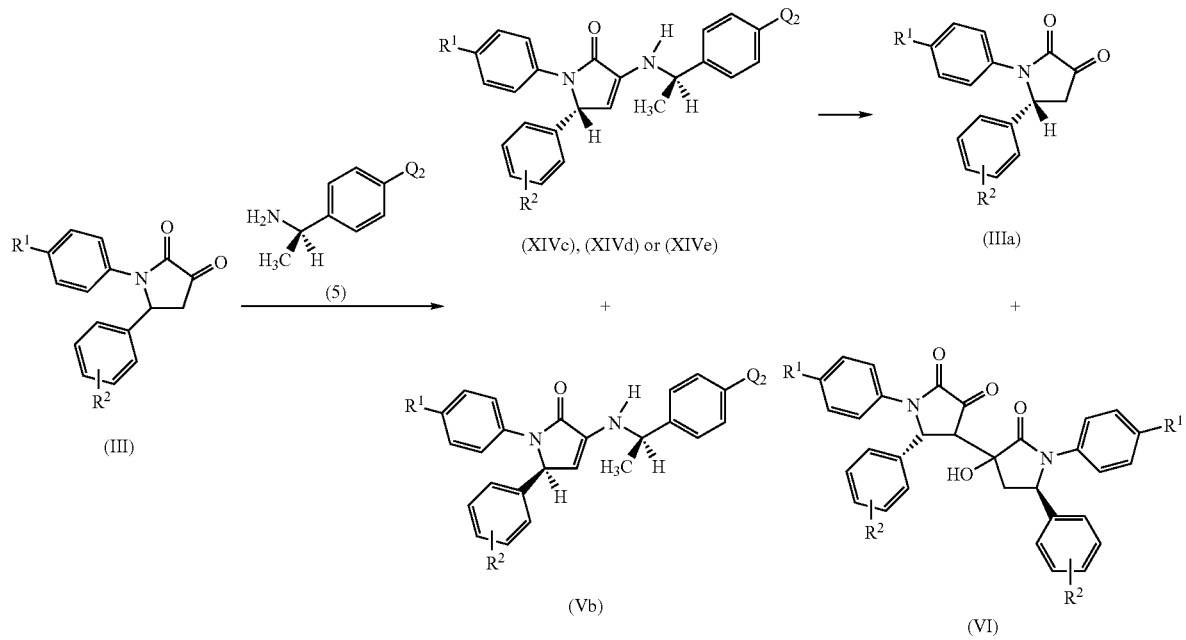

An alternative and often preferred method for the preparation of purified enantiomers of compounds of formula (III) is outlined in Scheme V. A racemic compound of formula (III) is reacted with a compound of formula (5), in which $Q_2$ is hydrogen, halogen, or a $(C_1-C_3)$alkoxy group, to form a diastereomeric mixture of compounds of formula (XIVc), (XIVd), or (XIVe) and (Vb). Preferred compounds of formula (5) include R-alpha-methylbenzylamine, S-alpha-methylbenzylamine, R-4-chloro-alpha-methylbenzylamine, S-4-chloro-alpha-methylbenzylamine, R-4-methoxy-alpha-methylbenzylamine, and S-4-methoxy-alpha-methylbenzylamine. This condensation may be performed by combining a compound of Formula (III) and compound (5) an inert solvent such as methylene chloride, tetrahydrofuran, or toluene and optionally heating from room temperature to around 80° C. to until the completion of the reaction. This reaction may be promoted by removal of water as it is formed by treatment with a dehydrating agent such as $Na_2SO_4$ or $MgSO_4$ or 4A molecular sieves or azeotropic removal of water. This reaction may also be performed in the presence of a catalyst such as p-toluenesulfonic acid, acetic acid or other acidic compound. The diastereomers of formula (XIVc), (XIVd), or (XIVe) and (Vb) are then separated using techniques such as silica gel chromatography or crystallization from inert solvents such as isopropanol or mixtures of solvents. The desired diastereomer (designated (XIVc), (XIVd), or (XIVe) in Scheme V) is then hydrolyzed to form the purified enantiomer of formula (IIIa). Suitable hydrolysis conditions include treating a solution of the desired diastereomer in acetic acid with aqueous hydrochloric acid. In some instances, the crude (IIIa) may contain substantial amounts of the dimer of formula (VI).

In Scheme V, the racemic compound of formula (III) may be crude product resulting from the process outlined in Scheme II. In addition, the purified enantiomer of formula (IIIa) may be used directly from the hydrolysis reaction, without further purification, in the process outlined in Scheme III.

In Scheme V, the (R)-enantiomer of compound (5) was chosen to exemplify the process. One skilled in the art will recognize that the (S)-enantiomer of compound (5) may also be used in this process. The choice of whether to use the (R)- or (S)-enantiomer may be made depending on which will yield the desired diastereomer that is more readily isolated.

Scheme VI

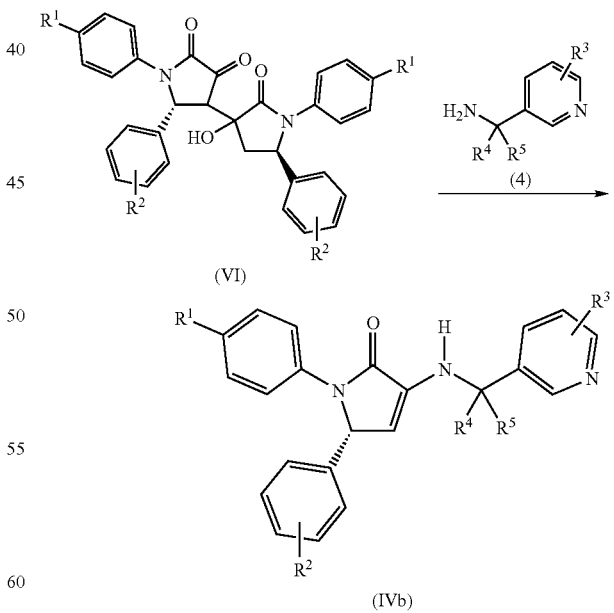

In Scheme VI, the compound of formula (IVb) may also be formed by treatment of compound of formula (VI) with compound (4) under the same conditions as described for the reaction of compound (IIIa) with (4). In some cases, heating the reaction in a microwave reactor may be advantageous.

Scheme VII

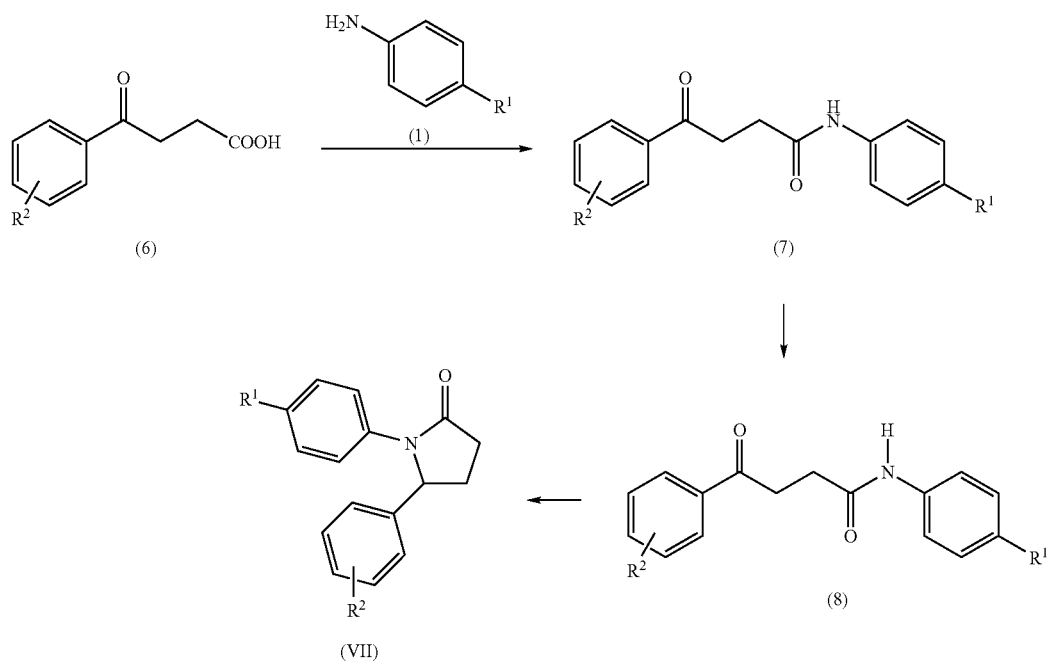

In Scheme VII, the compound of Formula (VII) may be prepared as described. A compound of structure (6) is coupled to a compound (1) with agents such as TBTU, EDCI or HOBt and an optional catalysts such as DMAP and an appropriate solvent such as dimethylformamide and triethylamine at around room temperature for about 18 hours. Aqueous acidic work-up, concentration and silica gel chromatography or trituration with solvents such as hexane gives the compound of structure (7). The ketone group of compound (7) is converted to the alcohol group of compound (8) with a reducing agent such as sodium borohydride in solvent mixtures such as water, methanol, ethanol, and DME at about room temperature to 0° C. An alternative and often preferred method, compound (7) may undergo chiral reduction to form compound (8) in which one of the enantiomers is enriched. Methods for chiral reduction of ketones are known in the art (see, for instance, Singh, Synthesis 605 (1992); Wallbaum and Martens, Tetrahedron: Asymmetry 3, 1475 (1992); Matteoli, Beghetto, and Scrivanti, J. Molecular Catalysis A: Chemical 140, 131 (1999); Heiser, Broger, and Crameri, Tetrahedron: Asymmetry 2, 51 (1991)). Suitable chiral reducing conditions include treatment under hydrogenation conditions using a chiral catalyst such as (R-Tol-Binap)RuCl$_2$, and reduction mediated by a chiral oxazaborolidine catalyst (also known as CBS reduction; Corey, Bakshi, and Shibata, J. Amer. Chem. Soc. 109, 5551 (1987)). The reaction is performed in a Parr Vessel under hydrogenation atmosphere in a suitable solvent such as methanol at around 80° C. for about 24 hours. Compound (8) is isolated by acidic aqueous work up and concentration. In the following step, the lactam compound of Formula (VII) is produced via cyclization of compound (8) in a solvent such as tetrahydrofuran and with the addition of tosyl chloride by treatment drop-wise with a solution of a base such as KOt-Bu at about −40° C. The reaction is warmed to room temperature and aqueous ammonium chloride is added and concentrated. The residue is dissolved in an appropriate solvent such as ethyl acetate, washed with brine and dried. Work-up and purification by methods known in the art such as silica gel chromatography affords compound of Formula (VII). Alternatively, compound (8) is subjected to cyclization conditions such as n-butyllithium at around −78° C. in an appropriate solvent such as tetrahydrofuran for about 30 minutes. p-Toluenesulfonyl chloride is added. After approximately an additional 18 hours and by methods known in the art such as chiral chromatography, compound (VII) is isolated.

Scheme VIII

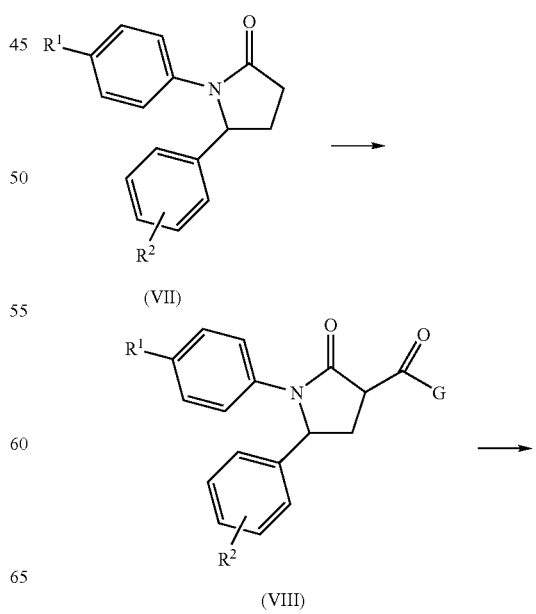

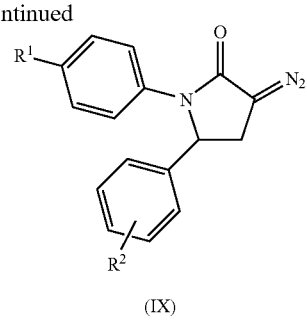

(IX)

In Scheme VIII, a compound of Formula (VIII), in which G is hydrogen, $C_{1-4}$ alkyl, $C_{1-4}$ haloalkyl, or phenyl, optionally substituted with $C_{1-3}$ alkyl or halo, is prepared by treatment of a compound of Formula (VII) with a compound of formula $GCOOQ_3$, in which $Q_3$ is $C_{1-4}$ alkyl, under basic conditions such as sodium hydride, in a solvent such as toluene at approximately room temperature followed by silica gel chromatography. Compound (IX) is then formed by treatment of compound (VIII) with a compound of Formula $Q_4SO_2N_3$, in which $Q_4$ is phenyl, optionally substituted with $C_{1-3}$ alkyl, $C_{1-3}$ alkoxy, halo, or NHCO $C_{1-3}$ alkyl. The reaction may be performed in a solvent such as acetonitrile and stirred for approximately 30 minutes. Work-up and purification by methods known in the art such as silica gel chromatography affords compound of Formula (IX).

Scheme IX

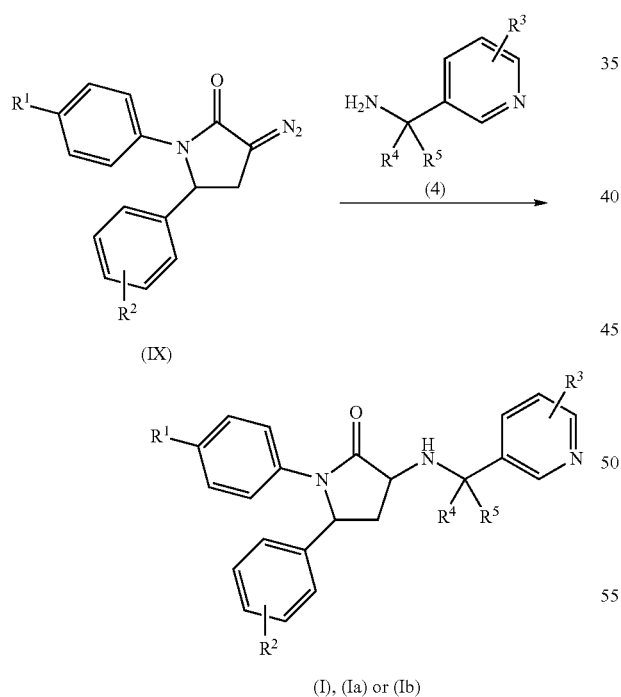

In Scheme IX, a compound of Formula (I), (Ia), and (Ib) may be prepared by treatment of a solution of a diazolactam of Formula (IX) with compound (4) in an inert solvent with a suitable catalyst. Suitable catalysts include $Rh_2(OAc)_4$. The compound of Formula (IX) and compound (4) are dissolved in toluene under a nitrogen atmosphere and heated to around 45° C. The catalyst, $Rh_2(OAc)_4$, is added and the reaction is continued to be stirred at around 45° C. for about 30 minutes. Concentrating the reaction mixture provides the crude compound of Formula (I), (Ia) or (Ib) which is isolated by methods known in the art such as SCX-2 ion exchange, silica gel chromatography, and SuperCritical Fluid Chromatography.

Scheme X

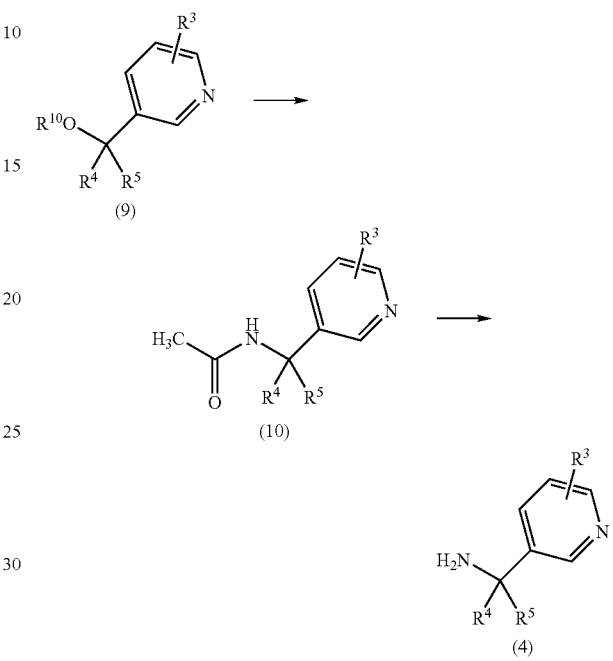

In Scheme X, the compound (4) is prepared by treatment of a compound (9), in which $R^{10}$ is hydrogen, $C_{1-4}$ alkyl, or $C_{1-4}$ alkyl-C(O)—, with acetonitrile in the presence of acid to provide a compound of Formula (10). Suitable acids include sulfuric acid and trifluoroacetic acid. After combining the above, the reaction is heated to around 45° C. for about 28 hours. The reaction is cooled to about 0° C. and quenched with aqueous sodium hydroxide. Compound (10) is isolated by precipitation with ethanol and water. Compound (10) is heated in a solution of aqueous hydrochloric acid to around 90° C. for about 20 hours. The reaction is quenched with ice and sodium hydroxide. The compound (4) is isolated after several washes with methyl t-butyl ether and tetrahydrofuran and precipitation with heptane.

Scheme XI

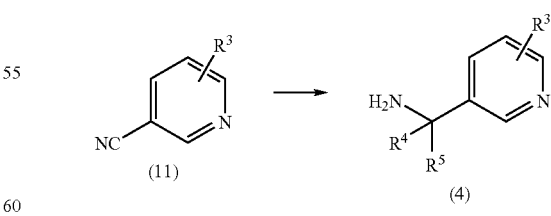

In Scheme XI, compound (4) is prepared from a compound of formula (11). Anhydrous cerium (III) chloride is prepared by heating cerium (III) chloride heptahydrate to about 140° C. under vacuum and then suspended in an appropriate solvent such as tetrahydrofuran at room temperature. The reaction is cooled to −78° C. and methyllithium is added dropwise.

Compound (11) in tetrahydrofuran is added dropwise to the solution. The reaction is stirred at around −78° C. for about 30 minutes to 4 hours and warmed around 20° C. After about 1 to 20 hours, the reaction is cooled to around −78° C. and aqueous ammonia is added. The reaction is warmed around 20° C. for about 1 hour. The compound (4) is isolated by methods known in the art such as silica gel chromatography.

PREPARATIONS AND EXAMPLES

Conditions for HPLC Methods referred to throughout the Preparations and Examples:
Method 1
LC column: Waters XTerra C18 2.1×50 mm 3.5 uM
Gradient: 5-100% acetonitrile/methanol (50/50) w/0.2% ammonium formate in 7.0 minutes then held at 100% for 1.0 minute Column temperature: 50° C.+/−10° C.
autosampler temperature: ambient
Flow rate: 1.0 mL/minute
Signal detected at 214 nM wavelength.
Method 2
LC column: Waters XTerra C18 2.1×50 mm 3.5 uM
Gradient: 5-100% acetonitrile/methanol (50/50) w/0.2% ammonium formate in 3.5 minutes then held at 100% for 0.5 minutes Column temperature: 50° C.+/−10° C.
autosampler temperature: ambient
Flow rate: 1.0 mL/minutes
Signal detected at 214 nM wavelength.
Method 3
LC Column: Phenomenex Gemini $C_{18}$ 2.0×50 mm 3.0 μM
Gradient: 5-100% ACN ACN w/0.1% Formic Acid in 7.0 min. then held at 100% for 1.0 min.
Column Temp: 50° C.+/−10° C.
autosampler temperature: ambient
Flow Rate: 1.0 mL/min.
Signal detected at 300 nM wavelength.
Method 4
LC column: Zorbax RX-$C_{18}$ 4.6×250 mm 5 μm
Gradient: 50-90% acetonitrile w/0.03 M Phosphate Buffer (Phosphate Buffer=5.52 g $NaH_2PO_4$ and 1.4 mL $H_3PO_4$ in 2 L Milli-Q $H_2O$) in 15 minutes. Column temperature: 40° C.
autosampler temperature: ambient
Flow rate: 1.5 mL/minute
Signal detected at 260 nM wavelength.
Chiral HPLC conditions:
Method A
column: 0.46×15 cm Chiralpak AD-H
Isocratic: anhydrous ethanol with 0.2% dimethylethylamine
Flow rate: 0.6 mL/minutes
UV 250 nM
Method B
column: 0.46×15 cm Chiralpak AD-H
Isocratic: 100% MeOH with 0.2% dimethylethylamine
Flow rate: 0.6 mL/minutes
UV 260 nM Preparation 1

(±)-5-(3-Trifluoromethoxy-phenyl)-1-(4-fluoro-phenyl)-3-(4-fluoro-phenylamino)-1,5-dihydro-pyrrol-2-one

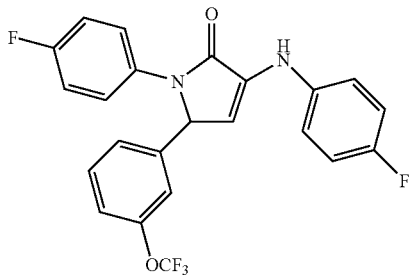

Stir 3-(trifluoromethoxy)benzaldehyde (15.0 g, 78.6 mmol), 4-fluoroaniline (22.4 mL, 236 mmol) and ethyl pyruvate (8.65 mL, 78.6 mmol) in glacial acetic acid (60 mL) at ambient temperature for 72 hours. Filter the precipitate and wash with a 3:1 heptane/MTBE mixture. Dry under vacuum to afford the titled compound (20.9 g, 60%) as an off-white powder: MS (m/z): 445 (M−1).

Prepare the following Compounds essentially by the method of Preparation 1.

TABLE 1

| Prep. N° | Compound and Name | Yield, Physical data, and Comments |
|---|---|---|
| 2 | (±)-5-[3-(2,2,2-Trifluoro-ethoxy)-phenyl]-1-(4-trifluoromethyl-phenyl)-3-(4-trifluoromethyl-phenylamino)-1,5-dihydro-pyrrol-2-one | Yield 81%<br>MS (m/z): 559 (M − 1)<br>Dilute reaction with 3:1 heptane/MTBE to aid in filtering. Isolate additional product from filtrate by trituration with DCM-MeOH. Isolate additional product from second filtrate by silica gel chromatography. |

TABLE 1-continued

| Prep. N° | Compound and Name | Yield, Physical data, and Comments |
|---|---|---|
| 3 | 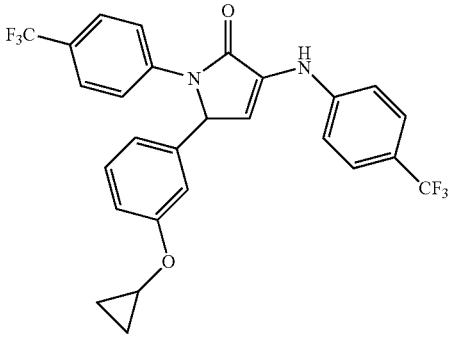<br>(±)-5-(3-Cyclopropoxyphenyl)-1-(4-trifluoromethylphenyl)-3-(4-trifluoromethylphenylamino)-1,5-dihydropyrrol-2-one | Yield 57%<br>LCMS: 5.68 min. (Method 3); ESMS m/z 519.2 (M + 1), 517.2 (M − 1). |
| 4 | 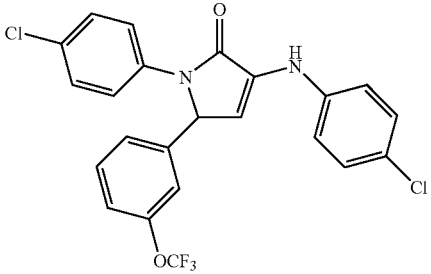<br>(±)-5-(3-Trifluoromethoxy-phenyl)-1-(4-chloro-phenyl)-3-(4-chloro-phenylamino)-1,5-dihydro-pyrrol-2-one | Yield 50%<br>MS (m/z): 479 (M + 1)<br>No dilution prior to filtering. Wash Filter cake with heptane. |
| 5 | 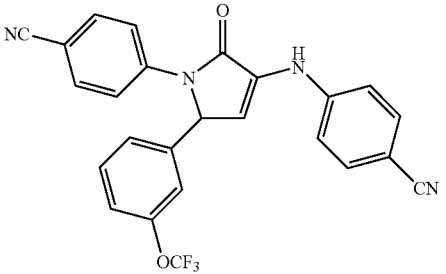<br>(±)-5-(3-Trifluoromethyl-phenyl)-1-(4-cyano-phenyl)-3-(4-cyano-phenylamino)-1,5-dihydro-pyrrol-2-one | Yield 87%<br>MS (m/z): 461 (M + 1)<br>Dilute with 3:1 heptane/MTBE to aid in filtering. |
| 6 | 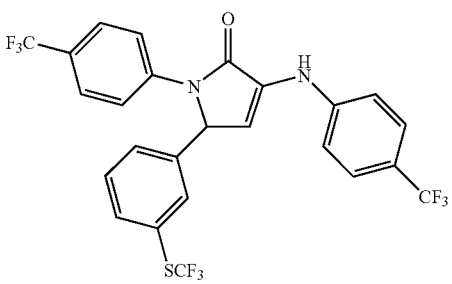<br>(±)-5-(3-Trifluoromethylsulfanyl-phenyl)-1-(4-trifluoromethyl-phenyl)-3-(4-trifluoromethyl-phenylamino)-1,5-dihydro-pyrrol-2-one | Yield 73%<br>MS (m/z): 561 (M − 1) |

TABLE 1-continued

| Prep. N° | Compound and Name | Yield, Physical data, and Comments |
|---|---|---|
| 7 | 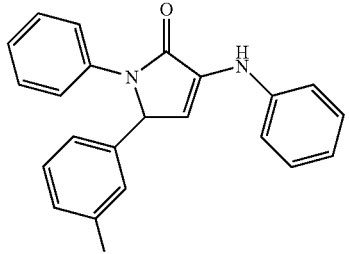<br>(±)-1-Phenyl-3-(phenylamino)-5-(3-trifluoromethoxy-phenyl)-1,5-dihydro-pyrrol-2-one | Yield 38%<br>MS (m/z): 411 (M + 1)<br>Isolate additional product from filtrate by silica gel chromatography and crystallization. |
| 8 | 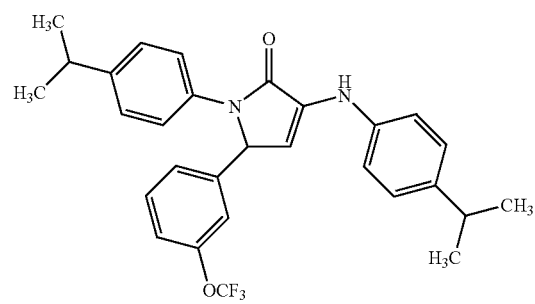<br>(±)-5-(3-Trifluoromethoxy-phenyl)-1-(4-isopropyl-phenyl)-3-(4-isopropyl-phenylamino)-1,5-dihydro-pyrrol-2-one | Yield 14%<br>MS (m/z): 495 (M + 1) |
| 9 | 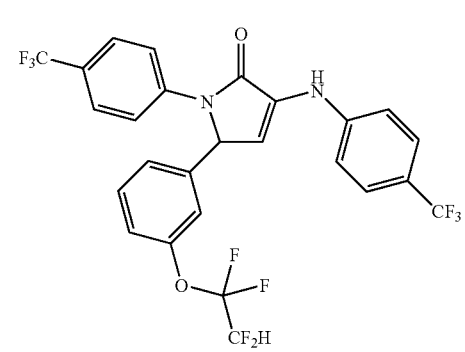<br>(±)-5-[3-(1,1,2,2-Tetrafluoro-ethoxy)-phenyl]-1-(4-trifluoromethyl-phenyl)-3-(4-trifluoromethyl-phenylamino)-1,5-dihydro-pyrrol-2-one | Yield 29%<br>MS (m/z): 577 (M − 1)<br>Reaction time: 18 hours |
| 10 | 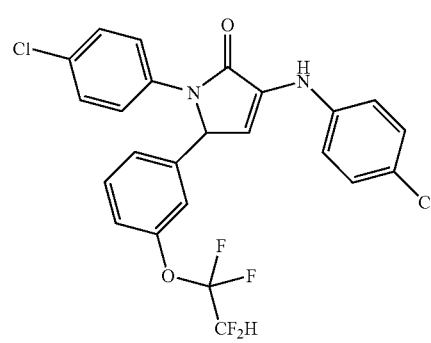<br>(±)-5-[3-(1,1,2,2-Tetrafluoro-ethoxy)-phenyl]-1-(4-chloro-phenyl)-3-(4-chloro-phenylamino)-1,5-dihydro-pyrrol-2-one | Yield 33%<br>MS (m/z): 509 (M − 1)<br>Reaction time: 5 days |

TABLE 1-continued

| Prep. N° | Compound and Name | Yield, Physical data, and Comments |
|---|---|---|
| 11 | 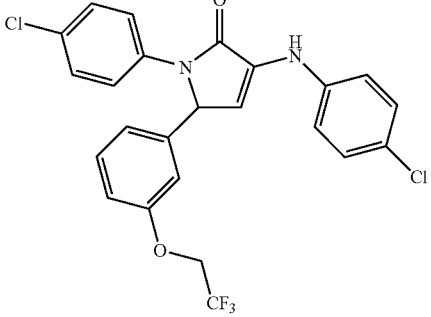<br>(±)-5-[3-(2,2,2-Trifluoro-ethoxy)-phenyl]-1-(4-chloro-phenyl)-3-(4-chloro-phenylamino)-1,5-dihydro-pyrrol-2-one | Yield 62%<br>MS (m/z): 491 (M − 1) |
| 12 | 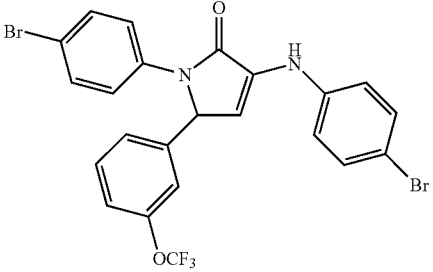<br>(±)-5-(3-Trifluoromethoxy-phenyl)-1-(4-bromo-phenyl)-3-(4-bromo-phenylamino)-1,5-dihydro-pyrrol-2-one | Yield 56%<br>MS (m/z): 564.8 (M − 1)<br>Wash precipitate with 2:1 heptane/MTBE. |
| 13 | 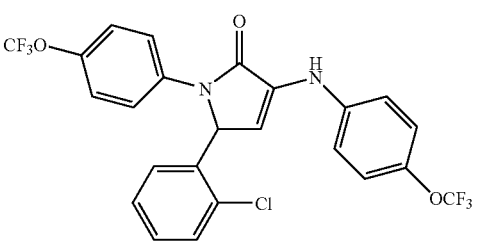<br>(±)-5-(2-Chloro-phenyl)-1-(4-trifluoromethoxy-phenyl)-3-(4-trifluoromethoxy-phenylamino)-1,5-dihydro-pyrrol-2-one | Yield 64.9%<br>MS (m/z): 527 (M − 1)<br>Wash precipitate with hexanes. |
| 14 | 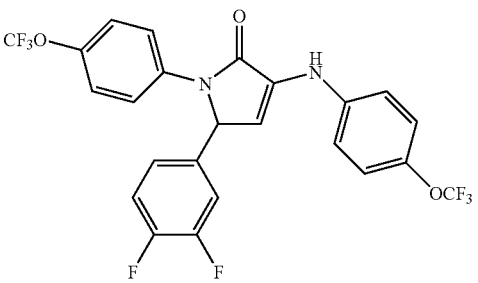<br>(±)-5-(3,4-Difluoro-phenyl)-1-(4-trifluoromethoxy-phenyl)-3-(4-trifluoromethoxy-phenylamino)-1,5-dihydro-pyrrol-2-one | Yield 62.7%<br>MS (m/z): 529 (M − 1)<br>Wash precipitate with hexanes. |

TABLE 1-continued

| Prep. N° | Compound and Name | Yield, Physical data, and Comments |
|---|---|---|
| 15 | 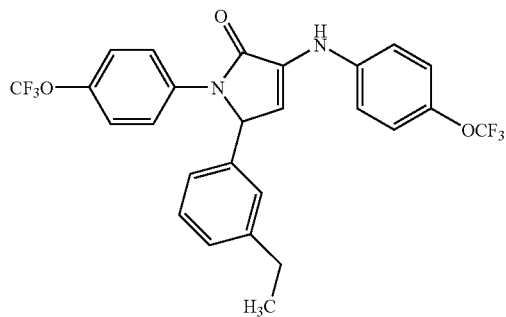<br>(±)-5-(3-Ethyl-phenyl)-1-(4-trifluoromethoxy-phenyl)-3-(4-trifluoromethoxy-phenylamino)-1,5-dihydro-pyrrol-2-one | Yield 50%<br>MS (m/z)⁻: 520 (M − 1) |
| 16 | 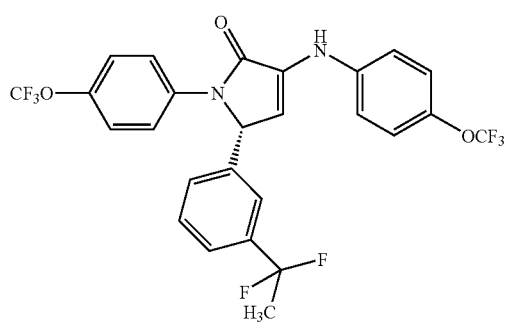<br>(±)-5-[3-(1,1-Difluoro-ethyl)-phenyl]-1-(4-trifluoromethoxy-phenyl)-3-(4-trifluoromethoxy-phenylamino)-1,5-dihydro-pyrrol-2-one | Yield 89%<br>MS (m/z)⁻: 557 (M − 1) |
| 16A | 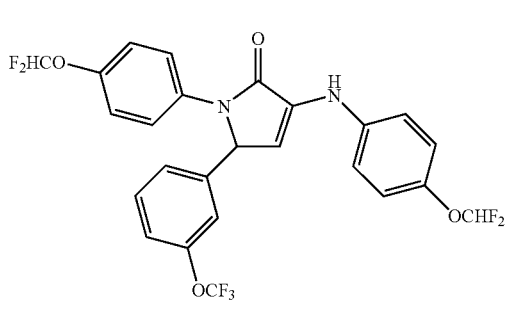<br>(±)-1-(4-Difluoromethoxy-phenyl)-3-(4-difluoromethoxy-phenylamino)-5-(3-trifluoromethoxy-phenyl)-1,5-dihydro-pyrrol-2-one | Yield 67%<br>MS (m/z): 543 (M + 1), 541 (M − 1)<br>Reaction time: 24 hours<br>Use 2.5 equivalents of the 4-(difluoromethoxy) aniline.<br>Concentrate reaction and purify by silica gel chromatography (5-20% EtOAc-hexanes). |
| 16B | 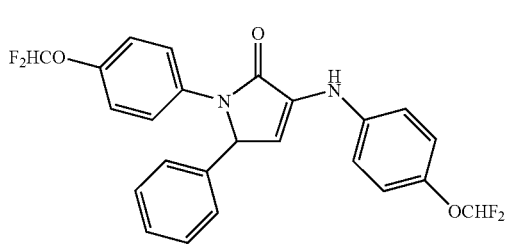<br>(±)-1-(4-Difluoromethoxy-phenyl)-3-(4-difluoromethoxy-phenylamino)-5-phenyl-1,5-dihydro-pyrrol-2-one | Yield 37%<br>MS (m/z): 459 (M + 1), 457 (M − 1)<br>Reaction time: 24 hours<br>Used 2.5 equivalents of the 4-(difluoromethoxy) aniline.<br>Wash precipitate with 4:1 heptane/MTBE. |

Preparation 17

(±)-5-(3-Methyl-phenyl)-1-(4-trifluoromethoxy-phenyl)-3-(4-trifluoromethoxy-phenylamino)-1,5-dihydro-pyrrol-2-one

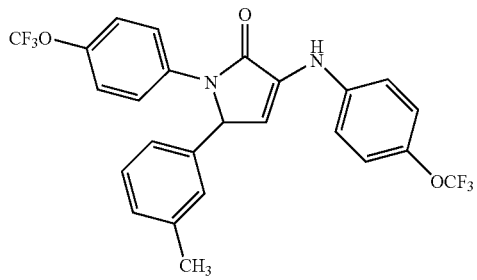

Stir a mixture of 3-methylbenzaldehyde (1.68 mL, 14.21 mmol), ethyl pyruvate (1.42 mL, 12.93 mmol), acetic acid (1.85 mL, 32.30 mmol) in anhydrous tetrahydrofuran (3.15 mL, 38.75 mmol), under an atmosphere of nitrogen. Add 4-(trifluoromethoxy)aniline (3.84 mL, 28.42 mmol) dropwise over 2 min. Heat the yellow solution to 80° C. for 12 h. Cool to ambient temperature and filter the yellow precipitate and wash with 10% acetone/water (50 mL). Dry the yellow solid under vacuum at 40° C. to afford the title compound (4.18 g, 64%). MS (m/z): 509.1 (M+1).

Prepare the following Compounds essentially by the method of Preparation 17.

TABLE 2

| Prep. N° | Compound and Name | Yield, Physical data And Comments |
|---|---|---|
| 18 | (±)-5-(2-Fluoro-phenyl)-1-(4-trifluoromethoxy-phenyl)-3-(4-trifluoromethoxy-phenylamino)-1,5-dihydro-pyrrol-2-one | Yield 89% MS (m/z): 513.1 (M + 1) Chromatograph on silica gel by elution with 50% dichloromethane/iso-hexane |
| 19 | ((±)-5-(4-Fluoro-phenyl)-1-(4-trifluoromethoxy-phenyl)-3-(4-trifluoromethoxy-phenylamino)-1,5-dihydro-pyrrol-2-one | Yield 86% MS (m/z): 513.1 (M + 1) Chromatograph on silica gel by elution with 40% Ethyl acetate/iso-hexane |
| 20 | ((±)-5-(3-Chloro-phenyl)-1-(4-trifluoromethoxy-phenyl)-3-(4-trifluoromethoxy-phenylamino)-1,5-dihydro-pyrrol-2-one | Yield 86% MS (m/z): 529.1 (M + 1) Chromatograph on silica gel by elution with 40% Ethyl acetate/iso-hexane |

TABLE 2-continued

| Prep. N° | Compound and Name | Yield, Physical data And Comments |
|---|---|---|
| 21 | (±)-5-(3-Trifluoromethyl-phenyl)-1-(4-trifluoromethoxy-phenyl)-3-(4-trifluoromethoxy-phenylamino)-1,5-dihydro-pyrrol-2-one | Yield, 43%<br>MS (m/z): 563.1 (M + 1) |
| 22 | (±)-5-(3-Trifluoromethoxy-phenyl)-1-(4-trifluoromethoxy-phenyl)-3-(4-trifluoromethoxy-phenylamino)-1,5-dihydro-pyrrol-2-one | Yield 72%<br>MS (m/z): 579.1 (M + 1)<br>Chromatograph on silica gel by elution with 40% Ethyl acetate/iso-hexane |
| 23 | (±)-5-(3-Cyano-phenyl)-1-(4-trifluoromethoxy-phenyl)-3-(4-trifluoromethoxy-phenylamino)-1,5-dihydro-pyrrol-2-one | Yield 89%<br>MS (m/z): 520.1 (M + 1) |
| 24 | (±)-5-(3,5-Difluoro-phenyl)-1-(4-trifluoromethoxy-phenyl)-3-(4-trifluoromethoxy-phenylamino)-1,5-dihydro-pyrrol-2-one | Yield 75%<br>MS (m/z): 531 (M + 1) |

TABLE 2-continued

| Prep. N° | Compound and Name | Yield, Physical data And Comments |
|---|---|---|
| 25 | (±)-1-p-Tolyl-3-p-tolylamino-5-(3-trifluoromethoxy-phenyl)-1,5-dihydro-pyrrol-2-one | Yield 53% LCMS, Ret. time = 5.52 min., Method 3, MS (m/z): 439.0 (M+), 437.0 (M − 1). |
| 25A | 5-(3-Difluoromethoxy-phenyl)-1-(4-trifluoromethoxy-phenyl)-3-(4-trifluoromethoxy-phenylamino)-1,5-dihydro-pyrrol-2-one | Yield 49.6% LCMS rt 5.57 min., Method 3, MS (m/z): 558.8 (M − 1). |

Preparation 26

(±)5-Phenyl-1-(4-trifluoromethoxyphenyl)-3-(4-trifluoromethoxyphenylamino)-1,5-dihydro-pyrrol-2-one

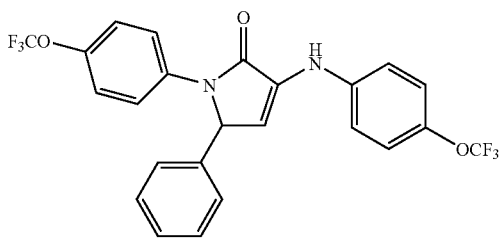

Combine benzaldehyde (50.0 g, 472 mmol), ethyl pyruvate (55.3 g, 476 mmol) and acetic acid (350 mL) at ambient temperature under a nitrogen atmosphere and stir for ~10 to 15 minutes. Add 4-(trifluoromethoxy)aniline (183.8 g, 1038 mmol) dropwise over a period of ~1 h while maintaining the temperature at ~35° C. Stir the resulting mixture at ambient temperature overnight (~16 h). Add isopropyl alcohol (350 mL) and water (350 mL). Stir the resulting mixture at ambient temperature of 15 min. Filter and rinse the solid with 1:1 isopropyl alcohol:water (2×150 mL). Dry in a vacuum oven at 40° C. overnight to yield the title compound as a yellow solid (191.4 g, 82% yield). $^1$H NMR (DMSO-$d_6$, 500 MHz): δ8.43 (s, 1H), 7.74 (dt, 2H, J=9.0 Hz, 2.8 Hz) 7.37 (dt, 2H, J=9.5 Hz, 2.2 Hz), 7.32 (d, 2H, J=9.0 Hz), 7.30-7.25 (m, 4H), 7.22-7.19 (m, 3H), 6.43 (d, 1H, J=3 Hz), 6.08 (d, 1H, J=2.5 Hz); MS (m/z): 493 (M−1).

Preparation 27

(±)5-(3-Trifluoromethoxy-phenyl)-1-(4-trifluoromethyl-phenyl)-3-(4-trifluoromethyl-phenylamino)-1,5-dihydro-pyrrol-2-one

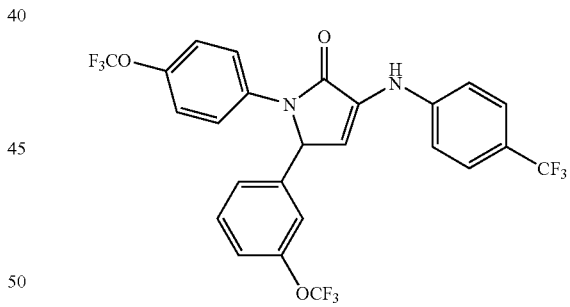

Stir 3-(trifluoromethoxy)-benzaldehyde (25.0 g, 132 mmol) and ethyl pyruvate (15.3 g, 132 mmol) in glacial acetic acid (125 mL) at ambient temperature for 10 minutes. Add 4-(trifluoromethyl)aniline (46.7 g, 290 mmol) drop-wise over 15 minutes with continued stirring, warm the solution to 30° C., and stir 22-24 h. Cool the solution to 26° C., add isopropyl alcohol (125 mL) and water (125 mL). Stir the solution at room temperature for 15 minutes, filter the precipitate and wash with a 1:1 mixture of iso-propyl alcohol-water (100 mL×2). Dry under vacuum at 40° C. to afford the titled compound (60.46 g, 84%) as a white powder: HPLC (Method 4) retention time: 10.9 minutes. MS (m/z): 545.1 (M−1). $^1$H NMR (500 MHz, DMSO-$d_6$) δ 8.76 (s, 1 H), 7.86 (d, 2 H, J=8.5 Hz), 7.70 (d, 2 H, J=8.5 Hz), 7.56 (d, 2 H, J=9.0 Hz), 7.47 (d, 2 H, J=8.5 Hz), 7.44-7.41 (m, 1 H), 7.37 (s, 1 H), 7.29 (d, 1 H, J=8.0 Hz), 7.22 (d, 1 H, J=8.0 Hz), 6.66 (d, 1 H, J=3.0 Hz), 6.29 (d, 1 H, J=2.5 Hz).

Preparation 28

(±)-1-(4-Isopropyl-phenyl)-5-(3-trifluoromethoxy-phenyl)-pyrrolidine-2,3-dione

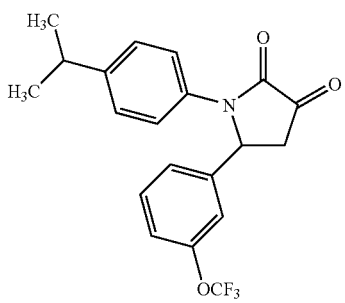

and (±)-3-Hydroxy-5-(3-trifluoromethoxy-phenyl)-1-(4-isopropyl-phenyl)-1,5-dihydro-pyrrol-2-one

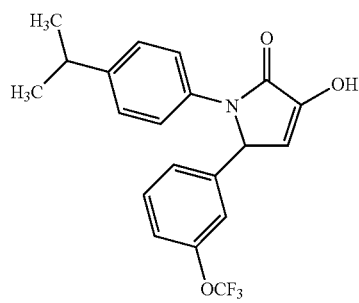

Mix (±)-1-(4-Isopropyl-phenyl)-3-(4-isopropyl-phenylamino)-5-(3-trifluoromethoxy-phenyl)-1,5-dihydro-pyrrol-2-one (2.0 g, 4.04 mmol), glacial acetic acid (30 mL) and hydrochloric acid (20 mL). Stir the reaction mixture at ambient temperature for 1 hour. Pour onto ice/water, filter the precipitate, wash with water, and dry under vacuum to afford a yellow solid. Take the yellow solid and repeat above procedure to afford the titled compound (0.9 g, 59%). MS (m/z): 378 (M+1).

Prepare the following Compounds essentially by the method of Preparation 28.

TABLE 3

| Prep. N° | Compound Name | Yield, Physical data and Comment |
|---|---|---|
| 29 | (±)-1-(4-Bromo-phenyl)-5-(3-trifluoromethoxy-phenyl)-pyrrolidine-2,3-dione<br>(±)-3-Hydroxy-5-(3-trifluoromethoxy-phenyl)-1-(4-bromo-phenyl)-1,5-dihydro-pyrrol-2-one | Yield: 100%<br>MS (m/z): 414.0 (M + 1) |
| 30 | (±)-1-p-Tolyl-5-(3-trifluoromethoxy-phenyl)-pyrrolidine-2,3-dione<br>(±)-3-Hydroxy-5-(3-trifluoromethoxy-phenyl)-1-(p-tolyl)-1,5-dihydro-pyrrol-2-one | Yield 100%.<br>LCMS, Ret. time = 3.96 min., Method 3, MS (m/z): 350.0 (M+), 348.0 (M − 1). |

Preparation 31

(S)-1-(4-Bromo-phenyl)-3-((R)-1-phenyl-ethylamino)-5-(3-trifluoromethoxy-phenyl)-1,5-dihydro-pyrrol-2-one

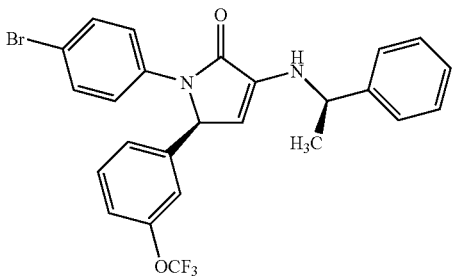

Preparation 32

(R)-1-(4-Bromo-phenyl)-3-((R)-1-phenyl-ethylamino)-5-(3-trifluoromethoxy-phenyl)-1,5-dihydro-pyrrol-2-one

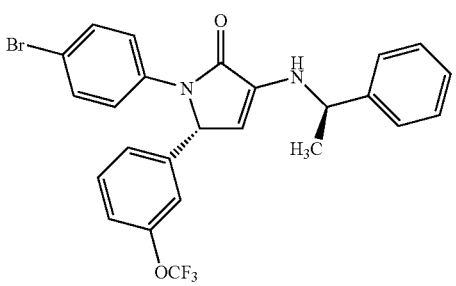

Dissolve (±)-1-(4-bromo-phenyl)-5-(3-trifluoromethoxy-phenyl)-pyrrolidine-2,3-dione (14.6 g, 35.2 mmol) in dichloromethane (35 mL). Add (R)-(+)-α-methylbenzylamine (6.8 mL, 52.8 mmol) and stir overnight at ambient temperature. Concentrate the reaction mixture under reduced pressure and purify by silica gel chromatography (ethyl acetate-hexane) to yield (S)-1-(4-bromo-phenyl)-3-((R)-1-phenyl-ethylamino)-5-(3-trifluoromethoxy-phenyl)-1,5-dihydro-pyrrol-2-one-eluting first (6.6 g, 36%): MS (m/z): 517.0 (M+1). RP HPLC: Tr=5.53 min (Method 3) and eluting second (R)-1-(4-bromo-phenyl)-3-((R)-1-phenyl-ethylamino)-5-(3-trifluoromethoxy-phenyl)-1,5-dihydro-pyrrol-2-one (5.8 g, 32%): MS (m/z): 517.0 (M+1). RP HPLC: Tr=5.44 min. (Method 3)

$^1$H NMR (400 MHz, DMSO-d$_6$) δ 7.45 (dd, 4H, J=18.5, 9.2 Hz), 7.33 (d, 2H, J=7.5 Hz), 7.28-7.19 (m, 3H), 7.15-7.05 (m,

2H), 7.15-7.05 (m, 2H), 6.99 (d, 1H, J=7.9 Hz), 6.90 (s, 1H), 5.89 (d, 1H, J=7.0 Hz), 5.85 (d, 1H, J=2.2 Hz), 5.14 (d, 1H, J=2.6 Hz), 4.35-4.26 (m, 1H), 1.43 (d, 3H, J=7.0 Hz).

Prepare the following Compound essentially by the method of Preparation 28, 31 and 32.

TABLE 4

| Prep. N° | Compound and Name | Yield and Physical Data |
|---|---|---|
| 33 | 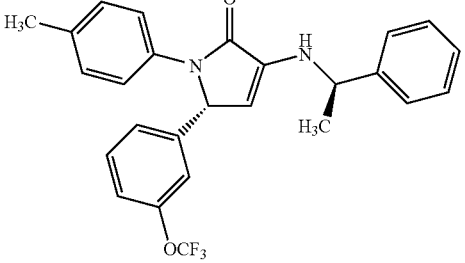<br>(R)-1-p-Tolyl 3-((R)-1-phenyl-ethylamino)-5-(3-trifluoromethoxy-phenyl)-1,5-dihydro-pyrrol-2-one | Yield 27%.<br>LCMS, Ret. time = 5.34 min.,<br>Method 3, MS (m/z): 453.0 (M+), 451.0 (M − 1). |

Preparation 34

(±)-3-Hydroxy-5-[3-(2,2,2-trifluoro-ethoxy)-phenyl]-1-(4-trifluoromethyl-phenyl)-1,5-dihydro-pyrrol-2-one

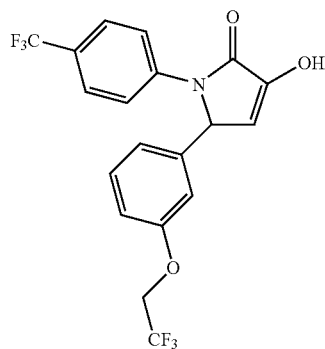

and (±)-5-[3-(2,2,2-Trifluoro-ethoxy)-phenyl]-1-(4-trifluoromethyl-phenyl)-pyrrolidine-2,3-dione

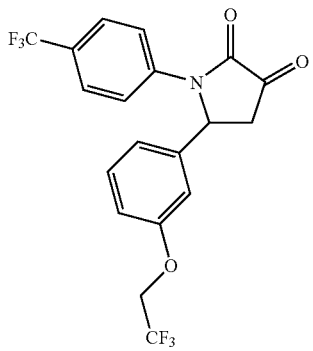

Add acetic acid (6.54 mL, 114 mmol), 2,5-dimethoxytetrahydrofuran (5.55 mL, 42.8 mmol), water (32 mL), and TFA (4.32 mL, 57.1 mmol) sequentially to a solution of (±)-5-[3-(2,2,2-trifluoro-ethoxy)-phenyl]-1-(4-trifluoromethyl-phenyl)-3-(4-trifluoromethyl-phenylamino)-1,5-dihydro-pyrrol-2-one (16.0 g, 28.6 mmol) in THF (102 mL). Heat the reaction mixture to 35° C. for 22 hours.

Cool the reaction mixture to room temperature and add isopropyl acetate (40 mL) and toluene (160 mL) in a single portion. Wash the mixture with water (3×) and then pH 7 buffer (2×). Separate layers and observe that the aqueous layer is pH=7. Wash the organic layer with water (1×) and brine (1×). Observe that the organic layer contains the titled compound. LC-MS ESI m/z: 416 (M-H).

Preparation 35

(±)5-(3-Trifluoromethoxy-phenyl)-1-(4-trifluoromethyl-phenyl)-1,5-dihydro-pyrrolidine-2,3-dione

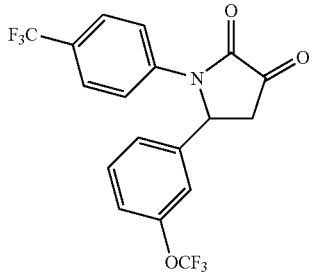

and (±)-3-Hydroxy-5-(3-trifluoromethoxy-phenyl)-1-(4-trifluoromethyl-phenyl)-1,5-dihydro-pyrrol-2-one

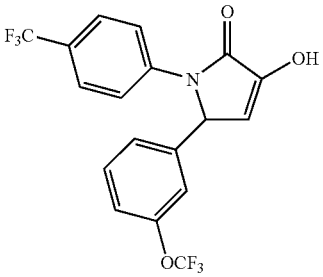

Mix ethanol (120 mL), glacial acetic acid (15 mL), water (3.0 mL, 164.7 mmol), trifluoroacetic acid (6.2 mL, 82.4 mmol), (±)-5-(3-trifluoromethoxy-phenyl)-1-(4-trifluoromethyl-phenyl)-3-(4-trifluoromethyl-phenylamino)-1,5-dihydro-pyrrol-2-one (30.0 g, 54.9 mmol), and 2,5-dimethoxy-tetrahydrofuran (10.7 mL, 82.4 mmol). Warm the solution to 50° C. and stir the reaction mixture for 15-18 hours. Discontinue heating the solution, add water (35 mL), and cool the reaction mixture to −19° C. Filter the slurry and wash the solid with a 1:4 mixture of water-methanol (20 mL). Transfer the filtrate to a separatory funnel and wash with 6% brine (280 mL), then add 6% brine (100 mL), methanol (40 mL), diethyl ether (100 mL), and saturated sodium bicarbonate solution (43 mL) to the organic phase. Separate the layers, add methanol (60 mL) to the organic phase, and concentrate the solution to approximately 1 volume containing (±)-3-hydroxy-5-(3-trifluoromethoxy-phenyl)-1-(4-trifluoromethyl-phenyl)-1,5-dihydro-pyrrol-2-one.

Preparation 36

(S)-1-(4-Trifluoromethyl-phenyl)-3-((R)-1-phenyl-ethylamino)-5-(3-trifluoromethoxy-phenyl)-1,5-dihydro-pyrrol-2-one Add (R)-(+)-α-methyl benzylamine (45.0 mL, 349.8 mmol) to the organic layer described in Preparation 34 or 35, containing (±)-3-hydroxy-5-(3-trifluoromethoxy-phenyl)-1-(4-trifluoromethyl-phenyl)-1,5-dihydro-pyrrol-2-one. Stir the solution at ambient temperature for 72 hours. Concentrate the reaction mixture and purify by silica gel chromatography (5-15% EtOAc-hexane) to yield (S)-1-(4-trifluoromethyl-phenyl)-3-((R)-1-phenyl-ethylamino)-5-(3-trifluoromethoxy-phenyl)-1,5-dihydro-pyrrol-2-one (32.4 g, 37%) as a tan foam and (R)-1-(4-trifluoromethyl-phenyl)-3-((R)-1-phenyl-ethylamino)-5-(3-trifluoromethoxy-phenyl)-1,5-dihydro-pyrrol-2-one (26.0 g, 29%) as a pale orange oil.

(S)-1-(4-trifluoromethyl-phenyl)-3-((R)-1-phenyl-ethylamino)-5-(3-trifluoromethoxy-phenyl)-1,5-dihydro-pyrrol-2-one

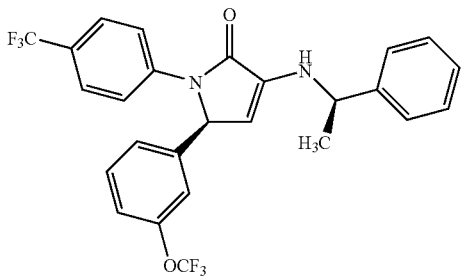

and

¹H NMR (400 MHz, DMSO-d₆) δ 7.74 (d, 2H, J=8.8Hz), 7.62 (d, 2H, J=8.8 Hz), 7.39-7.34 (m, 3H), 7.28 (dd, 2H, J=7.7, 7.1 Hz), 7.21-7.14 (m, 4H), 6.04 (d, 1H, J=7.5 Hz), 5.91 (d, 1H, J=2.6 Hz), 5.21 (d, 1H, J=2.6 Hz), 4.31-4.23 (m, 1H), 1.42 (d, 3H, J=7.0 Hz). MS (m/z): 507 (M+1).

Preparation 37

(R)-1-(4-Trifluoromethyl-phenyl)-3-((R)-1-phenyl-ethylamino)-5-(3-trifluoromethoxy-phenyl)-1,5-dihydro-pyrrol-2-one (R)-1-(4-trifluoromethyl-phenyl)-3-((R)-1-phenyl-ethylamino)-5-(3-trifluoromethoxy-phenyl) 1,5-dihydro-pyrrol-2-one

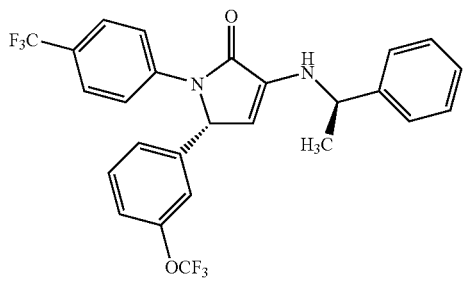

¹H NMR (400 MHz, DMSO-d₆) δ 7.76 (d, 2H, J=8.8Hz), 7.62 (d, 2H, J=8.8 Hz), 7.34 (d, 2H, J=7.0 Hz), 7.28-7.20 (m, 3H), 7.14-7.06 (m, 2H), 7.02 (d, 1H, J=7.9 Hz), 6.96 (s, 1H), 5.96-5.92 (m, 2H), 5.19 (d, 1H, J=2.6 Hz), 4.36-4.27 (m, 1H), 1.44 (d, 3H, J=7.0 Hz). MS (m/z): 507 (M+1).

Prepare the following Compounds essentially by the method of Preparation (34 or 35) and 36 and 37.

TABLE 5

| Prep. N° | Compound, Name, Physical date | Yield and Comment |
|---|---|---|
| 38 | 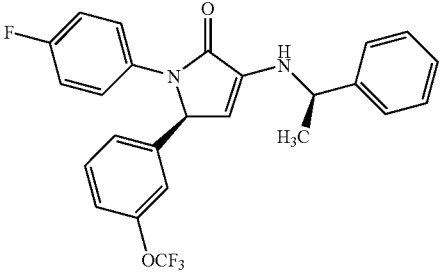<br><br>(S)-1-(4-Fluoro-phenyl)-3-((R)-1-phenyl-ethylamino)-5-(3-trifluoromethoxy-phenyl)-1,5-dihydro-pyrrol-2-one<br><br>$^1$H NMR (DMSO-$d_6$, 400 M Hz): δ 7.50-7.44 (m, 2H), 7.36-7.31 (m, 3H), 7.28-7.23 (m, 2H), 7.19-7.04 (m, 6H), 5.93 (d, 1H, J = 7.5 Hz), 5.78 (d, 1H, J = 2.6 Hz), 5.12 (d, 1H, J = 3.1 Hz), 4.28-4.19 (m, 1H), 1.39 (d, 3H, J = 6.6 Hz). MS (m/z): 457 (M + 1)<br>and | Purify by silica gel chromatography (0-25% EtOAc-hexane) to yield both diastereomers.<br><br>Yield 33%. |
| 39 | 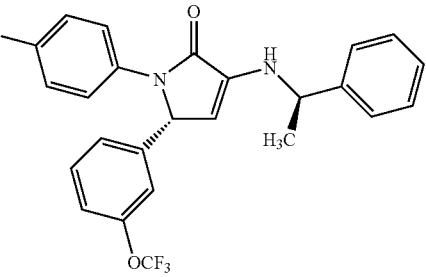<br><br>(R)-1-(4-Fluoro-phenyl)-3-((R)-1-phenyl-ethylamino)-5-(3-trifluoromethoxy-phenyl)-1,5-dihydro-pyrrol-2-one<br><br>$^1$H NMR (DMSO-$d_6$, 400 M Hz): δ 7.49-7.43 (m, 2H), 7.34-7.30 (m, 2H), 7.25-7.18 (m, 3H), 7.13-7.02 (m, 4H), 6.95 (d, 1H, J = 7.9 Hz), 6.85 (s, 1H), 5.84 (d, 1H, J = 7.5 Hz), 5.80 (d, 1H, J = 2.6 Hz), 5.10 (d, 1H, J = 2.2 Hz), 4.33-4.24 (m, 1H), 1.42 (d, 3H, J = 6.8 Hz). MS (m/z): 457 (M + 1). | Yield 34%. |
| 40 | 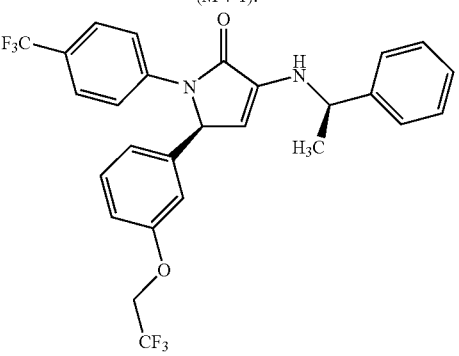<br><br>(S)-1-(4-Trifluoromethyl-phenyl)-3-((R)-1-phenyl-ethylamino)-5-[3-(2,2,2-trifluoro-ethoxy)-phenyl]-1,5-dihydro-pyrrol-2-one<br><br>$^1$H NMR (DMSO-$d_6$, 400 M Hz): δ 7.74 (d, 2H, J = 8.4 Hz), 7.59 (d, 2H, J = 8.8 Hz), 7.34 (d, 2H, J = 6.5 Hz), 7.28-7.23 (m, 2H), 7.19-7.14 (m, 2H), 6.87 (s, 1H), 6.83 (dd, 1H, J = 8.4, 2.2 Hz), 6.74 (d, 1H, J = 7.5 Hz), 5.94 (d, 1H, J = 7.0 Hz), 5.75 (d, 1H, J = 2.6 Hz), 5.12 (d, 1H, J = 2.6 Hz), 4.64 (q, 2H, J = 8.8 Hz), 4.26-4.18 (m, 1H), 1.39 (d, 3H, J = 7.0 Hz). MS (m/z): 521 (M + 1)<br>and | Purify by silica gel chromatography (0-25% EtOAc-hexane) to yield both diastereomers.<br><br>Yield 35% |

TABLE 5-continued

| Prep. N° | Compound, Name, Physical date | Yield and Comment |
|---|---|---|
| 41 | 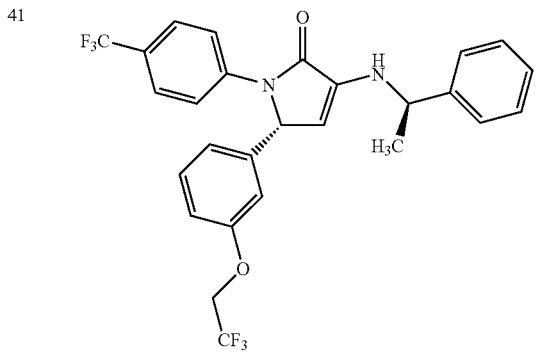<br>(R)-1-(4-Trifluoromethyl-phenyl)-3-((R)-1-phenyl-ethylamino)-5-[3-(2,2,2-trifluoro-ethoxy)-phenyl]-1,5-dihydro-pyrrol-2-one:<br><br>$^1$H NMR (DMSO-$d_6$, 400 M Hz): δ 7.76 (d, 2H, J = 8.8 Hz), 7.59 (d, 2H, J = 8.8 Hz), 7.32 (d, 2H, J = 7.0 Hz), 7.23-7.18 (m, 2H), 7.12-7.04 (m, 2H), 6.76 (dd, 1H, J = 8.1, 2.4 Hz), 6.70 (s, 1H), 6.62 (d, 1H, J = 7.5 Hz), 5.83 (d, 1H, J = 7.5 Hz), 5.80 (d, 1H, J = 2.6 Hz), 5.13 (d, 1H, J = 2.6 Hz), 4.64-4.43 (m, 2H), 4.32-4.24 (m, 1H), 1.41 (d, 3H, J = 6.6 Hz). MS (m/z): 521 (M + 1). | Yield 33% |
| 42 | 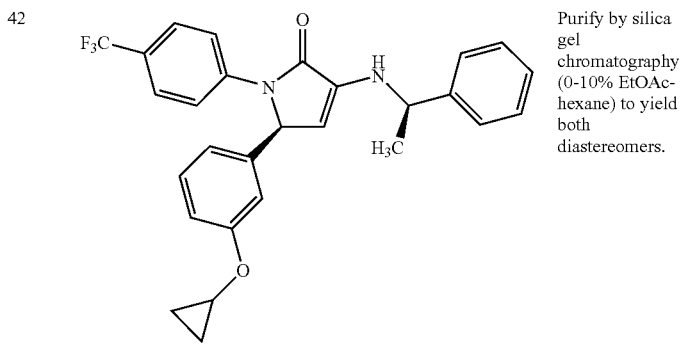<br>(S)-1-(4-Trifluoromethylphenyl)-3-((R)-1-phenyl-ethylamino)-5-(3-cyclopropoxyphenyl)-1,5-dihydro-pyrrol-2-one<br><br>LCMS: 5.53 min. (Method 3); ESMS m/z 479.2 (M + 1), 477.0 (M − 1).<br>and | Purify by silica gel chromatography (0-10% EtOAc-hexane) to yield both diastereomers.<br><br>Yield 32%. |
| 43 | 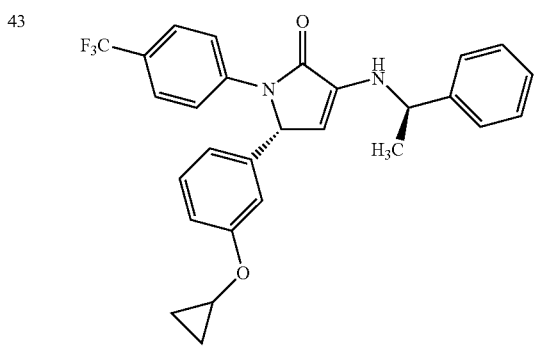<br>(R)-1-(4-Trifluoromethylphenyl)-3-((R)-1-phenyl-ethylamino)-5-(3-cyclopropoxyphenyl)-1,5-dihydro-pyrrol-2-one<br><br>LCMS: 5.44 min. (Method 3); ESMS m/z 479.2 (M + 1), 477.0 (M − 1). | Yield 34%. |

TABLE 5-continued

| Prep. N° | Compound, Name, Physical date | Yield and Comment |
|---|---|---|
| 44 | 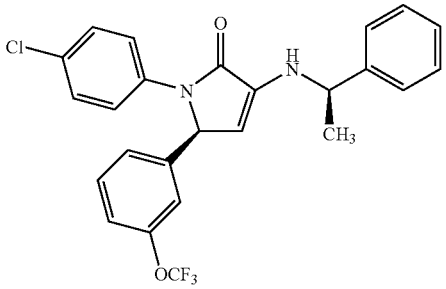<br>(S)-1-(4-Chloro-phenyl)-3-((R)-1-phenyl-ethylamino)-5-(3-trifluoromethoxy-phenyl)-1,5-dihydro-pyrrol-2-one | Purify by silica gel chromatography (0-10% EOAc-hexane) to yield both diastereomers. |
| | $^1$H NMR (DMSO-d$_6$, 400 M Hz): δ 7.52 (d, 2H, J = 9.2 Hz), 7.38-7.26 (m, 7H), 7.21-7.11 (m, 4H), 5.98 (d, 1H, J = 7.5 Hz), 5.82 (d, 1H, J = 2.6 Hz), 5.16 (d, 1H, J = 2.6 Hz), 4.29-4.22 (m, 1H), 1.41 (d, 3H, J = 7.0 Hz).<br>HPLC Ret. time = 5.54 min.<br>MS (m/z): 473.0 (M + 1).<br>and | Yield 38%. |
| 45 | 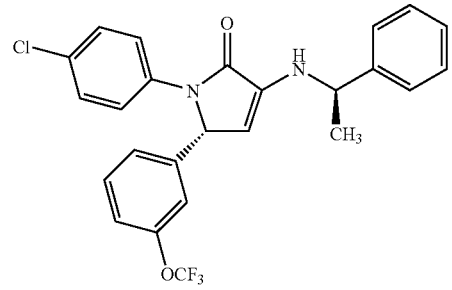<br>(R)-1-(4-Chloro-phenyl)-3-((R)-1-phenyl-ethylamino)-5-(3-trifluoromethoxy-phenyl)-1,5-dihydro-pyrrol-2-one | |
| | $^1$H NMR (DMSO-d$_6$, 400 M Hz): δ 7.53 (d, 2H, J = 9.2 Hz), 7.35-7.29 (m, 4H), 7.27-7.20 (m, 3H), 7.14-7.05 (m, 2H), 6.99 (d, 1H, J = 7.5 Hz), 6.91 (s, 1H), 5.89 (d, 1H, J = 7.5 Hz), 5.85 (d, 1H, J = 2.6 Hz), 5.14 (d, 1H, J = 2.6 Hz), 4.34-4.27 (m, 1H), 1.44 (d, 3H, J = 7.0 Hz).<br>HPLC Ret. time = 5.46 min.<br>MS (m/z): 473.0 (M + 1). | Yield 43%. |
| 46 | 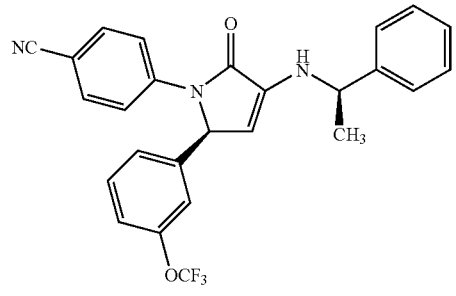<br>4-[(S)-2-Oxo-3-((R)-1-phenyl-ethylamino)-5-(3-trifluoromethoxy-phenyl)-2,5-dihydro-pyrrol-1-yl]-benzonitrile | Purify by silica gel chromatography (0-20% EtOAc-hexane) to yield both diastereomers. |
| | $^1$H NMR (DMSO-d$_6$, 400 M Hz): δ 7.73 (s, 4H), 7.39-7.35 (m, 3H), 7.28 (t, 2H, J = 7.5 Hz), 7.21-7.13 (m, 4H), 6.07 (d, 1H, J = 7.5 Hz), 5.91 (d, 1H, J = 2.6 Hz), 5.23 (d, 1H, J = 2.6 Hz), 4.30-4.23 (m, 1H), 1.41 (d, 3H, J = 6.6 Hz).<br>MS (m/z): 464.0 (M + 1).<br>HPLC Ret. time = 5.12 min.<br>and | Yield 18%. |

TABLE 5-continued

| Prep. N° | Compound, Name, Physical date | Yield and Comment |
|---|---|---|
| 47 | 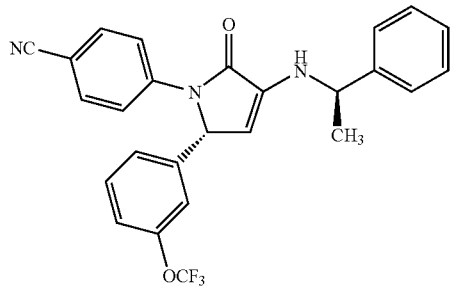<br>4-[(R)-2-Oxo-3-((R)-1-phenyl-ethylamino)-5-(3-trifluoromethoxy-phenyl)-2,5-dihydro-pyrrol-1-yl]-benzonitrile<br><br>$^1$H NMR (DMSO-$d_6$, 400 M Hz); δ 7.74 (d, 4H, J = 5.7 Hz), 7.33 (d, 2H, J = 7.5 Hz), 7.28-7.20 (m, 3H), 7.13-7.07 (m, 2H), 7.02 (d, 1H, J = 7.9 Hz), 6.97 (s, 1H), 5.98-5.94 (m, 2H), 5.20 (d, 1H, J = 2.2 Hz), 4.34-4.27 (m, 1H), 1.43 (d, 3H, J = 7.0 Hz). MS (m/z): 464.0 (M + 1).<br>HPLC Ret. time = 5.02 min. | Yield 18%. |
| 48 | 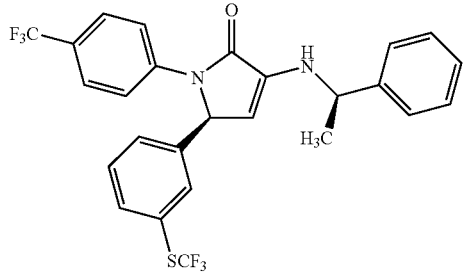<br>(S)-1-(4-Trifluoromethyl-phenyl)-3-((R)-1-phenyl-ethylamino)-5-(3-trifluoromethylsulfanyl-phenyl)-1,5-dihydro-pyrrol-2-one<br><br>LC/MS Ret. time = 5.74, Method 3, MS (m/z): 523 (M + 1).<br>and | Purify by silica gel chromatography (10% EtOAc-hexane) to yield both diastereomers.<br><br>Yield 38% |
| 49 | 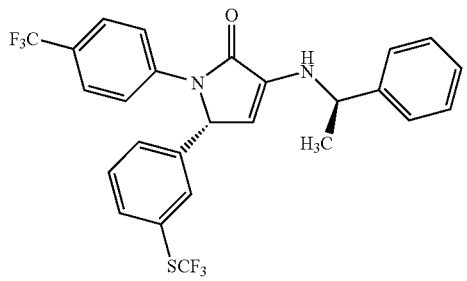<br>(R)-1-(4-Trifluoromethyl-phenyl)-3-((R)-1-phenyl-ethylamino)-5-(3-trifluoromethylsulfanyl-phenyl)-1,5-dihydro-pyrrol-2-one<br><br>LC/MS Ret. time = 5.66, Method 3, MS (m/z): 523 (M + 1). | Yield 36%. |

TABLE 5-continued

| Prep. N° | Compound, Name, Physical date | Yield and Comment |
|---|---|---|
| 50 | 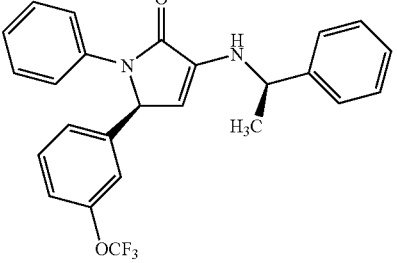<br><br>(S)-1-Phenyl-3-((R)-1-Phenyl-ethylamino)-5-(3-trifluoromethoxy-phenyl)-1,5-dihydro-pyrrol-2-one | |
| | $^1$H NMR (400 M Hz, DMSO-d$_6$) δ 7.48 (d, 2H, J = 7.9 Hz), 7.38-7.32 (m, 3H), 7.30-7.16 (m, 5H), 7.14-7.11 (m, 3H), 7.00 (dd, 1H, J = 7.2, 7.2 Hz), 5.92 (d, 1H, J = 7.5 Hz), 5.81 (d, 1H, J = 2.2 Hz), 5.14 (d, 1H, J = 2.6 Hz), 4.29-4.21 (m, 1H), 1.41 (d, 3H, J = 7.0 Hz). MS (m/z): 439 (M + 1).<br>and | Yield 36%. |
| 51 | 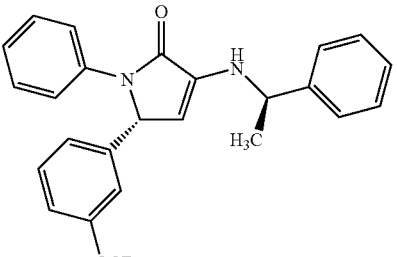<br><br>(R)-1-Phenyl-3-((R)-1-phenyl-ethylamino)-5-(3-trifluoromethoxy-phenyl)-1,5-dihydro-pyrrol-2-one | |
| | $^1$H NMR (400 M Hz, DMSO-d$_6$) δ 7.47 (d, 2H, J = 7.9 Hz), 7.33 (d, 2H, J = 7.0 Hz), 7.26-7.20 (m, 5H), 7.12 (dd, 1H, J = 7.2, 7.2 Hz), 7.07-6.96 (m, 3H), 6.89 (s, 1H), 5.85-5.82 (m 2H), 5.11 (d, 1H, J = 2.2 Hz), 4.35-4.26 (m, 1H), 1.43 (d, 3H, J = 6.6 Hz). MS (m/z): 439 (M + 1). | Yield 36%. |
| 52 | 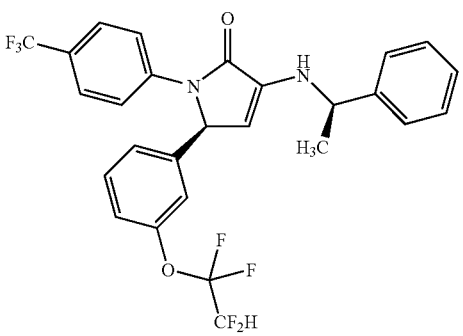<br><br>(S)-1-(4-Trifluoromethyl-phenyl)-3-((R)-1-phenyl-ethylamino)-5-[3-(1,1,2,2-tetrafluoro-ethoxy)-phenyl]-1,5-dihydro-pyrrol-2-one | |
| | $^1$H NMR (DMSO-d$_6$, 400 M Hz): δ 7.74 (d, 2H, J = 8.3 Hz), 7.62 (d, 2H, J = 8.8 Hz), 7.38-7.31 (m, 3H), 7.30-7.25 (m, 2H), 7.21-7.15 (m, 1H), 7.14-7.05 (m, 3H), 6.73 (t, 1H, J = 51.3 Hz), 6.02 (d, 1H, J = 7.5 Hz), 5.90 (d, 1H, J = 2.6 Hz), 5.21 (d, 1H, J = 2.6 Hz), 4.30-4.22 (m, 1H), 1.41 (d, 3H, J = 6.6 Hz).<br>MS (m/z): 537 (M − 1)<br>and | Yield 34%. |

TABLE 5-continued

| Prep. N° | Compound, Name, Physical date | Yield and Comment |
|---|---|---|
| 53 | 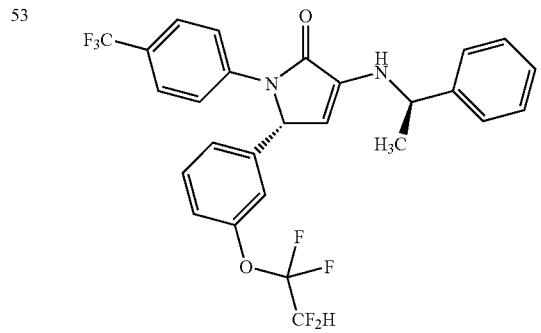

(R)-1-(4-Trifluoromethyl-phenyl)-3-((R)-1-phenyl-ethylamino)-5-[3-(1,1,2,2-tetrafluoro-ethoxy)-phenyl]-1,5-dihydro-pyrrol-2-one | |
| | $^1$H NMR (DMSO-d$_6$, 400 M Hz): δ 7.76 (d, 2H, J = 8.3 Hz), 7.61 (d, 2H, J = 8.8 Hz), 7.32 (d, 2H, J = 7.5 Hz), 7.25-7.19 (m, 3H), 7.13-7.08 (m, 1H), 7.02-6.97 (m, 2H), 6.89 (s, 1H), 6.70 (t, 1H, J = 51.6 Hz), 5.95-5.90 (m, 2H), 5.18 (d, 1H, J = 2.2 Hz), 4.35-4.16 (m, 1H), 1.43 (d, 3H, J = 7.0 Hz).<br>MS (m/z): 539 (M + 1). | Yield 35%. |
| 54 | 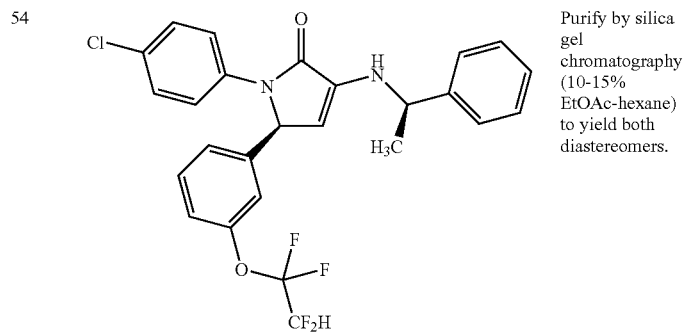

(S)-1-(4-Chloro-phenyl)-3-((R)-1-phenyl-ethylamino)-5-[3-(1,1,2,2-tetrafluoro-ethoxy)-phenyl]-1,5-dihydro-pyrrol-2-one | Purify by silica gel chromatography (10-15% EtOAc-hexane) to yield both diastereomers. |
| | $^1$H NMR (DMSO-d$_6$, 400 M Hz): δ 7.52 (d, 2H, J = 8.8 Hz), 7.38-7.25 (m, 7H), 7.21-7.15 (m, 1H), 7.11-7.03 (m, 3H), 6.73 (dd, 1H, J = 51.8, 51.8 Hz), 5.96 (d, 1H, J = 7.5 Hz), 5.81 (d, 1H, J = 2.6 Hz), 5.16 (d, 1H, J = 2.6 Hz), 4.29-4.20 (m, 1H), 1.40 (d, 3H, J = 7.0 Hz).<br>MS (m/z): 505 (M + 1)<br>and | Yield 38%. |
| 55 | 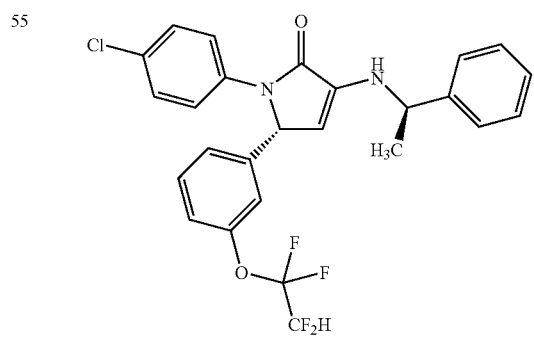

(R)-1-(4-Chloro-phenyl)-3-((R)-1-phenyl-ethylamino)-5-[3-(1,1,2,2-tetrafluoro-ethoxy)-phenyl]-1,5-dihydro-pyrrol-2-one | |

| Prep. N° | Compound, Name, Physical date | Yield and Comment |
|---|---|---|
| | $^1$H NMR (DMSO-$d_6$, 400 M Hz): δ 7.52 (d, 2H, J = 8.8 Hz), 7.34-7.28 (m, 4H), 7.24-7.19 (m, 3H), 7.14-7.08 (m, 1H), 6.99 (d, 1H, J = 8.3 Hz), 6.95 (d, 1H, J = 7.9 Hz), 6.84 (s, 1H), 6.71 (dd, 1H, J = 51.1, 51.1 Hz), 5.86 (d, 1H, J = 7.4 Hz), 5.84 (d, 1H, J = 2.3 Hz), 5.12 (d, 1H, J = 2.6 Hz), 4.35-4.25 (m, 1H), 1.43 (d, 3H, J = 7.0 Hz). MS (m/z): 505 (M + 1). | Yield 36%. |
| 56 | 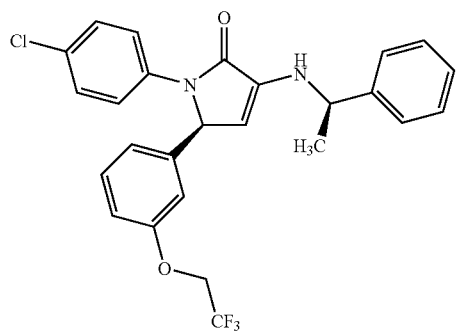<br>(S)-1-(4-Chloro-phenyl)-3-((R)-1-phenyl-ethylamino)-5-[3-(2,2,2-trifluoro-ethoxy)-phenyl]-1,5-dihydro-pyrrol-2-one | Purify by silica gel chromatography (5-20% EtOAc-hexane) to yield both diastereomers. |
| | $^1$H NMR (DMSO-$d_6$, 400 M Hz): δ 7.54 (d, 2H, J = 8.8 Hz), 7.37-7.25 (m, 6H), 7.20-7.15 (m, 2H), 6.86-6.82 (m, 2H), 6.73 (d, 1H, J = 7.5 Hz), 5.89 (d, 1H, J = 7.0 Hz), 5.68 (d, 1H, J = 2.2 Hz), 5.09 (d, 1H, J = 2.6 Hz), 4.65 (q, 2H, J = 8.8 Hz), 4.18-4.26 (m, 1H), 1.40 (d, 3H, J = 6.6 Hz), MS (m/z): 487 (M + 1) and | Yield 39%. |
| 57 | 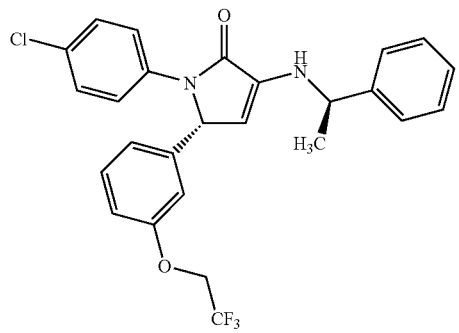<br>(R)-1-(4-Chloro-phenyl)-3-((R)-1-phenyl-ethylamino)-5-[3-(2,2,2-trifluoro-ethoxy)-phenyl]-1,5-dihydro-pyrrol-2-one | |
| | $^1$H NMR (DMSO-$d_6$, 400 M Hz): δ 7.54 (d, 2H, J = 8.8 Hz), 7.35-7.27 (m, 4H), 7.25-7.19 (m, 2H), 7.14-7.04 (m, 2H), 6.76 (dd, 1H, J = 7.9, 2.2 Hz), 6.66 (s, 1H), 6.60 (d, 1H, J = 7.9 Hz), 5.79 (d, 1H, J = 7.0 Hz), 5.72 (d, 1H, J = 1.8 Hz), 5.09 (d, 1H, J = 2.2 Hz), 4.65-4.44 (m, 2H), 4.33-4.25 (m, 1H), 1.42 (d, 3H, J = 7.0 Hz) MS (m/z): 487 (M + 1). | Yield 34%. |

TABLE 5-continued

| Prep. N° | Compound, Name, Physical date | Yield and Comment |
|---|---|---|
| 58 | 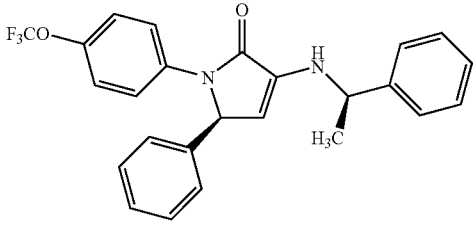(S)-1-(4-Trifluoromethoxy-phenyl)-3-((R)-(1-phenyl-ethylamino)-5-phenyl-1,5-dihydro-pyrrol-2-one | Purify by silica gel chromatography (5-10% EtOAc-hexane) to yield both diastereomers. |
| | $^1$H NMR (DMSO-$d_6$, 400 M Hz): δ 7.62 (d, 2H, J = 9.2 Hz), 7.37-7.33 (m, 2H), 7.30-7.10 (m, 10H), 5.89 (d, 1H, J = 7.5 Hz), 5.73 (d, 1H, J = 2.6 Hz), 5.12 (d, 1H, J = 2.6 Hz), 4.27-4.19 (m, 1H), 1.40 (d, 3H, J = 6.6 Hz). MS (m/z): 439 (M + 1) and | Yield 36%. |
| 59 | 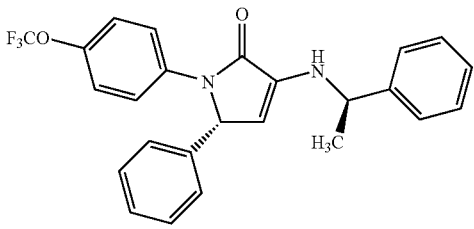(R)-1-(4-Trifluoromethoxy-phenyl)-3-((R)-(1-phenyl-ethylamino)-5-phenyl-1,5-dihydro-pyrrol-2-one | |
| | $^1$H NMR (DMSO-$d_6$, 400 M Hz): δ 7.62 (d, 2H, J = 9.2 Hz), 7.35-7.31 (m, 2H), 7.26-7.21 (m, 4H), 7.15-7.05 (m, 4H), 6.97-6.94 (m, 2H), 5.80-5.76 (m, 2H), 5.12 (d, 1H, J = 2.2 Hz), 4.34-4.25 (m, 1H), 1.43 (d, 3H, J = 6.6 Hz). MS (m/z): 439 (M + 1). | Yield 35%. |
| 60 | 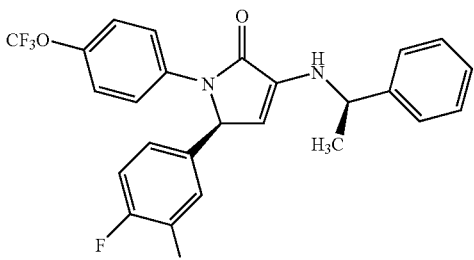(S)-1-(4-Trifluoromethoxy-phenyl)-3-((R)-1-phenyl-ethylamino)-5-(3,4-difluoro-phenyl)-1,5-dihydro-pyrrol-2-one | |
| | $^1$H NMR (400.43 M Hz, CDCl$_3$): δ 7.44 (d, J = 8.8 Hz, 2H), 7.33-7.22 (m, 5H), 7.09-6.98 (m, 3H), 6.88-6.81 (m, 2H), 5.29 (d, J = 2.2 Hz, 1H), 4.90 (d, J = 2.2 Hz, 1H), 4.66 (d, J = 4.8 Hz, 1H), 4.26 (quintet, J = 6.4 Hz, 1H), 1.52-1.49 (m, 3H). MS (m/z): 473 (M − 1). and | Yield 37%. |

TABLE 5-continued

| Prep. N° | Compound, Name, Physical date | Yield and Comment |
|---|---|---|
| 60A | (R)-1-(4-Trifluoromethoxy-phenyl)-3-((R)-1-phenyl-ethylamino)-5-(3,4-difluoro-phenyl)-1,5-dihydro-pyrrol-2-one<br><br>$^1$H NMR (400.43 M Hz, CDCl$_3$): δ 7.40 (d, J = 9.2 Hz, 2H), 7.27 (d, J = 4.0 Hz, 4H), 7.23-7.17 (m, 1H), 7.09 (d, J = 8.8 Hz, 2H), 6.96-6.89 (m, 1H), 6.70-6.66 (m, 2H), 5.32 (d, J = 2.2 Hz, 1H), 4.91 (d, J = 2.2 Hz, 1H), 4.64 (d, J = 5.3 Hz, 1H), 4.30 (quintet, J = 6.4 Hz, 1H), 1.54-1.51 (m, 3H).<br>MS (m/z): 473 (M − 1). | Yield 46%. |
| 61 | (S)-1-(4-Trifluoromethoxy-phenyl)-3-((R)-1-phenyl-ethylamino)-5-(3-chloro-phenyl)-1,5-dihydro-pyrrol-2-one<br><br>LCMS, Ret. time = 5.60 min., Method 3, MS (m/z): 473.0 (M+), 471.0 (M − 1)<br>and | Purify by silica gel chromatography (0-15% EtOAc-hexane) to yield both diastereomers.<br><br>Yield 34%. |
| 61A | (R)-1-(4-Trifluoromethoxy-phenyl)-3-((R)-1-phenyl-ethylamino)-5-(3-chloro-phenyl)-1,5-dihydro-pyrrol-2-one<br><br>LCMS, Ret. time = 5.48 min., Method 3, MS (m/z): 473.0 (M+), 471.0 (M − 1) | Yield 32%. |

TABLE 5-continued

| Prep. N° | Compound, Name, Physical date | Yield and Comment |
|---|---|---|
| 62 | 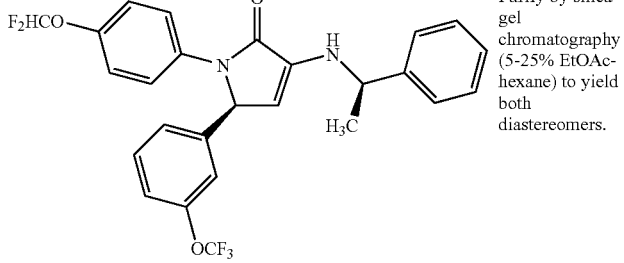<br>(S)-1-(4-Difluoromethoxy-phenyl)-3-((R)-1-phenyl-ethylamino)-5-(3-trifluoromethoxy-phenyl)-1,5-dihydro-pyrrol-2-one<br><br>LC-MS ESI m/z: 505 (M + 1)$^+$, 503 (M − H)$^-$, retention time 5.33 min, Method 3.<br>and | Purify by silica gel chromatography (5-25% EtOAc-hexane) to yield both diastereomers.<br><br>Yield 33%. |
| 62A | 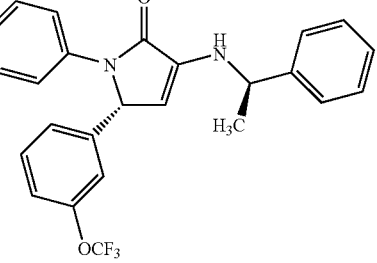<br>(R)-1-(4-Difluoromethoxy-phenyl)-3-((R)-1-phenyl-ethylamino)-5-(3-trifluoromethoxy-phenyl)-1,5-dihydro-pyrrol-2-one<br><br>LC-MS ESI m/z: 505 (M + 1)$^+$, 503 (M −+0H)$^-$, retention time 5.23 min, Method 3. | Yield 41%. |
| 63 | 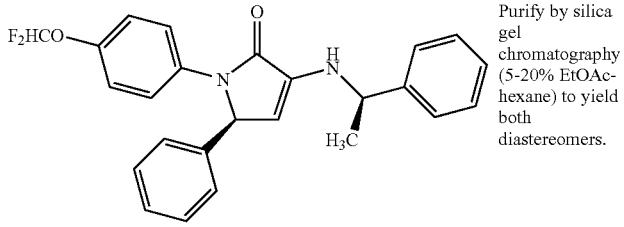<br>(S)-1-(4-Difluoromethoxy-phenyl)-5-phenyl-3-((R)-1-phenyl-ethylamino)-1,5-dihydro-pyrrol-2-one<br><br>LC-MS ESI m/z: 421 (M + 1)$^+$, retention time 5.00 min, Method 3.<br>and | Purify by silica gel chromatography (5-20% EtOAc-hexane) to yield both diastereomers.<br><br>Yield 37%. |
| 63A | 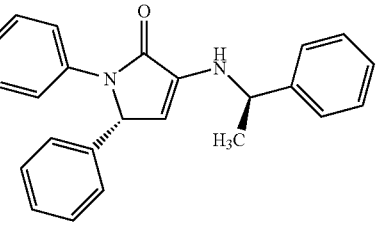<br>(R)-1-(4-Difluoromethoxy-phenyl)-5-phenyl-3-((R)-1-phenyl-ethylamino)-1,5-dihydro-pyrrol-2-one<br><br>LC-MS ESI m/z: 421 (M + 1)$^+$, retention time 4.91 min, Method 3. | Yield 34%. |

Preparation 64

(5R)-1-(4-Trifluoromethoxyphenyl)-3-((1R)-1-phenylethylamino)-5-phenyl-1,5-dihydro-pyrrol-2-one

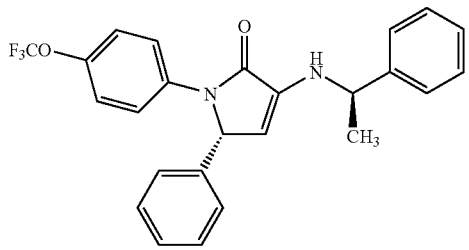

Combine (±) -5-phenyl-1-(4-trifluoromethoxyphenyl)-3-(4-trifluoromethoxyphenylamino)-1,5-dihydro-pyrrol-2-one (100 g, 202 mmol), 2,5-dimethoxytetrahydrofuran 932.4 g, 244 mmol), toluene (400 mL), water (150 mL), acetic acid (50 mL) and trifluoroacetic acid (23.5 g, 203 mmol) under a nitrogen atmosphere. Stir for 3 h while maintaining the temperature between 35° C. and 45° C. Cool to ambient temperature and transfer to a separatory funnel with toluene (100 mL). Separate the phases and wash the organic phase with water (2×500 mL). Transfer the organic phase to a separate flask with toluene (100 mL). Add (R)-(+)-α-methyl benzylamine (29.4 g, 243 mmol). Stir at ambient temperature until the reaction is complete (~18 h). Concentrate the solution under reduced pressure (40° C. to 46° C. at ~26 mm Hg) to a total volume of 250 mL. Add isopropyl alcohol (500 mL). Concentrate the resulting solution under reduced pressure (30° C. to 39° C. at ~26 mm Hg) to a total volume of 250 mL. Add isopropyl alcohol (250 mL). Cool the solution to 0° C. to −5° C. and seed with the title compound. Cool to −12° C. Stir for 1.5 h, filter, and rinse the solid with cold isopropyl alcohol (100 mL). Dry on the filter to afford 46.5 g of a tan solid. Slurry a portion of this solid (42.0 g) in heptane (300 mL) at ambient temperature for 2 h. Filter and rinse the solid with heptane (2×30 mL). Dry the solid to yield the title compound as a light tan solid (26.0 g, 32% yield). $^1$H NMR (CDCl$_3$, 500 MHz): δ7.50 (dt, 2H, J=8.5 Hz, 2.0 Hz), 7.34-7.28 (m, 4H), 7.22-7.17 (m, 4H), 7.09 (d, 2H, J=8.5 Hz), 7.00 (dd, 2H, J=7.3 Hz, 1.8 Hz), 5.41 (d, 1H, J=3.0 Hz), 5.05 (d, 1H, J=3.0 Hz), 4.65 (br s, 1H), 4.34 (q, 1H, J=6.7 Hz), 1.55 (d, 3H, J=6.7 Hz); MS (m/z): 439 (M+1).

Preparation 65

(±)5-m-Tolyl-1-(4-trifluoromethoxy-phenyl)-pyrrolidine-2,3-dione

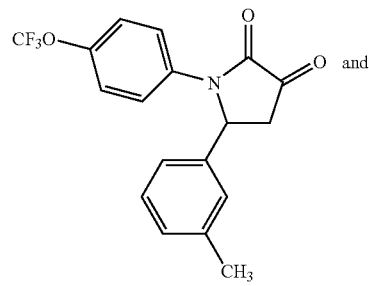

and (±)-3-Hydroxy-5-m-tolyl-1-(4-trifluoromethoxy-phenyl)-1,5-dihydro-pyrrol-2-one

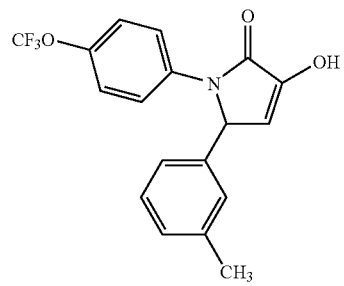

Charge THF (20 mL, 5 vols) to a flask containing (±)-5-(3-methyl-phenyl)-1-(4-trifluoromethoxy-phenyl)-3-(4-trifluoromethoxy-phenylamino)-1,5-dihydro-pyrrol-2-one (4.18 g, 8.22 mmol). Add acetic acid (1.88 mL, 32.89 mmol,) to the above clear solution to afford a yellow solution. Add 2,5-dimethoxytetrahydrofuran (1.28 mL, 9.87 mmol,), then add water (0.2 mL, 9.87 mmol). Add TFA (1.25 mL, 16.44 mmol,) to the reaction mixture and observe a slight exotherm (23 to 30° C.). Heat the reaction mixture to 40° C. for 22 hours. Pour the brown solution into water (50 mL) and extract with ethyl acetate (50 mL×2). Wash the organic phase with saturated sodium bicarbonate solution (20 mL×2), brine (50 mL), dry over magnesium sulfate and evaporate to afford the titled compound. MS (m/z): 350.1 (M+1).

Prepare the following Compounds essentially by the method of Preparation 65.

TABLE 6

| Prep. N° | Compound and Name | Yield, Physical data and Comment |
|---|---|---|
| 66 | (±)-5-Phenyl-1-(4-trifluoromethoxy-phenyl)-pyrrolidine-2,3-dione | MS (m/z): 336.1 (M + 1) |
|  | (±)-3-Hydroxy-5-phenyl-1-(4-trifluoromethoxy-phenyl)-1,5-dihydro-pyrrol-2-one | Used without purification |
| 67 | (±)-5-(2-Fluoro-phenyl)-1-(4-trifluoromethoxy-phenyl)-pyrrolidine-2,3-dione | MS (m/z): 354 (M + 1) |
|  | (±)-3-Hydroxy-5-(2-Fluoro-phenyl)-1-(4-trifluoromethoxy-phenyl)-1,5-dihydro-pyrrol-2-one | Used without purification |
| 68 | (±)-5-(4-Fluoro-phenyl)-1-(4-trifluoromethoxy-phenyl)-pyrrolidine-2,3-dione | MS (m/z): 354.3 (M + 1) |
|  | (±)-3-Hydroxy-5-(4-Fluoro-phenyl)-1-(4-trifluoromethoxy-phenyl)-1,5-dihydro-pyrrol-2-one | Used without purification |

TABLE 6-continued

| Prep. N° | Compound and Name | Yield, Physical data and Comment |
|---|---|---|
| 69 | (±)-5-(3-Chloro-phenyl)-1-(4-trifluoromethoxy-phenyl)-pyrrolidine-2,3-dione | MS (m/z): 370.1 (M + 1) |
|  | (±)-3-Hydroxy-5-(3-Chloro-phenyl)-1-(4-trifluoromethoxy-phenyl)-1,5-dihydro-pyrrol-2-one | Used without purification |
| 70 | (±)-5-(3-Trifluoromethyl-phenyl)-1-(4-trifluoromethoxy-phenyl)-pyrrolidine-2,3-dione | MS (m/z): 404 (M + 1) |
|  | (±)-3-Hydroxy-5-(3-trifluoromethyl-phenyl)-1-(4-trifluoromethoxy-phenyl)-1,5-dihydro-pyrrol-2-one | Used without purification. |
| 71 | (±)-5-(3-Trifluoromethoxy-phenyl)-1-(4-trifluoromethoxy-phenyl)-pyrrolidine-2,3-dione | MS (m/z): 420 (M + 1) |
|  | (±)-3-Hydroxy-5-(3-trifluoromethoxy-phenyl)-1-(4-trifluoromethoxy-phenyl)-1,5-dihydro-pyrrol-2-one | Used without purification |
| 72 | (±)-5-(-3-Cyano-phenyl)-1-(4-trifluoromethoxy-phenyl)-pyrrolidine-2,3-dione | MS (m/z): 361.1 (M + 1) |
|  | (±)-3-Hydroxy-5-(-3-Cyano-phenyl)-1-(4-trifluoromethoxy-phenyl)-1,5-dihydro-pyrrol-2-one | Used without purification |
| 73 | (±)-5-(3,5-Difluoro-phenyl)-1-(4-trifluoromethoxy-phenyl)-pyrrolidine-2,3-dione | MS (m/z): 372 (M + 1) |
|  | (±)-3-Hydroxy-5-(3,5-Difluoro-phenyl)-1-(4-trifluoromethoxy-phenyl)-1,5-dihydro-pyrrol-2-one | Used without purification. |
| 74 | (±)-5-(2-Chloro-phenyl)-1-(4-trifluoromethoxy-phenyl)-pyrrolidine-2,3-dione | MS (m/z): 368.0 (M − 1) |
|  | (±)-3-Hydroxy-5-(2-Chloro-phenyl)-1-(4-trifluoromethoxy-phenyl)-1,5-dihydro-pyrrol-2-one | Extract with toluene and use solution in next transformation |
| 75 | (±)-5-(3-Ethyl-phenyl)-1-(4-trifluoromethoxy-phenyl)-pyrrolidine-2,3-dione | MS (m/z): 364.0 (M − 1) |
|  | (±)-3-Hydroxy 5-(3-ethyl-phenyl)-1-(4-trifluoromethoxy-phenyl)-1,5-dihydro-pyrrol-2-one | Extract with toluene and use solution in next transformation |
| 76 | (±)-5-[3-(1,1-Difluoro-ethyl)-phenyl]-1-(4-trifluoromethoxy-phenyl)-pyrrolidine-2,3-dione | MS (m/z): 400.0 (M + 1) |
|  | (±)-3-Hydroxy-5-[3-(1,1-difluoro-ethyl)-phenyl]-1-(4-trifluoromethoxy-phenyl)-1,5-dihydro-pyrrol-2-one | Extract with toluene and use solution in next transformation |
| 76A | (±)-3-Hydroxy-5-[3-difluoromethoxy-phenyl]-1-(4-trifluoromethoxy-phenyl)-1,5-dihydro-pyrrol-2-one | MS (m/z): 400.0 (M − 1) |
|  | (±)-5-[3-Difluoromethoxy-phenyl]-1-(4-trifluoromethoxy-phenyl)-pyrrolidine-2,3-dione | |

Preparation 77

(±)-3-[1-Methyl-1-(6-trifluoromethyl-pyridin-3-yl)-ethylamino]-5-(m-tolyl)-1-(4-trifluoromethoxy-phenyl)-1,5-dihydro-pyrrol-2-one

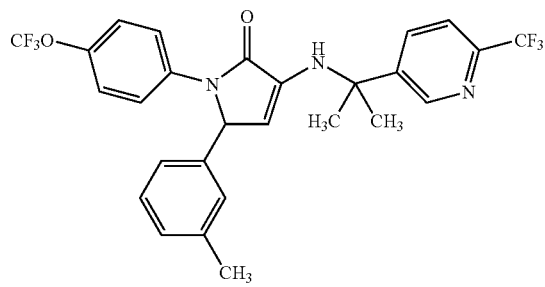

Charge toluene (20 mL) to a flask containing (±)-5-m-tolyl-1-(4-trifluoromethoxy-phenyl)-pyrrolidine-2,3-dione (4.13 g; 11.82 mmol). Add 1-methyl-1-(6-trifluoromethyl-pyridin-3-yl)-ethylamine (4.83 g, 23.65 mmol) to the above solution in an atmosphere of $N_2$. Heat the reaction mixture to 80° C. for 24 hours. Cool to ambient temperature and evaporate in vacuo. Dissolve in MeOH (90 mL) and pass through an SCX-2 ion exchange resin cartridge. Evaporate the MeOH wash to give the crude product. Purify on an SCX-2 ion exchange resin cartridge (eluent with methanol) and then by chromatography on a silica gel column eluting with iso-hexane/ethyl acetate (80:20) to afford the titled compound (2.54 g, 58%). MS (m/z): 536.1 (M+1).

Prepare the following Compounds essentially by the method of Preparation 77.

TABLE 7

| Prep N° | Compound and Name | Yield, Physical Data, Comments |
|---|---|---|
| 78 | 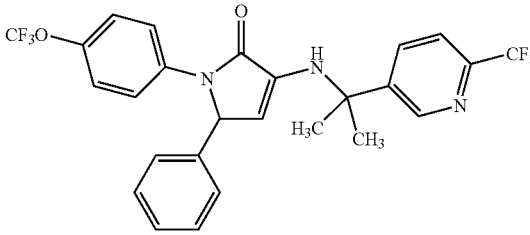<br>(±)-3-[1-Methyl-1-(6-trifluoromethyl-pyridin-3-yl)-ethylamino]-5-(phenyl)-1-(4-trifluoromethoxy-phenyl)-1,5-dihydro-pyrrol-2-one | Yield: 56%<br>MS (m/z): 522.1 (M + 1)<br>Chromatographed on silica gel using 5% ethyl acetate/dichloromethane |
| 79 | 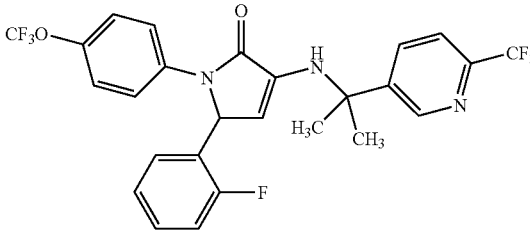<br>(±)-3-[1-Methyl-1-(6-trifluoromethyl-pyridin-3-yl)-ethylamino]-5-(2-fluoro-phenyl)-1-(4-trifluoromethoxy-phenyl)-1,5-dihydro-pyrrol-2-one | Yield: 47%<br>MS (m/z): 540.1 (M + 1)<br>Chromatographed on silica gel using 5% ethyl acetate/dichloromethane |
| 80 | 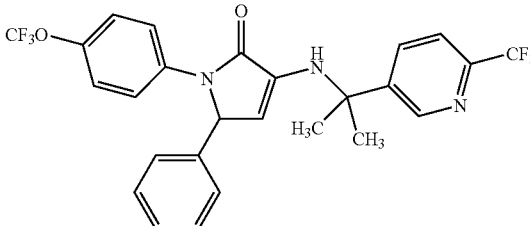<br>(±)-3-[1-Methyl-1-(6-trifluoromethyl-pyridin-3-yl)-ethylamino]-5-(4-fluoro-phenyl)-1-(4-trifluoromethoxy-phenyl)-1,5-dihydro-pyrrol-2-one | Yield: 34%.<br>MS (m/z): 540.1 (M + 1) |
| 81 | 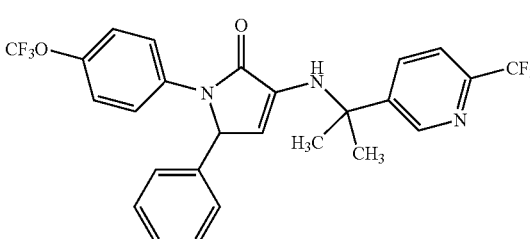<br>(±)-3-[1-Methyl-1-(6-trifluoromethyl-pyridin-3-yl)-ethylamino]-5-(3-chloro-phenyl)-1-(4-trifluoromethoxy-phenyl)-1,5-dihydro-pyrrol-2-one | Yield: 21%<br>MS (m/z): 556.1 (M + 1) |

TABLE 7-continued

| Prep N° | Compound and Name | Yield, Physical Data, Comments |
|---|---|---|
| 82 | 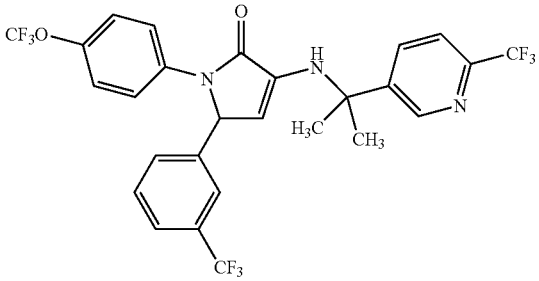<br>(±)-3-[1-Methyl-1-(6-trifluoromethyl-pyridin-3-yl)-ethylamino]-5-(3-trifluoromethyl-phenyl)-1-(4-trifluoromethoxy-phenyl)-1,5-dihydro-pyrrol-2-one | Yield: 48%<br>MS (m/z): 590.1 (M + 1) |
| 83 | 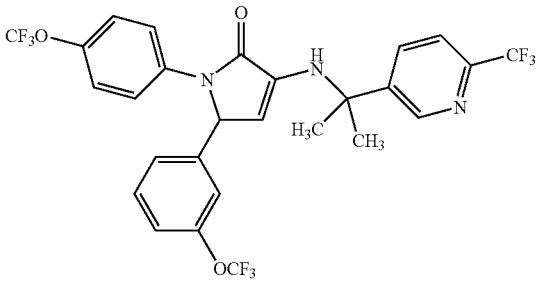<br>(±)-3-[1-Methyl-1-(6-trifluoromethyl-pyridin-3-yl)-ethylamino]-5-(3-trifluoromethoxy-phenyl)-1-(4-trifluoromethoxy-phenyl)-1,5-dihydro-pyrrol-2-one | Yield: 38%<br>MS (m/z): 606.1 (M + 1) |
| 84 | 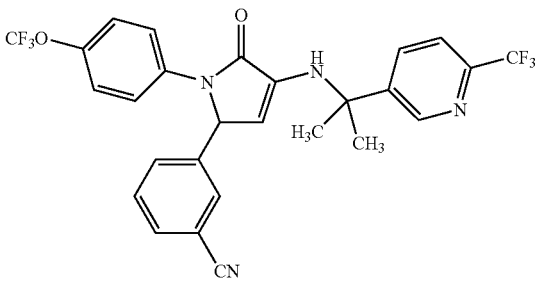<br>(±)-3-[1-Methyl-1-(6-trifluoromethyl-pyridin-3-yl)-ethylamino]-5-(3-cyano-phenyl)-1-(4-trifluoromethoxy-phenyl)-1,5-dihydro-pyrrol-2-one | Yield: 30%<br>MS (m/z): 547.1 (M + 1) |
| 85 | 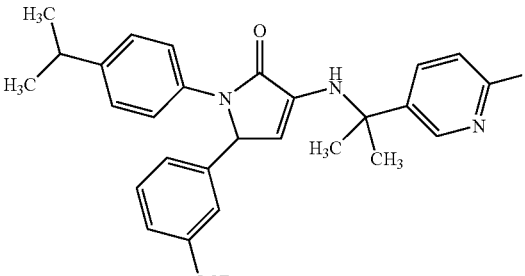<br>(±)-3-[1-Methyl-1-(6-trifluoromethyl-pyridin-3-yl)-ethylamino]-5-(3-trifluoromethoxy-phenyl)-1-(4-isopropyl-phenyl)-1,5-dihydro-pyrrol-2-one | Yield: 45%<br>MS (m/z): 564.0 (M + 1)<br>Purified over silica eluting with EtOAc:Hex. |

TABLE 7-continued

| Prep N° | Compound and Name | Yield, Physical Data, Comments |
|---|---|---|
| 86 | 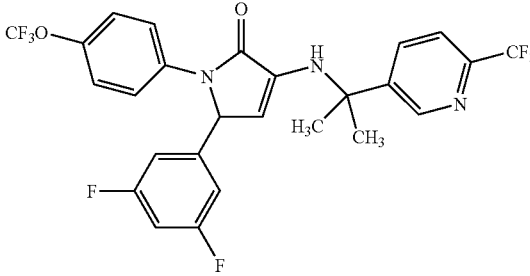<br>(±)-3-[1-Methyl-1-(6-trifluoromethyl-pyridin-3-yl)-ethylamino]-5-(3,5-difluoro-phenyl)-1-(4-trifluoro-methoxy-phenyl)-1,5-dihydro-pyrrol-2-one | Yield: 55%<br>MS (m/z): 558 (M + 1)<br>Chromatographed on silica gel using 20% ethyl acetate/iso-hexane |
| 87 | 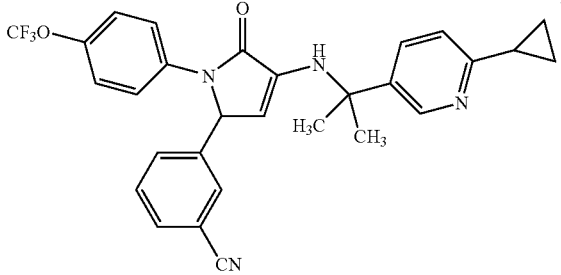<br>(±)-3-[4-[1-(6-Cyclopropyl-pyridin-3-yl)-1-methyl-ethylamino]-5-oxo-1-(4-trifluoromethoxy-phenyl)-2,5-dihydro-1H-pyrrol-2-yl]-benzonitrile | Yield: 33%<br>MS (m/z): 519 (M + 1)<br>Chromatographed on silica gel using 20% ethyl acetate/iso-hexane |
| 88 | 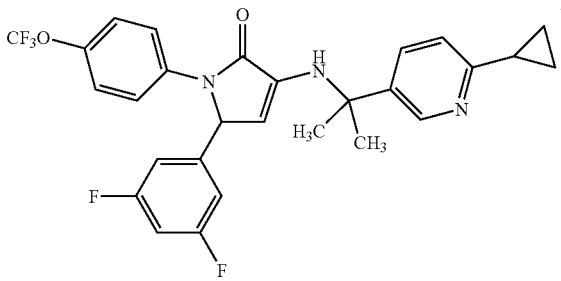<br>(±)-3-[1-(6-Cyclopropyl-pyridin-3-yl)-1-methyl-ethylamino]-5-(3,5-difluoro-phenyl)-1-(4-trifluoro-methoxy-phenyl)-1,5-dihydro-pyrrol-2-one | Yield: 30%<br>MS (m/z): 530 (M + 1)<br>Chromatographed on silica gel using 20% ethyl acetate/iso-hexane |
| 89 | 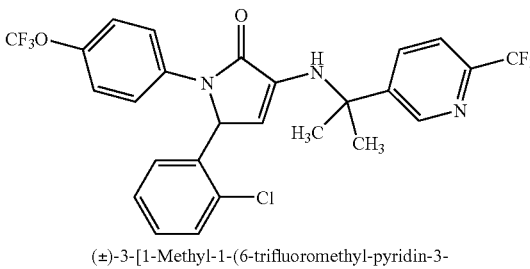<br>(±)-3-[1-Methyl-1-(6-trifluoromethyl-pyridin-3-yl)-ethylamino]-5-(2-chloro-phenyl)-1-(4-trifluoromethoxy-phenyl)-1,5-dihydro-pyrrol-2-one | Use crude material in subsequent transformation.<br>MS (m/z): 556.0 (M + 1) |

TABLE 7-continued

| Prep N° | Compound and Name | Yield, Physical Data, Comments |
|---|---|---|
| 90 | 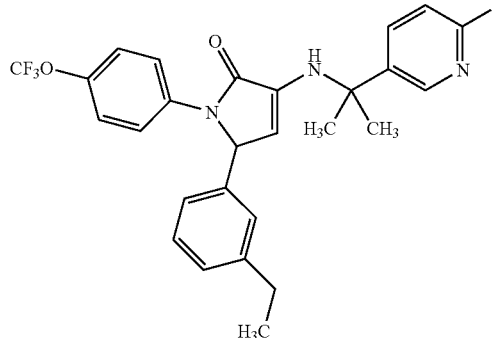(±)-3-[1-Methyl-1-(6-trifluoromethyl-pyridin-3-yl)-ethylamino]-5-(3-ethyl-phenyl)-1-(4-trifluoromethoxy-phenyl)-1,5-dihydro-pyrrol-2-one | Yield: 38%<br>MS (m/z): 550.0 (M + 1)<br>Chromatographed on silica gel using 20% ethyl acetate/hexane |
| 91 | 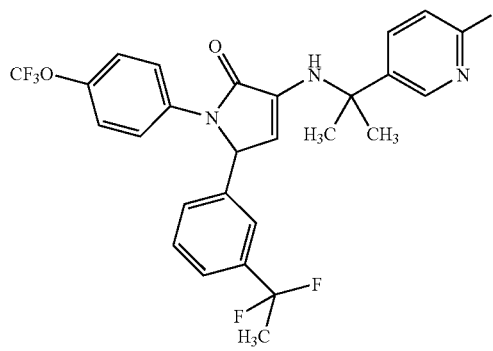(±)-3-[1-Methyl-1-(6-trifluoromethyl-pyridin-3-yl)-ethylamino]-5-[3-(1,1-difluoro-ethyl)-phenyl]-1-(4-trifluoromethoxy-phenyl)-1,5-dihydro-pyrrol-2-one | Yield: 27%<br>MS (m/z): 586 (M + 1)<br>Chromatographed on silica gel using 20% ethyl acetate/hexane |
| 91A | 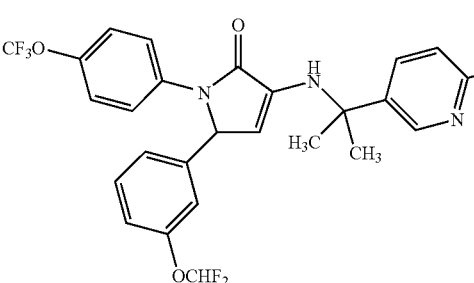(±)-5-(3-Difluoromethoxy-phenyl)-3-[1-methyl-1-(6-trifluoromethyl-pyridin-3-yl)-ethylamino]-1-(4-trifluoromethoxy-phenyl)-1,5-dihydro-pyrrol-2-one | Yield: 49%<br>MS (m/z): 588.0 (M + 1)<br>Chromatographed on silica gel using 20% ethyl acetate/iso-hexane |

Preparation 92

(5R)-3-[1-Methyl-1-(6-trifluoromethyl-pyridin-3-yl)-ethylamino]-5-phenyl-1-(4-trifluoromethoxy-phenyl)-1,5-dihydro-pryrrol-2-one

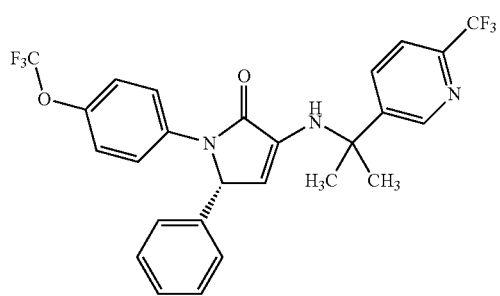

Add water (550 mL) and trifluoroacetic acid (142 mL, 1.8 mol) to a stirred slurry of (R)-1-(4-trifluoromethoxy-phenyl)-3-((R)-(1-phenyl-ethylamino)-5-phenyl-1,5-dihydro-pyrrol-2-one (275 g, 621 mmol) in 1.37 L of toluene. Stir the resulting biphasic mixture for 3.5 h at ambient temperature under a nitrogen atmosphere. Transfer the mixture into reactor equipped with a bottom valve by cannula and dilute with water (2.0 L) and toluene (2.0 L). Discard the aqueous layer, and wash the organic phase with 1N HCl (1 L). Transfer the organic layer into a new flask and charge with acetic acid (200 mL), and 1-methyl-1-(6-trifluoromethyl-pyridin-3-yl)-ethylamine (191 g, 939 mmol). Stir the mixture for 2 hours at ambient temperature and then heat to 40° C. for 96 h. Add MTBE (2.0 L) and wash with water (2.0 L). Discard the aqueous layer and wash the organic phase with saturated sodium hydrogen carbonate (2.0 L). Dry the MTBE phase with magnesium sulfate, filter and concentrate to an oil under reduced pressure (10 torr, 30° C.). Dilute the oil with 1.0 L of 15% MTBE/hexanes and stir the resulting slurry for 1 hour at ambient temperature. Isolate the solid by vacuum filtration, rinsing the solid with 200 mL of 15% MTBE/hexanes (200 mL). Dry the solid under reduced pressure to obtain (5R)-3-[1-methyl-1-(6-trifluoromethyl-pyridin-3-yl)-ethylamino]-5-phenyl-1-(4-trifluoromethoxy-phenyl)-1,5-dihydro-pryrrol-2-one as a white solid (326 g, 88%).

$^1$H NMR (400 MHz, DMSO-$d_6$) δ 8.78 (1 H, d, J=4 Hz), 8.05 (1 H, dd, J=4, 8 Hz,), 7.80 (1 H, d, J=8 Hz), 7.63 (2 H, m), 7.26 (2 H, m), 7.08-7.18 (5 H, m,), 7.02 (2 H, m), 5.72 (2 H, m), 4.77 (1 H, m), 1.65 (3 H, s), 1.62 (3H, s); MS (m/z): 522.0 (M+1).

Preparation 93

1-(6-Chloropyridin-3-yl)-1-methylethylamine

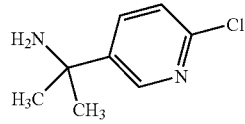

Reference: *J. Org. Chem.* 1992, 57 (16), 4521-4527.

Dry cerium(III) chloride heptahydrate (22.4 g, 30.1 mmol) at 140° C. under vacuum overnight. Cool to ambient temperature and add THF (120 mL). Stir the mixture for 30 min. to 2 hours. Cool the mixture to −78° C. and add methyllithium (1.6 M in Et$_2$O; 38 mL, 30 mmol) dropwise. Stir the reaction mixture at −78° C. for 30 min. to 1 hour and then add a solution of 2-chloropyridine-5-carbonitrile 2.77 g, 20.0 mmol) in THF (20 mL). Stir 30 min. to 4 hours at −78° C., allow the reaction mixture to warm to 20° C. for 1 hour. Cool the reaction mixture to −78° C. and add aqueous ammonia (38 mL). Allow the reaction mixture to warm to 20° C. for 1 hour. Decant the supernatant and wash the solid residue with dichloromethane. Concentrate in vacuo the combined organic layers. Transfer the resultant residue to a column of silica gel (330 g) and elute (0-10% [1 M ammonia in methanol]/dichloromethane) to yield 2.21 g (64.8%) of the titled compound as a yellow oil. MS (m/z): 171.0 (M+1). $^1$H NMR indicated pure desired product. $^1$H NMR (CDCl$_3$): δ=8.53 (d, J=2.4 Hz, 1 H), 7.82 (dd, J=8.4, 2.4 Hz, 1 H), 7.26 (dd, J=8.4, 0.8 Hz, 1 H), 1.87 (s, 2 H), 1.50 (s, 6 H) ppm.

Prepare the following Compounds essentially by the method of Preparation 93.

TABLE 8

| Prep. N° | Compound and Name | Yield, Physical data, Comment |
|---|---|---|
| 94 | ![structure] 1-(6-Cyclopropylpyridin-3-yl)-1-methylethylamine | Yield 51%. MS (m/z): 177.3 (M + 1). Keep reaction at −78° C. for 4 hours before quenching with aqueous NH$_3$. |
| 95 | ![structure] 1-(6-trifluoromethyl-pyridin-3-yl)-1-methylethyl-amine | Yield 88%. MS (m/z): 205 (M + 1). |

Preparation 96

3-Trifluoromethylsulfanyl-benzaldehyde

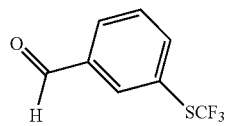

Add a solution of dimethyl sulfoxide (0.82 mL, 11.5 mmol) in dichloromethane (2 mL) over a period of 5 minutes to a solution of oxalyl chloride (0.46 mL, 5.28 mmol) in dichloromethane (10 mL) cooled to −78° C. Stir 10 minutes then add a solution of (3-trifluoromethylsulfanyl-phenyl)-methanol (1.00 g, 4.80 mmol) in dichloromethane (4 mL). Stir 15 minutes then add triethylamine (3.35 mL, 24.0 mmol). Slowly warm to ambient temperature, add water and separate the organic layer. Extract the aqueous layer with dichloromethane. Dry (sodium sulfate) the combined organic layers, filter, and concentrate in vacuo. Purify by silica gel chromatography (10% ethyl acetate/hexane) to afford the titled compound as a yellow liquid (896 mg, 91%). $^1$H NMR (400 MHz, DMSO) δ 7.74 (dd, J=7.6, 7.6, 1H), 8.01 (d, J=7.9, 1H), 8.09 (d, J=7.5, 1H), 8.12 (s, 1H), 10.03 (s, 1H).

Preparation 97

6-Cyclopropylnicotinonitrile

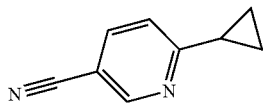

Deoxygenate a mixture of 2-bromo-5-cyanopyridine (1.83 g, 10.0 mmol), cyclopropylboronic acid (1.1 g, 13 mmol), palladium(II) acetate (0.11 g, 0.49 mmol), and potassium phosphate (7.4 g, 35 mmol) in toluene (40.00 mL) and water (2 mL) by bubbling nitrogen through the mixture. Add tricyclohexylphosphine (1.0 mL, 1.0 mmol, 1 M in toluene). Heat the reaction mixture at 100° C. for 14 hours and allow the reaction mixture to cool. Decant the supernatant and wash the leftover sludge with dichloromethane. Concentrate the combined organics in vacuo. Purify by silica gel chromatography (0-5% ethyl acetate/hexane) to afford the titled compound as a white crystalline solid (774 mg, 47%). $^1$H NMR (400 MHz, CDCl$_3$) δ 1.08 (m, 4H), 2.05 (m, 1H), 7.23 (dd, J=8.2, 1.0 Hz, 1H), 7.73 (dd, J=8.0, 2.4 Hz, 1H), 8.66 (d, J=1.2 Hz, 1H).

Preparation 98

6-Trifluoromethyl-nicotinic acid ethyl ester

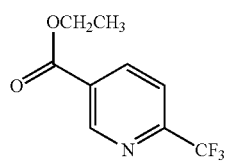

Prepare the titled compound, via the procedure described in the German patent entitled "Preparation of 6-(haloalkyl)-3-pyridinecarboxylic acids". Mueller, Peter. (Bayer A.-G., Germany). Eur. Pat. Appl. (2003), 13 pp. EP 1340747 A1 20030903. $^1$H NMR (DMSO-d$_6$, 500 MHz): δ 9.19 (s, 1H), 8.53 (dd, 1H, J=1.5, 8.5), 8.04 (d, 1H, J=8), 4.38 (q, 2H, J=7), 1.34 (t, 3H, J=7).

Preparation 99

2-(6-Trifluoromethyl-pyridin-3-yl)-propan-2-ol

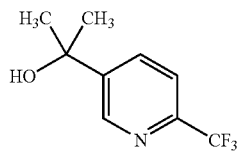

Cool the contents of an inerted reaction vessel containing technical grade 6-trifluoromethyl-nicotinic acid ethyl ester (45.6 moles; 10.00 kg) and tert-butyl methyl ether (71.6 L; 53.0 kg) to 10-15° C., and add the solution into a separate inerted reaction vessel cooled to 5-12° C. containing 3 M methylmagnesium chloride (136.8 moles; 45.6 L; 46.2 kg) and tetrahydrofuran (76.5 L; 68.0 kg). Observe a moderate exotherm during the addition, and maintain the internal reaction temperature between 15-25° C. Confirm that the starting ester is completely consumed by HPLC, and cool the reactor contents to 0-3° C. Add the contents from the reaction vessel slowly to a separate reactor cooled to 0-5° C. containing hydrochloric acid (203 moles; 16.67 L; 20.0 kg) and water (81.0 L, 81.0 kg), and observe gas evolution. Separate the layers and extract the aqueous phase once with tert-butyl methyl ether (59.5 L; 44.0 kg). Combine the organic layers and wash with a 20% sodium chloride solution (189.3 moles; 46.5 L; 55.3 kg). Filter the organic solution, concentrate to approximately 1 volume, and dilute with acetonitrile (31.8 L; 25.0 kg). Concentrate the solution to approximately 1 volume to provide the titled compound as a technical grade oil (7.9 kg; 84.4%, based on HPLC) in acetonitrile. Use the crude material as a solution in acetonitrile without further purification. A pure sample of the product can be obtained by following the procedure given below.

Purification (Optional): Charge the titled compound (1.81 kg, 8.82 moles) to a 22-L separatory funnel with methyl t-butyl ether (3 L, 2.2 Kg), water (500 mL) and saturated aqueous sodium bicarbonate (500 mL) and stir for 10 min. Separate the bright yellow aqueous layer and transfer the organic phase to a 22-L flask. Add magnesium sulfate (200 g, 1.66 moles) to the flask, stir 10 min. then filter. Concentrate the filtrate to an oil and co-evaporate twice with acetonitrile (2×3 L) to afford the titled compound as an oil weighing 1.64 kg (90.6%). $^1$H NMR (DMSO-d$_6$, 500 MHz): δ 8.85 (d, 1 H, J=2.5 Hz), 8.10 (dd, 1 H, J=2, 8 Hz), 7.81 (d, 1 H, J=8 Hz), 5.42 (s, 1 H), 1.47 (s, 6 H).

Preparation 100

N-[1-Methyl-1-(6-trifluoromethyl-pyridin-3-yl)-ethyl]-acetamide

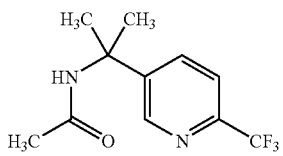

Add acetonitrile (67.4 L; 53.0 kg) to a reaction vessel containing 2-(6-trifluoromethyl-pyridin-3-yl)-propan-2-ol (52 moles; 12.8 kg) and cool to 0-5° C. Add concentrated sulfuric acid (372 moles; 19.8 L; 36.5 kg) slowly, maintaining the internal reaction temperature between 0-15° C. Heat the solution to 25-30° C. for 24 hours, and observe the completion of the reaction by HPLC. Cool the mixture to 0° C. while stirring and add water (95.0 L; 95.0 kg). Add a solution of aqueous ammonia (57.5 kg) to adjust the solution pH to 8.0-9.0, and then add tert-butyl methyl ether (81.1 L; 60.0 kg). Separate the lower aqueous layer, concentrate the organic layer to approximately 3 volumes, and cool the contents of the reaction to −5-0° C. Filter the resultant solids and dry under vacuum until constant weight and collect (13.4 kg; 87.3%, based on HPLC) of the titled compound as a pale yellow solid in 81.8% purity. $^1$H NMR (DMSO-$d_6$, 500 MHz): δ 8.68 (d, 1 H, J=2 Hz), 8.30 (s, 1 H), 7.92 (dd, 1 H, J=2.5, 8.5 Hz), 7.79 (d, 1 H, J=5.8 Hz), 1.82 (s, 3 H), 1.56 (s, 6 H).

Preparation 101

1-Methyl-1-(6-trifluoromethyl-pyridin-3-yl)-ethylamine

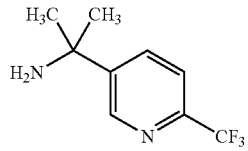

Heat a mixture of N-[1-Methyl-1-(6-trifluoromethyl-pyridin-3-yl)-ethyl]-acetamide (93.5 moles, 19.1 kg), concentrated hydrochloric acid (805.9 moles; 66.2 L; 79.4 kg), and water (79.4 L; 79.4 kg) to 95-100° C. with stirring under nitrogen for 24 hours. Cool the reaction mixture to 20-35° C. and observe completion of the reaction by HPLC. Cool the reaction vessel to 10-20° C. and add tert-butyl methyl ether (105.4 L; 78.0 kg). Separate the phases, and discard the organic layer. Add 15% sodium hydroxide (910.9 moles; 205 L; 242.9 kg) to the aqueous phase and observe a pH of 9.5-10.5. Extract the aqueous layer with ethyl acetate (3×89 mL; 3×80.0 kg), combine the organic layers, and discard the aqueous phase. Concentrate the solution to approximately 2 volumes, add tert-butyl methyl ether (174 L; 129.1 kg), and concentrate the solution to approximately 2 volumes. Dilute the reaction vessel with n-heptane (168 L; 115.0 kg), concentrate the solution to approximately 2 volumes, and dilute with additional n-heptane (30 L, 20.7 kg). Cool the contents of the reaction mixture to 0-5° C. and stir the mixture for 2 hours at 0-5° C. Filter and dry the resultant solids under vacuum at 35-45° C. to afford the titled compound (14.19 kg; 74.3%, based on HPLC) as a 97.9% pure tan powder.

Preparation 102

1-Methyl-1-(6-trifluoromethyl-pyridin-3-yl)-ethylamine; compound with toluene-4-sulfonic acid

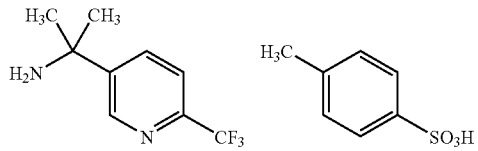

Add a solution of 1-Methyl-1-(6-trifluoromethyl-pyridin-3-yl)-ethylamine (280 g, 1.37 moles) in methyl t-butyl ether (1.4 L) to a solution of p-toluenesulfonic acid monohydrate (212.5 g, 1.23 moles) in tetrahydrofuran (980 mL). Observe a pH of 2.0 and an exotherm to 28° C. Cool to 18° C. and filter solids. Rinse filter cake with methyl t-butyl ether (1.4 L). Vacuum dry the filter cake at ambient temperature and collect 408 g (79%) of the titled compound as a white solid. $^1$H NMR (DMSO-$d_6$, 500 MHz): δ 8.94 (d, 1H, J=2.5), 8.53 (br s, 3H), 8.2 (dd, 1H, J=5.5, 8), 8.02 (d, 1H, J=8), 7.46 (d, 2H, J=8), 7.10 (d, 2H, J=7.5), 2.27 (s, 3H), 1.68 (s, 6H).

Preparation 103

1-Methyl-1-(6-trifluoromethyl-pyridin-3-yl)-ethylamine

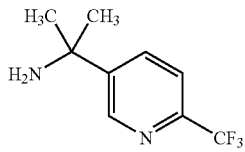

Weigh into 5-L 3-neck flask 1-Methyl-1-(6-trifluoromethyl-pyridin-3-yl)-ethylamine; compound with toluene-4-sulfonic acid (990 g, 2.63 moles). Add methyl t-butyl ether (2.48 L) to form a suspension that is cooled by an ice-bath. Add a 5 M solution of sodium hydroxide (578.64 mL, 2.89 moles) to afford a biphasic mixture at pH 12.2. Separate the phases and extract the organic phase with water (125 mL). Remove the organic phase and concentrate under reduced pressure to afford a residue (200 g). Extract the aqueous phase with a mixture of methyl t-butyl ether (990 mL) and tetrahydrofuran (1.32 L). Separate the organic phase and concentrate under reduced pressure to afford another residue (200 g). Observe that the aqueous phase is pH 10.1 and add 5N NaOH (157.8 mL, 0.789 mol) to give pH 13. Extract the aqueous phase with dichloromethane (1.32 L). Separate the phases and concentrate the organic phase to a third residue. Combine the three residues of amine, suspend in heptane (1 L) with mixing, and concentrate the suspension to afford 427 g (79.5%) of the purified titled compound as a white crystalline solid. $^1$H NMR (CDCl$_3$, 500 MHz): δ 8.91 (d, 1H, J=2.5), 8.05 (dd, 1H, J=2, 8), 7.64 (d, 1H, J=8.5), 1.68 (br s, 2H), 1.55 (s, 6H).

Preparation 104

3-Ethyl-benzaldehyde

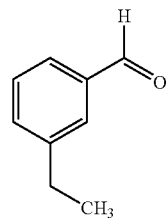

Add a 1 M solution of diisobutylaluminum hydride in toluene (76 mmol) dropwise to a solution of m-ethylbenzonitrile (38 mmol) in toluene (50 mL) under nitrogen in a dry ice-acetone bath. Stir for 30 minutes then add acetic acid (20 mL) dropwise followed by water (100 mL). Stir the reaction for 2 hours. Separate the layers and extract the aqueous with toluene. Dry the combined organic layers over sodium sulfate, and evaporate to give the title compound (4.5 g, 88% yield). ¹HNMR (400.43 MHz, CDCl₃): δ 9.97 (s, 1H), 7.69-7.66 (m, 2H), 7.46-7.40 (m, 2H), 2.71 (q, J=7.6 Hz, 2H), 1.25 (t, J=7.5 Hz, 3H).

Preparation 105

3-(1,1-Difluoro-ethyl)-benzoic acid ethyl ester

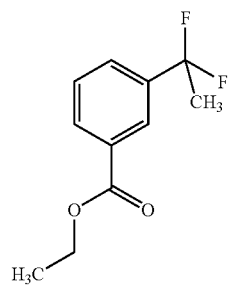

Dissolve ethyl 3-acetylbenzoate (5.2 mmol) in dichloromethane (13 mL) in a polypropylene tube. Add (bis(2-methoxyethyl)amino sulfur trifluoride (Deoxofluor) (10.4 mmol) and ethanol (15 ul). Purge with nitrogen, seal the tube, and heat at 60° C. for 18 hours. Add additional Deoxofluor (10.4 mmol) and heat for an additional 24 hours. Pour the cooled reaction into 5% aqueous sodium bicarbonate, extract with dichloromethane, dry the combined organic extracts over sodium sulfate, filter and evaporate. Purify over silica (40 g) eluting with 1:1 dichloromethane:hexane collecting the first eluting material. Evaporate to give the title compound as a clear colorless liquid in 68% yield. ¹HNMR (400.43 MHz, CDCl₃): δ 8.15 (s, 1H), 8.08 (d, J=7.9 Hz, 1H), 7.67 (d, J=7.9 Hz, 1H), 7.48 (t, J=8.1 Hz, 1H), 4.37 (q, J=7.2 Hz, 2H), 1.96-1.87 (m, 3H), 1.38 (t, J=7.0 Hz, 3H).

Preparation 106

[3-(1,1-Difluoro-ethyl)-phenyl]-methanol

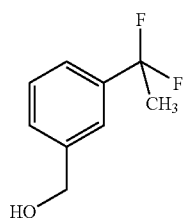

Add a solution of 3-(1,1-Difluoro-ethyl)-benzoic acid ethyl ester (3.57 mmol) in THF (5 mL) dropwise to a 1M solution of lithium aluminum hydride in THF (4.3 mL) at room temperature. Stir for 20 minutes then add ice followed by a mixture of concentrated sulfuric acid and ice (approximately 1:1 v:v). Extract with ethyl ether, dry the organic extracts over sodium sulfate, filter, and evaporate to give the title compound in 97% yield. GCMS MW 172 (M). ¹H NMR (400.43 MHz, CDCl₃): δ 7.49 (s, 1H), 7.41-7.39 (m, 3H), 4.70 (s, 2H), 1.94-1.85 (m, 3H).

Preparation 107

3-(1,1-Difluoro-ethyl)-benzaldehyde

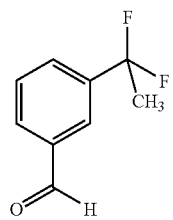

Add a solution of [3-(1,1-Difluoro-ethyl)-phenyl]-methanol (3.47 mmol) in dichloromethane (10.5 mL) dropwise to a suspension of 3,3,3-triacetoxy-3-iodophthalide (3.64 mmol) in dichloromethane (10.5 mL) at room temperature. Stir for 30 minutes. Add diethyl ether (10 mL) and 5% aqueous sodium bicarbonate (10 mL) containing sodium thiosulfate (3 g). Mix well for 20 minutes. Separate the layers, and extract the aqueous with ethyl ether. Combine the organic layers, wash with brine, dry over sodium sulfate, filter, and evaporate to give a yellow solid. Purify over silica (40 g) eluting with 0 to 50% dichloromethane in hexanes. Evaporate until most solvent is removed being careful not to drive off the volatile product. Dry additionally by blowing a nitrogen stream over the product to give the title compound in 70% yield. ¹HNMR (400.43 MHz, CDCl₃): δ 10.03 (s, 1H), 8.00 (s, 1H), 7.92 (d, J=7.5 Hz, 1H), 7.75 (d, J=7.0 Hz, 1H), 7.59 (t, J=7.7 Hz, 1H), 1.98-1.89 (m, 3H).

Preparation 108

3-Cyclopropoxybenzonitrile

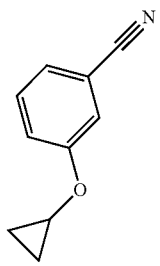

Irradiate (200 C, ~6 W [150 W max.], ~25 psi) a solution of 3-cyanophenol (9.5 g, 80 mmol), cyclopropyl bromide (8.0 mL; 100 mmol), and 1,8-diazabicyclo[5.4.0]undec-7-ene (18 mL, 120 mmol) divided equally into five 10-mL tubes for 15 min. with stirring and cooling. After cooling, take the dark reaction mixtures together in water (200 mL) and extracted with ether (200 mL). Wash the organic layer with 0.2 M aq NaOH (40 mL, salted), 0.2 M aq HCl (100 mL, salted), and water (100 mL, salted). Dry the organic layer (Na₂SO₄) and rotary evaporate (30° C.) yielding 3-cyclopropoxybenzonitrile (4.56 g, 28.65 mmol, 36% yield) as a dark brown liquid. GCMS: 4.20 min.; EIMS m/z 159.

Preparation 109

3-Cyclopropoxybenzaldehyde

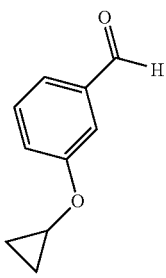

Add diisobutylaluminum hydride (1.0 M in dichloromethane; 47 mL, 47 mmol) over a period of 5 min. to a solution of 3-cyclopropoxybenzonitrile (6.45 g, 39.3 mmol) in anhydrous dichloromethane (200 mL) cooled in an isopropanol/dry ice bath (−78° C.). Remove the bath and allow the reaction solution to warm. After 1 hour (18° C.), dilute the reaction solution with ether (20 mL) and cool to 5° C. in an ice bath. Add water (2 mL), followed by 5 M NaOH (2 mL), and then more water (5 mL). Remove the ice bath and stir the reaction mixture at 20° C. for 15 min. Add anhydrous MgSO$_4$ and stir the reaction mixture for 15 min. Filter the mixture through diatomaceous earth and rotary evaporate (30° C.) the filtrate giving crude 3-cyclopropoxybenzaldehyde (6.33 g, 39 mmol, 99% yield) as an orange-yellow oil. GCMS: EIMS m/z 162.

Preparation 110

4-(3-Fluoro-phenyl)-N-(4-trifluoromethoxy-phenyl)-4-oxo-butyramide

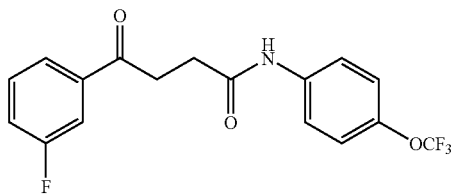

Stir 4-(3-fluoro-phenyl)-4-oxo-butyric acid [C.A. 69797-46-2] (J. Med. Chem. (1983) 26 381) (1.96 g, 10 mmol), 4-trifluoromethoxyaniline (1.77 g, 10 mmol) and O-(1H-benzotriazol-1-yl)-N,N,N',N'-tetramethyluronium tetrafluoroborate (TBTU) (3.5 g, 11 mmol) in dimethylformamide (30 mL). Add triethylamine (2.02 g, 20 mmol). Stir at room temperature for 48 hours. Pour into dilute aqueous HCl (250 mL) and extract into ethyl acetate. Wash the organic phase three times with water, dry over anhydrous magnesium sulfate, evaporate and purify on a silica gel column (dichloromethane-ethyl acetate) to give the titled compound (3.13 g, 88% yield) MS (m/z): 356 (M+1).

Preparation 111

(±)-4-(3-Fluoro-phenyl)-N-(4-trifluoromethoxy-phenyl)-4-hydroxy-butyramide

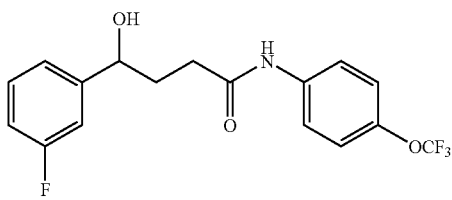

Stir 4-(3-fluoro-phenyl)-N-(4-trifluoromethoxy-phenyl)-4-oxo-butyramide (3.0 g, 8.5 mmol) in ethanol (70 mL) at room temperature. Add sodium borohydride (650 mg, 17.2 mmol) portionwise and stir at room temperature until TLC indicates that no starting material remains. Add acetone to quench excess borohydride, concentrate the reaction mixture under reduced pressure, redissolve in ethyl acetate and wash with brine. Dry over anhydrous magnesium sulfate, evaporate under reduced pressure to give the titled compound (2.0 g, 67% yield) MS (m/z): 358(M+1).

Preparation 112

(R)-5-(3-Fluoro-phenyl)-1-(4-trifluoromethoxy-phenyl)-pyrrolidin-2-one

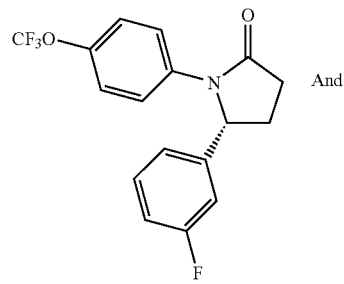

And

Preparation 113

(S)-5-(3-Fluoro-phenyl)-1-(4-trifluoromethoxy-phenyl)-pyrrolidin-2-one

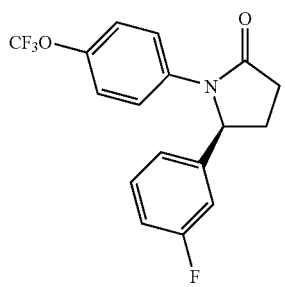

Stir 4-(3-fluoro-phenyl)-N-(4-trifluoromethoxy-phenyl)-4-hydroxy-butyramide (2.45 g, 6.86 mmol) and p-toluenesulfonyl chloride (1.63 g, 8.60 mmol) in dry tetrahydrofuran (30 mL) under nitrogen. Cool to −40° C. and slowly add potassium t-butoxide (1M in tetrahydrofuran) (17.2 mL, 17.2 mmol). Allow to warm slowly to room temperature and stir for 2 hours. Add aqueous NH₄Cl solution and extract with ethyl acetate, wash with brine and dry over anhydrous magnesium sulfate. Evaporate and purify on a silica gel column (dichloromethane-ethyl acetate) to give (±)-5-(3-fluoro-phenyl)-1-(4-trifluoromethoxy-phenyl)-pyrrolidin-2-one (1.9 g, 82% yield) MS (m/z): 340 (M+1).

Instrumentation

Perform Supercritical Fluid Chromatography (SFC) analysis on a Berger Minigram system configured with 6-way column and solvent switching. Perform SFC purification on a Berger Multigram II system. Equip both systems with a Knauer variable wavelength UV detector supplied by Mettler-Toledo AutoChem (Leicester, UK). Deliver liquid CO₂ to the laboratory by a Berger GDS-3000 system supplied also by Mettler-Toledo AutoChem.

Separate the racemic mixture by Supercritical Fluid Chromatography on an ADH column eluting with 30% methanol/propan-2-amine in supercritical carbon dioxide to give the two enantiomers.

(R)-5-(3-Fluoro-phenyl)-1-(4-trifluoromethoxy-phenyl)-pyrrolidin-2-one-891 mg
(S)-5-(3-Fluoro-phenyl)-1-(4-trifluoromethoxy-phenyl)-pyrrolidin-2-one-889 mg Preparation 114

(5R)-3-(4-Chlorobenzoyl)-5-(3-fluoro-phenyl)-1-(4-trifluoromethoxy-phenyl)-pyrrolidin-2-one

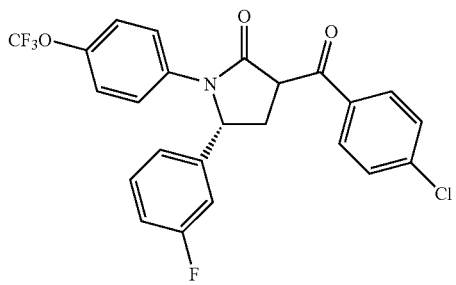

Add (R)-5-(3-fluoro-phenyl)-1-(4-trifluoromethoxy-phenyl)-pyrrolidin-2-one (0.89 g, 2.63 mmol) to a suspension of sodium hydride (0.61 g, 15.36 mmol) in dry toluene (40 mL) and stir at room temperature under nitrogen. Add methanol (0.29 mL, approx. 16 mmol) followed by methyl p-chlorobenzoate (1.2 g, 7.0 mmol). Heat under reflux overnight. Cool, add aqueous NH₄Cl solution, extract with ethyl acetate. Collect the organic phase, dry over anhydrous magnesium sulfate, evaporate and purify on a silica gel column (isohexane-ethyl acetate) to give the titled compound (1.1 g, 88% yield) MS (m/z): 478 (M+1).

Prepare the following Compounds essentially by the method of Preparation 114.

TABLE 9

| Prep N° | Compound, Name | Physical Data, Yield |
|---|---|---|
| 115 | 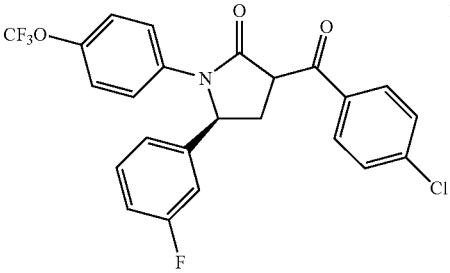<br>(5S)-3-(4-Chlorobenzoyl)-5-(3-fluoro-phenyl)-1-(4-trifluoromethoxy-phenyl)-pyrrolidin-2-one | MS (m/z): 478 (M + 1). Yield 94% |

Preparation 116

(5R)-3-Diazo-5-(3-fluoro-phenyl)-1-(4-trifluoromethoxy-phenyl)-pyrrolidin-2-one

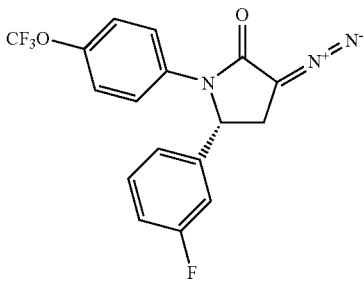

Dissolve sodium azide (2.6 g, 40 mmol) and tetrabutylammonium bromide (260 mg, 0.8 mmol) in 2N sodium hydroxide solution (50 mL), add isohexane (50 mL) and stir while cooling in an ice-water bath. Add trifluoromethanesulfonic anhydride (2.0 mL, approx 12 mmol) dropwise, stir for 10 minutes with cooling. Dissolve (5R)-(3-(4-chlorobenzoyl-5-(3-fluoro-phenyl)-1-(4-trifluoromethoxy-phenyl)-pyrrolidin-2-one (1.1 g, 2.3 mmol) in acetonitrile (30 mL), add to the reaction mixture and stir vigorously for 30 minutes. Dilute the reaction mixture with ethyl acetate (150 mL) and wash with brine. Collect the organic phase, dry over anhydrous magnesium sulfate, evaporate and purify on a silica gel column (isohexane-ethyl acetate) to give the titled compound (590 mg, 70% yield) MS (m/z): 366 (M+1).

Prepare the following Compounds essentially by the method of Preparation 116.

TABLE 10

| Prep Nº | Compound, Name | Physical Data, Yield |
|---|---|---|
| 117 | 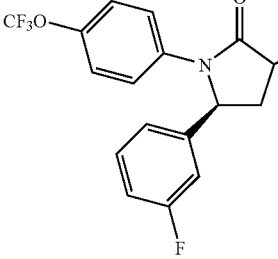<br>(5S)-3-Diazo-5-(3-fluoro-phenyl)-1-(4-trifluoromethoxy-phenyl)-pyrrolidin-2-one | MS (m/z): 366 (M + 1). Yield 73% |

EXAMPLE 1

(3R,5R)-3-[1-Methyl-1-(6-trifluoromethyl-pyridin-3-yl)-ethylamino]-5-(m-tolyl)-1-(4-trifluoromethoxy-phenyl)-pyrrolidin-2-one tosylate

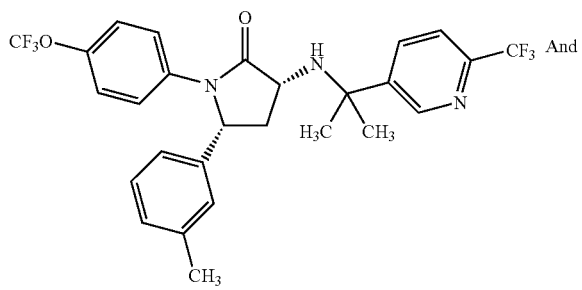

EXAMPLE 2

(3S,5S)-3-[1-Methyl-1-(6-trifluoromethyl-pyridin-3-yl)-ethylamino]-5-(m-tolyl)-1-(4-trifluoromethoxy-phenyl)-pyrrolidin-2-one tosylate

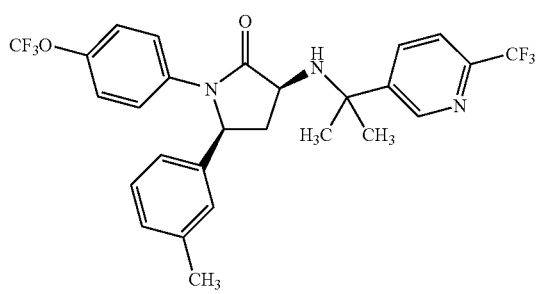

Dissolve (±)-3-[1-methyl-1-(6-trifluoromethyl-pyridin-3-yl)-ethylamino]-5-(m-tolyl)-1-(4-trifluoro methoxy-phenyl)-1,5-dihydro-pyrrol-2-one (2.19 g; 4.09 mmol) in acetic acid (15 mL) and add sodium cyanoborohydride (0.77 g, 12.27 mmol). Stir for 12 hours at ambient temperature. Pour into ice/water (50 mL) and extract with ethyl acetate (50 mL×2). Wash the organic phase with saturated sodium bicarbonate (20 mL×3), brine (20 mL), dry over magnesium sulfate and evaporate in vacuo to an oil. Purify on an SCX-2 ion exchange resin cartridge (eluent methanol followed 2M $NH_3$ in methanol) and then by chromatography on a silica gel column (eluent ethyl acetate/iso-hexane) to give the titled compound as a racemic mixture (1.60 g, 73%). MS (m/z): 538.2 (M+1).

Perform Supercritical Fluid Chromatography (SFC) analysis on a Berger Minigram system configured with 6-way column and solvent switching. Perform SFC purification on a Berger Multigram II system. Equip both systems with a Knauer variable wavelength UV detector (Mettler-Toledo AutoChem (Leicester, UK)). Liquid $CO_2$ is delivered to the laboratory by a Berger GDS-3000 system supplied also by Mettler-Toledo AutoChem.

Separate the racemic mixture by Supercritical Fluid Chromatography on an ADH column eluted with 30% methanol/propan-2-amine in supercritical carbon dioxide to give (3R, 5R)-3-[1-methyl-1-(6-trifluoromethyl-pyridin-3-yl)-ethylamino]-5-(m-tolyl)-1-(4-trifluoromethoxy-phenyl)-pyrrolidin-2-one (0.62 g, 47.6%), eluted with 10% isopropyl alcohol/propan-2-amine in supercritical carbon dioxide, retention time 0.65 min., MS (m/z): 538.2 (M+1). Prepare p-Toluene sulfonic salt with p-toluene sulfonic acid (219 mg, 1 eq) in isopropyl alcohol and filter the crystals. $^1$H NMR (400.13 MHz, MeOD): δ 9.08 (d, J=2.0 Hz, 1H), 8.41 (dd, J=2.2, 8.6 Hz, 1H), 7.94 (d, J=8.3 Hz, 1H), 7.72 (d, J=8.3 Hz, 2H), 7.41-7.37 (m, 2H), 7.23-7.05 (m, 8H), 5.21 (dd, J=6.1, 9.3 Hz, 1H), 4.36 (dd, J=8.6, 11.5 Hz, 1H), 2.83-2.76 (m, 1H), 2.38 (s, 3H), 2.26 (s, 3H), 2.22-2.11 (m, 1H), 2.01 (d, J=1.5 Hz, 6H), and elute (3S,5S)-3-[1-methyl-1-(6-trifluoromethyl-pyridin-3-yl)-ethylamino]-5-(m-tolyl)-1-(4-trifluoromethoxy-phenyl)-pyrrolidin-2-one (0.58 g, 45.1%), with 10% isopropyl alcohol/propan-2-amine in supercritical carbon dioxide, retention time 1.03 min., MS (m/z): 538.2 (M+1), Prepare p-Toluene sulfonic salt with p-toluene sulfonic acid (205 mg, eq) in isopropyl alcohol and filter the crystals. $^1$H NMR (400.13 MHz, MeOD): δ 9.08 (d, J=2.2 Hz, 1H), 8.40 (dd, J=2.2, 8.3 Hz, 1H), 7.95 (d, J=8.3 Hz, 1H), 7.72 (d, J=8.1 Hz, 2H), 7.40-7.37 (m, 2H), 7.23 (d, J=8.1 Hz, 2H), 7.18-7.14 (m, 3H), 7.09-7.02 (m, 3H), 5.21 (dd, J=6.1, 9.3 Hz, 1H), 4.35 (dd, J=8.6, 11.2 Hz, 1H), 2.84-2.77 (m, 1H), 2.38 (s, 3H), 2.26 (s, 3H), 2.22-2.10 (m, 1H), 2.01 (d, J=1.7 Hz, 6H).

Prepare the following Compounds essentially by the method of Example 1 and Example 2.

TABLE 11

| Ex N° | Compound, Name and Physical data | Yield and Comment |
|---|---|---|
| 3 | 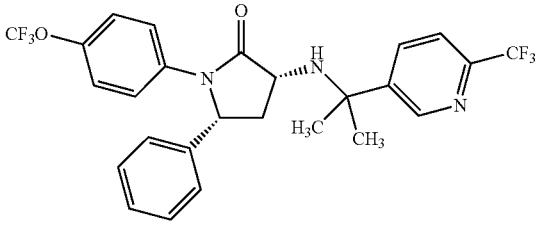<br>(3R,5R)-3-[1-Methyl-1-(6-trifluoromethyl-pyridin-3-yl)-ethylamino]-5-phenyl-1-(4-trifluoromethoxy-phenyl)-pyrrolidin-2-one tosylate<br>MS (m/z): 524.1 (M + 1).<br>$^1$H NMR (400.13 MHz, MeOD): δ 9.08 (d, J = 2.0 Hz, 1H), 8.41 (dd, J = 2.1, 8.4 Hz, 1H), 7.95 (d, J = 8.6 Hz, 1H), 7.72 (d, J = 8.1 Hz, 2H), 7.40-7.37 (m, 2H), 7.28-7.22 (m, 7H), 7.15 (d, J = 8.8 Hz, 2H), 5.26 (dd, J = 6.1, 9.3 Hz, 1H), 4.37 (dd, J = 8.6, 11.2 Hz, 1H), 2.85-2.78 (m, 1H), 2.38 (s, 3H), 2.20-2.11 (m, 1H), 2.01 (s, 6H). | Yield 31.4%<br>Elute with 8% methanol/propan-2-amine in supercritical carbon dioxide retention time 0.89 min. |
| 4 | 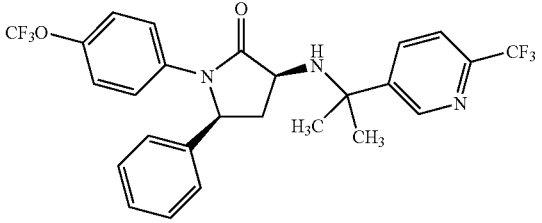<br>(3S,5S)-3-[1-Methyl-1-(6-trifluoromethyl-pyridin-3-yl)-ethylamino]-5-phenyl-1-(4-trifluoromethoxy-phenyl)-pyrrolidin-2-one tosylate<br>MS (m/z): 524.1 (M + 1).<br>$^1$H NMR (400.13 MHz, MeOD): δ 9.08 (d, J = 2.0 Hz, 1H), 8.41 (dd, J = 2.1, 8.4 Hz, 1H), 7.95 (d, J = 8.6 Hz, 1H), 7.72 (d, J = 8.1 Hz, 2H), 7.39 (d, J = 9.0 Hz, 2H), 7.28-7.22 (m, 7H), 7.15 (d, J = 8.6 Hz, 2H), 5.26 (dd, J = 6.1, 9.3 Hz, 1H), 4.36 (dd, J = 8.6, 11.2 Hz, 1H), 2.86-2.79 (m, 1H), 2.38 (s, 3H), 2.19-2.11 (m, 1H), 2.01 (s, 6H). | Yield 31.2%.<br>Elute with 8% methanol/propan-2-amine in supercritical carbon dioxide, retention time 1.47 min. |
| 5 | 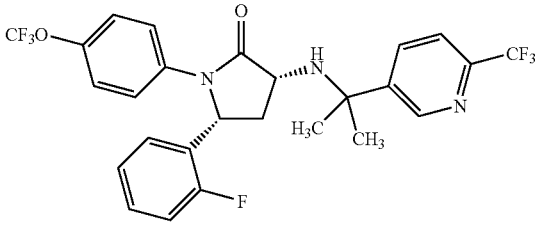<br>(3R,5R)-3-[1-Methyl-1-(6-trifluoromethyl-pyridin-3-yl)-ethylamino]-5-(2-fluoro-phenyl)-1-(4-trifluoromethoxy-phenyl)-pyrrolidin-2-one tosylate<br>MS (m/z): 542.1 (M + 1).<br>$^1$H NMR (400.13 MHz, MeOD): δ 9.09 (d, J = 2.2 Hz, 1H), 8.41 (dd, J = 2.2, 8.3 Hz, 1H), 7.95 (d, J = 8.3 Hz, 1H), 7.72 (d, J = 8.1 Hz, 2H), 7.40-7.37 (m, 2H), 7.33-7.27 (m, 2H), 7.23 (d, J = 7.8 Hz, 2H), 7.18 (d, J = 8.3 Hz, 2H), 7.12-7.04 (m, 2H), 5.54 (dd, J = 6.4, 9.3 Hz, 1H), 4.36 (dd, J = 8.8, 11.2 Hz, 1H), 2.90-2.83 (m, 1H), 2.38 (s, 3H), 2.31 (td, J = 11.7, 9.6 Hz, 1H), 2.01 (d, J = 2.4 Hz, 6H). | Yield 29.5%.<br>Elute with 10% ethanol/propan-2-amine in supercritical carbon dioxide, retention time 0.72 min. |

TABLE 11-continued

| Ex N° | Compound, Name and Physical data | Yield and Comment |
|---|---|---|
| 6 | (3S,5S)-3-[1-Methyl-1-(6-trifluoromethyl-pyridin-3-yl)-ethylamino]-5-(2-fluoro-phenyl)-1-(4-trifluoromethoxy-phenyl)-pyrrolidin-2-one tosylate<br>MS (m/z): 542.1 (M + 1).<br>$^1$H NMR (400.13 MHz, MeOD): δ 9.09 (d, J = 2.2 Hz, 1H), 8.41 (dd, J = 2.3, 8.4 Hz, 1H), 7.95 (d, J = 8.3 Hz, 1H), 7.72 (d, J = 8.3 Hz, 2H), 7.41-7.37 (m, 2H), 7.33-7.27 (m, 2H), 7.23 (d, J = 7.8 Hz, 2H), 7.18 (d, J = 8.3 Hz, 2H), 7.11-7.06 (m, 2H), 5.55 (dd, J = 6.4, 9.0 Hz, 1H), 4.36 (dd, J = 8.6, 11.2 Hz, 1H), 2.90-2.83 (m, 1H), 2.38 (s, 3H), 2.31 (td, J = 11.8, 9.5 Hz, 1H), 2.01 (d, J = 2.7 Hz, 6H). | Yield 29.9%.<br>Elute with 10% ethanol/propan-2-amine in supercritical carbon dioxide, retention time 0.85 min. |
| 7 | (3R,5R)-3-[1-Methyl-1-(6-trifluoromethyl-pyridin-3-yl)-ethylamino]-5-(4-fluoro-phenyl)-1-(4-trifluoromethoxy-phenyl)-pyrrolidin-2-one tosylate<br>MS (m/z): 542.1 (M + 1)<br>$^1$H NMR (400.13 MHz, MeOD): δ 9.09 (d, J = 2.2 Hz, 1H), 8.41 (dd, J = 2.2, 8.3 Hz, 1H), 7.95 (d, J = 8.3 Hz, 1H), 7.73 (d, J = 8.1 Hz, 2H), 7.39-7.35 (m, 2H), 7.31-7.28 (m, 2H), 7.24 (d, J = 8.1 Hz, 2H), 7.16 (d, J = 8.3 Hz, 2H), 7.03-6.98 (m, 2H), 5.26 (dd, J = 6.1, 9.3 Hz, 1H), 4.36 (dd, J = 8.4, 11.4 Hz, 1H), 2.85-2.78 (m, 1H), 2.38 (s, 3H), 2.15 (td, J = 11.9, 9.6 Hz, 1H), 2.01 (d, J = 2.9 Hz, 6H). | Yield 21%<br>Elute with 10% isopropyl alcohol/propan-2-amine in supercritical carbon dioxide, retention time 1.38 min. |
| 8 | (3S,5S)-3-[1-Methyl-1-(6-trifluoromethyl-pyridin-3-yl)-ethylamino]-5-(4-fluoro-phenyl)-1-(4-trifluoromethoxy-phenyl)-pyrrolidin-2-one tosylate<br>MS (m/z): 542.1 (M + 1).<br>$^1$H NMR (400.13 MHz, MeOD): δ 9.09 (d, J = 2.2 Hz, 1H), 8.41 (dd, J = 2.2, 8.3 Hz, 1H), 7.95 (d, J = 8.3 Hz, 1H), 7.73 (d, J = 8.1 Hz, 2H), 7.39-7.36 (m, 2H), 7.31-7.27 (m, 2H), 7.24 (d, J = 7.8 Hz, 2H), 7.17 (d, J = 8.3 Hz, 2H), 7.04-6.99 (m, 2H), 5.26 (dd, J = 6.1, 9.5 Hz, 1H), 4.36 (dd, J = 8.4, 11.4 Hz, 1H), 2.86-2.79 (m, 1H), 2.38 (s, 3H), 2.22-2.10 (m, 1H), 2.01 (d, J = 2.9 Hz, 6H). | Yield 26%<br>Elute with 10% isopropyl alcohol/propan-2-amine in supercritical carbon dioxide, retention time 3.06 min. |

TABLE 11-continued

| Ex N° | Compound, Name and Physical data | Yield and Comment |
|---|---|---|
| 9 | 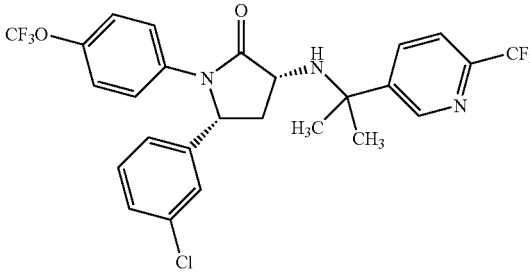<br>(3R,5R)-3-[1-Methyl-1-(6-trifluoromethyl-pyridin-3-yl)-ethylamino]-5-(3-chloro-phenyl)-1-(4-trifluoromethoxy-phenyl)-pyrrolidin-2-one tosylate<br>MS (m/z): 558.1 (M + 1)<br>$^1$H NMR (400.13 MHz, MeOD): δ 9.09 (s, 1H), 8.43-8.41 (m, 1H), 7.93 (d, J = 8.3 Hz, 1H), 7.72 (d, J = 8.1 Hz, 2H), 7.39 (d, J = 9.0 Hz, 2H), 7.32 (s, 1H), 7.26-7.16 (m, 7H), 5.27 (dd, J = 6.1, 9.0 Hz, 1H), 4.37 (dd, J = 8.7, 11.1 Hz, 1H), 2.88-2.81 (m, 1H), 2.37 (s, 3H), 2.21-2.07 (m, 1H), 2.01 (d, J = 1.2 Hz, 6H). | Yield 39.7%<br>Elute with 20% isopropyl alcohol/propan-2-amine in supercritical carbon dioxide, retention time 0.62 min. |
| 10 | 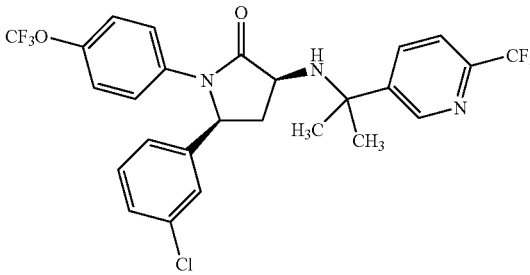<br>(3S,5S)-3-[1-Methyl-1-(6-trifluoromethyl-pyridin-3-yl)-ethylamino]-5-(3-chloro-phenyl)-1-(4-trifluoromethoxy-phenyl)-pyrrolidin-2-one tosylate<br>MS (m/z): 558.1 (M + 1).<br>$^1$H NMR (400.13 MHz, MeOD): δ 9.09 (d, J = 1.7 Hz, 1H), 8.41 (dd, J = 2.0, 8.3 Hz, 1H), 7.94 (d, J = 8.3 Hz, 1H), 7.72 (d, J = 8.1 Hz, 2H), 7.39 (d, J = 8.8 Hz, 2H), 7.32 (s, 1H), 7.26-7.16 (m, 7H), 5.27 (dd, J = 6.1, 9.3 Hz, 1H), 4.37 (dd, J = 8.8, 11.2 Hz, 1H), 2.89-2.82 (m, 1H), 2.38 (s, 3H), 2.19-2.11 (m, 1H), 2.01 (d, J = 2.0 Hz, 6H). | Yield 42.8%<br>Elute with 20% isopropyl alcohol/propan-2-amine in supercritical carbon dioxide, retention time 0.87 min. |
| 11 | 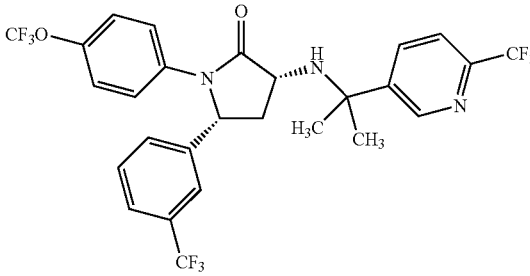<br>(3R,5R)-3-[1-Methyl-1-(6-trifluoromethyl-pyridin-3-yl)-ethylamino]-5-(3-trifluoromethyl-phenyl)-1-(4-trifluoromethoxy-phenyl)-pyrrolidin-2-one tosylate<br>MS (m/z): 542.1 (M + 1).<br>$^1$H NMR (400.13 MHz, MeOD): δ 9.08 (d, J = 2.0 Hz, 1H), 8.39 (dd, J = 2.2, 8.3 Hz, 1H), 7.96 (d, J = 8.3 Hz, 1H), 7.72 (d, J = 8.1 Hz, 2H), 7.59-7.49 (m, 4H), 7.43-7.39 (m, 2H), 7.25-7.18 (m, 4H), 5.51-5.38 (m, 1H), 4.39-4.34 (m, 1H), 2.97-2.90 (m, 1H), 2.38 (s, 3H), 2.16-2.06 (m, 1H), 2.00 (d, J = 3.4 Hz, 6H). | Yield 33.1%<br>Elute with 5% isopropyl alcohol/propan-2-amine in supercritical carbon dioxide, retention time 2.78 min. |

TABLE 11-continued

| Ex N° | Compound, Name and Physical data | Yield and Comment |
|---|---|---|
| 12 | 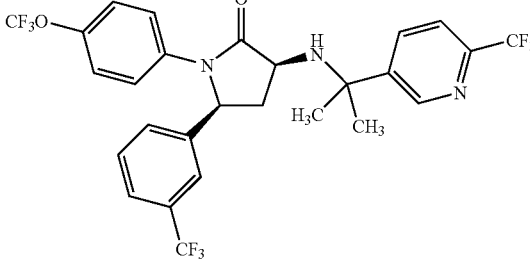<br>(3S,5S)-3-[1-Methyl-1-(6-trifluoromethyl-pyridin-3-yl)-ethylamino]-5-(3-trifluoromethyl-phenyl)-1-(4-trifluoromethoxy-phenyl)-pyrrolidin-2-one tosylate<br>MS (m/z): 542.1 (M + 1).<br>$^1$H NMR (400.13 MHz, MeOD): δ 9.09 (d, J = 1.7 Hz, 1H), 8.41 (dd, J = 2.2, 8.3 Hz, 1H), 7.95 (d, J = 8.3 Hz, 1H), 7.72 (d, J = 8.1 Hz, 2H), 7.59-7.54 (m, 3H), 7.50-7.46 (m, 1H), 7.39 (d, J = 9.0 Hz, 2H), 7.23 (d, J = 7.8 Hz, 2H), 7.17 (d, J = 8.8 Hz, 2H), 5.40 (dd, J = 6.1, 9.3 Hz, 1H), 4.40 (dd, J = 8.6, 11.2 Hz, 1H), 2.94-2.88 (m, 1H), 2.38 (s, 3H), 2.20-2.12 (m, 1H), 2.01 (d, J = 2.7 Hz, 6H). | Yield 33.3%<br>Elute with 5% isopropyl alcohol/propan-2-amine in supercritical carbon dioxide, retention time 1.28 min. |
| 13 | 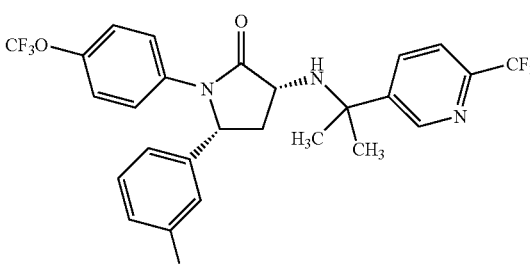<br>(3R,5R)-3-[1-Methyl-1-(6-trifluoromethyl-pyridin-3-yl)-ethylamino]-5-(3-trifluoromethoxy-phenyl)-1-(4-trifluoromethoxy-phenyl)-pyrrolidin-2-one tosylate<br>MS (m/z): 608.1 (M + 1).<br>$^1$H NMR (400.13 MHz, MeOD): δ 9.08 (d, J = 2.2 Hz, 1H), 8.40 (dd, J = 2.3, 8.4 Hz, 1H), 7.96 (d, J = 8.3 Hz, 1H), 7.72 (d, J = 8.1 Hz, 2H), 7.43-7.37 (m, 3H), 7.30 (d, J = 7.8 Hz, 1H), 7.24 (d, J = 7.8 Hz, 2H), 7.19-7.17 (m, 4H), 5.34 (dd, J = 6.1, 9.5 Hz, 1H), 4.37 (dd, J = 8.4, 11.4 Hz, 1H), 2.94-2.87 (m, 1H), 2.38 (s, 3H), 2.11 (td, J = 11.9, 9.6 Hz, 1H), 2.01 (d, J = 2.7 Hz, 6H). | Yield 42.3%<br>Elute with 10% methanol/propan-2-amine in supercritical carbon dioxide, retention time 0.44 min. |
| 14 | 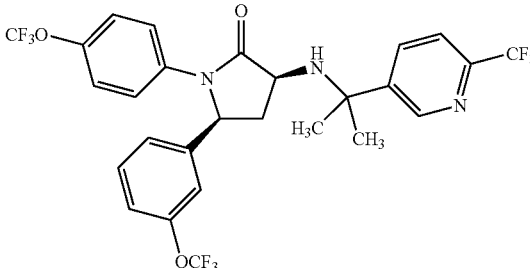<br>(3S,5S)-3-[1-Methyl-1-(6-trifluoromethyl-pyridin-3-yl)-ethylamino]-5-(3-trifluoromethoxy-phenyl)-1-(4-trifluoromethoxy-phenyl)-pyrrolidin-2-one tosylate<br>MS (m/z): 608.1 (M + 1).<br>$^1$H NMR (400.13 MHz, MeOD): δ 9.09 (d, J = 2.0 Hz, 1H), 8.41 (dd, J = 2.2, 8.3 Hz, 1H), 7.95 (d, J = 8.6 Hz, 1H), 7.72 (d, J = 8.3 Hz, 2H), 7.42-7.36 (m, 3H), 7.30 (d, J = 7.8 Hz, 1H), 7.23 (d, J = 8.1 Hz, 2H), 7.18-7.16 (m, 4H), 5.34 (dd, J = 6.1, 9.3 Hz, 1H), 4.38 (dd, J = 8.6, 11.5 Hz, 1H), 2.92-2.86 (m, 1H), 2.38 (s, 3H), 2.14 (td, J = 11.8, 9.6 Hz, 1H), 2.01 (d, J = 2.4 Hz, 6H). | Yield 43.2%<br>Elute with 10% methanol/propan-2-amine in supercritical carbon dioxide, retention time 0.63 min. |

TABLE 11-continued

| Ex N° | Compound, Name and Physical data | Yield and Comment |
|---|---|---|
| 15 | 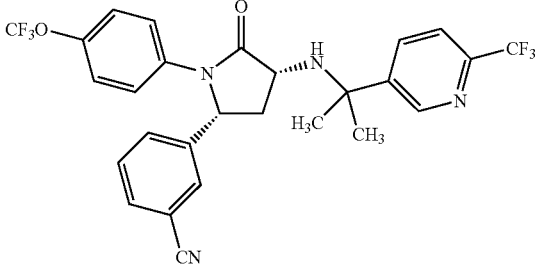<br>(3R,5R)-3-[1-Methyl-1-(6-trifluoromethyl-pyridin-3-yl)-ethylamino]-5-(3-cyano-phenyl)-1-(4-trifluoromethoxy-phenyl)-pyrrolidin-2-one tosylate<br>MS (m/z): 549.1 (M + 1).<br>$^1$H NMR (400.13 MHz, MeOD): δ 9.09 (d, J = 2.2 Hz, 1H), 8.43 (dd, J = 2.2, 8.3 Hz, 1H), 7.94 (d, J = 8.6 Hz, 1H), 7.73 (d, J = 8.3 Hz, 2H), 7.68 (s, 1H), 7.62-7.59 (m, 2H), 7.45 (t, J = 7.8 Hz, 1H), 7.39-7.36 (m, 2H), 7.23 (d, J = 8.1 Hz, 2H), 7.17 (d, J = 8.6 Hz, 2H), 5.35 (dd, J = 6.1, 9.3 Hz, 1H), 4.39 (dd, J = 8.6, 11.2 Hz, 1H), 2.91-2.84 (m, 1H), 2.38 (s, 3H), 2.18 (td, J = 11.7, 9.6 Hz, 1H), 2.02 (d, J = 2.7 Hz, 6H). | Yield 42.5%<br>Elute with 20% ethanol/propan-2-amine in supercritical carbon dioxide, retention time 0.53 min. |
| 16 | 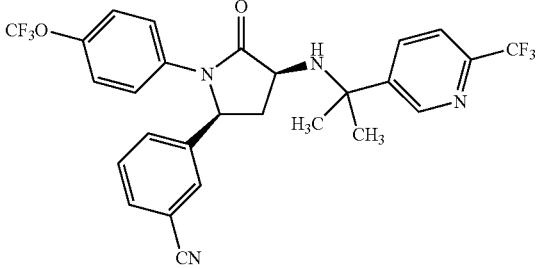<br>(3S,5S)-3-[1-Methyl-1-(6-trifluoromethyl-pyridin-3-yl)-ethylamino]-5-(3-cyano-phenyl)-1-(4-trifluoromethoxy-phenyl)-pyrrolidin-2-one tosylate<br>MS (m/z): 549.1 (M + 1).<br>$^1$H NMR (400.13 MHz, MeOD): δ 8.97 (d, J = 2.2 Hz, 1H), 8.30 (dd, J = 2.3, 8.4 Hz, 1H), 7.82 (d, J = 8.3 Hz, 1H), 7.62-7.56 (m, 3H), 7.50-7.47 (m, 2H), 7.33 (t, J = 7.8 Hz, 1H), 7.27-7.24 (m, 2H), 7.11 (d, J = 8.1 Hz, 2H), 7.05 (d, J = 8.3 Hz, 2H), 5.23 (dd, J = 6.1, 9.3 Hz, 1H), 4.27 (dd, J = 8.6, 11.5 Hz, 1H), 2.79-2.72 (m, 1H), 2.26 (s, 3H), 2.09-2.01 (m, 1H), 1.89 (d, J = 2.9 Hz, 6H). | Yield 43.1%<br>Elute with 20% ethanol/propan-2-amine in supercritical carbon dioxide, retention time 0.68 min. |
| 17 | 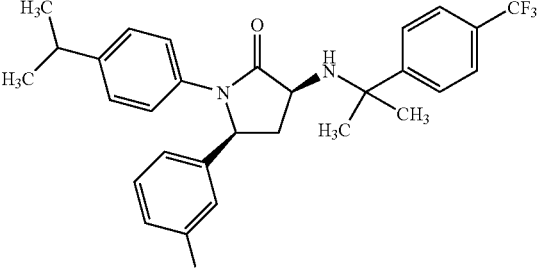<br>(3S,5S)-3-[1-Methyl-1-(6-trifluoromethyl-pyridin-3-yl)-ethylamino]-5-(3-trifluoromethoxy-phenyl)-1-(4-isopropyl-phenyl)-pyrrolidin-2-one<br>MS (m/z): 566 (M + 1). | 39% Yield<br>20% MeOH/CO2<br>0.1% IPAm Chiralcel OD-H 5 mL/min 225 nm: ret.time 0.71 min |

TABLE 11-continued

| Ex N° | Compound, Name and Physical data | Yield and Comment |
|---|---|---|
| 18 | 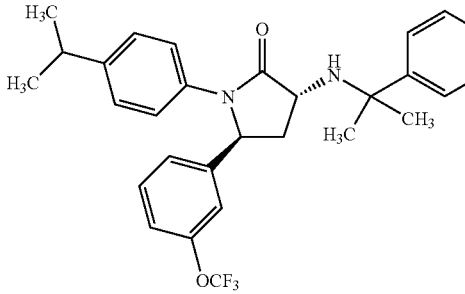<br>(3R,5R)-3-[1-Methyl-1-(6-trifluoromethyl-pyridin-3-yl)-ethylamino]-5-(3-trifluoromethoxy-phenyl)-1-(4-isopropyl-phenyl)-pyrrolidin-2-one<br>MS (m/z): 566 (M + 1). | 36% Yield<br>20% MeOH/CO2<br>0.1% IPAm Chiralcel OD-H 5 mL/min 225 nm: ret.time 1.4 min |
| 19 | 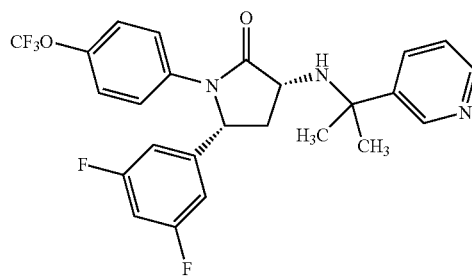<br>Free base<br>(3R,5R)-3-[1-Methyl-1-(6-trifluoromethyl-pyridin-3-yl)-ethylamino]-5-(3,5-difluoro-phenyl)-1-(4-trifluoromethoxy-phenyl)-pyrrolidin-2-one<br>MS (m/z): 560 (M + 1).<br>1H NMR (400.13 MHz, CDCl3): δ 8.85 (d, J = 2.0 Hz, 1H), 8.11 (dd, J = 2.0, 8.3 Hz, 1H), 7.65 (d, J = 8.3 Hz, 1H), 7.32-7.26 (m, 2H), 7.12-7.00 (m, 2H), 6.70-6.64 (m, 3H), 4.92 (dd, J = 5.9, 9.8 Hz, 1H), 3.40 (dd, J = 7.8, 10.8 Hz, 1H), 2.78-2.70 (m, 2H), 1.84-1.76 (m, 1H), 1.59-1.56 (m, 6H). | Yield 33%.<br>Eluted with 15% IPA/propan-2-amine in supercritical carbon dioxide, retention time 0.80 min |
| 20 | 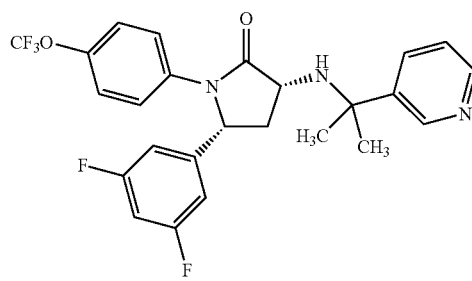<br>(3R,SR)-3-[1-Methyl-1-(6-trifluoromethyl-pyridin-3-yl)-ethylamino]-5-(3,5-difluoro-phenyl)-1-(4-trifluoromethoxy-phenyl)-pyrrolidin-2-one tosylate<br>MS (m/z): 560 (M + 1).<br>1H NMR (400.13 MHz, MeOD): δ 9.07 (d, J = 2.2 Hz, 1H), 8.38 (dd, J = 2.2, 8.3 Hz, 1H), 7.96 (d, J = 8.3 Hz, 1H), 7.72 (d, J = 8.1 Hz, 2H), 7.45-7.42 (m, 2H), 7.24 (t, J = 7.5 Hz, 4H), 6.96-6.88 (m, 3H), 5.29 (dd, J = 6.2, 9.4 Hz, 1H), 4.32-4.24 (m, 1H), 2.94-2.87 (m, 1H), 2.39 (s, 3H), 1.97 (d, J = 3.9 Hz, 7H). | Yield 82%.<br>Eluted with 15% IPA/propan-2-amine in supercritical carbon dioxide, retention time 0.80 min |

TABLE 11-continued

| Ex N° | Compound, Name and Physical data | Yield and Comment |
|---|---|---|
| 21 | 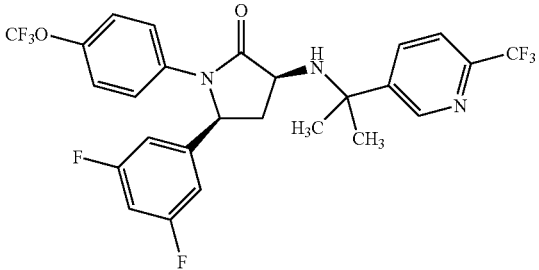<br>(3S, 5S)-3-[1-Methyl-1-(6-trifluoromethyl-pyridin-3-yl)-ethylamino]-5-(3,5-difluoro-phenyl)-1-(4-trifluoromethoxy-phenyl)-pyrrolidin-2-one tosylate<br>MS (m/z): 560 (M + 1).<br>1H NMR (300.07 MHz, MeOD): δ 9.09-9.07 (m, 1H), 8.40-8.34 (m, 1H), 7.97 (d, J = 8.5 Hz, 1H), 7.74-7.72 (m, 2H), 7.46-7.42 (m, 2H), 7.27-7.21 (m, 4H), 6.97-6.91 (m, 3H), 5.38-5.27 (m, 1H), 4.41-4.29 (m, 1H), 2.97-2.92 (m, 1H), 2.39 (s, 3H), 2.06-1.97 (m, 7H). | Yield 90%.<br>Elute with 10% ethanol/propan-2-amine in supercritical carbon dioxide, retention time 0.84 min |
| 22 | 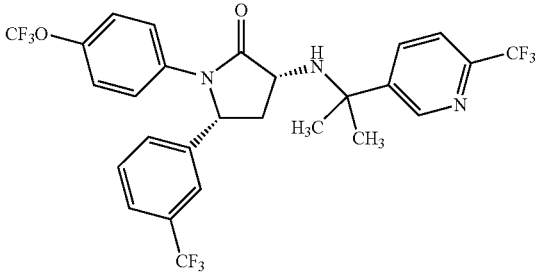<br>Free base<br>(3R,5R)-3-[1-Methyl-1-(6-trifluoromethyl-pyridin-3-yl)-ethylamino]-5-(3-trifluoromethyl-phenyl)-1-(4-trifluoromethoxy-phenyl)-pyrrolidin-2-one<br>MS (m/z): 592 (M + 1).<br>1H NMR (300.07 MHz, CDCl3): δ 8.85 (d, J = 2.3 Hz, 1H), 8.15-8.05 (m, 1H), 7.65 (d, J = 7.9 Hz, 1H), 7.41-7.26 (m, 6H), 7.15-7.06 (m, 2H), 5.01 (dd, J = 6.1, 9.9 Hz, 1H), 3.46-3.40 (m, 1H), 2.92-2.88 (m, 2H), 1.89-1.79 (m, 1H), 1.60-1.52 (m, 6H). | Yield 35%.<br>Eluted with 5% IPA/propan-2-amine in supercritical carbon dioxide, retention time 2.78 min |
| 23 | 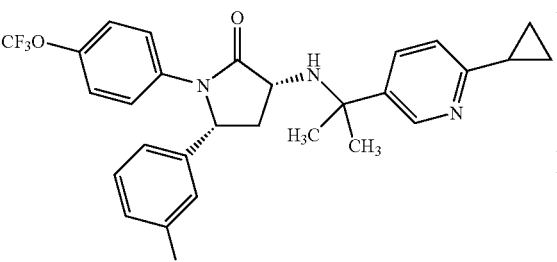<br>(3R,5R)-3-[1-Methyl-1-(6-cyclopropyl-pyridin-3 Y1) ethylamino]-5-(3-cyano-phenyl)-1-(4-trifluoromethoxy-phenyl)-pyrrolidin-2-one dihydrochloride salt<br>¹H NMR (400.13 MHz, MeOD): δ 8.95 (d, J = 2.2 Hz, 1H), 8.81 (dd, J = 2.2, 8.8 Hz, 1H), 7.78-7.63 (m, 4H), 7.52-7.43 (m, 3H), 7.21 (d, J = 8.6 Hz, 2H), 5.44-5.39 (m, 1H), 4.50-4.35 (m, 1H), 3.09-3.03 (m, 1H), 2.45-2.35 (m, 2H), 2.01 (d, J = 12.2 Hz, 6H), 1.56-1.51 (m, 2H), 1.33-1.28 (m, 2H).<br>MS (m/z): 521 (M + 1) | Yield 98%<br>Eluted with 15% isopropyl alcohol/propan-2-amine in supercritical carbon dioxide, retention time 2.85 min |

TABLE 11-continued

| Ex N° | Compound, Name and Physical data | Yield and Comment |
|---|---|---|
| 24 | (3S,5S)-3-[1-Methyl-1-(6-cyclopropyl-pyridin-3-yl)-ethylamino]-5-(3-cyano-phenyl)-1-(4-trifluoromethoxy-phenyl)-pyrrolidin-2-one dihydrochloride salt<br>$^1$H NMR (400.13 MHz, MeOD): δ 8.96 (d, J = 2.0 Hz, 1H), 8.83 (dd, J = 2.1, 8.9 Hz, 1H), 7.79-7.63 (m, 4H), 7.52-7.43 (m, 3H), 7.20 (d, J = 8.6 Hz, 2H), 5.45-5.40 (m, 1H), 4.53-4.48 (m, 1H), 3.10-3.03 (m, 1H), 2.45-2.36 (m, 2H), 2.03 (d, J = 11.7 Hz, 6H), 1.57-1.52 (m, 2H), 1.37-1.29 (m, 2H).<br>MS (m/z): 521 (M + 1). | Yield 99%<br>Eluted with 20% methanol/propan-2-amine in supercritical carbon dioxide, retention time 0.94 min |
| 25 | (3R,5R)-3-[1-Methyl-1-(6-cyclopropyl-pyridin-3-yl)-ethylamino]-5-(3,5-difluoro-phenyl)-1-(4-trifluoromethoxy-phenyl)-pyrrolidin-2-one dihydrochloride salt<br>$^1$H NMR (400.13 MHz, MeOD): δ 8.97-8.94 (m, 1H), 8.78 (dd, J = 2.0, 8.8 Hz, 1H), 7.78-7.73 (m, 1H), 7.45 (d, J = 8.8 Hz, 2H), 7.23 (d, J = 8.6 Hz, 2H), 7.02 (d, J = 5.9 Hz, 2H), 6.92-6.85 (m, 1H), 5.42-5.35 (m, 1H), 4.48-4.40 (m, 1H), 3.16-3.03 (m, 1H), 2.45-2.37 (m, 2H), 1.99 (d, J = 12.5 Hz, 6H), 1.54-1.47 (m, 2H), 1.34-1.27 (m, 2H).<br>MS (m/z): 532 (M + 1) | Yield 85%<br>Eluted with 15% isopropyl alcohol/DMEA in supercritical carbon dioxide, retention time 1.65 min |
| 26 | (3S,5S)-3-[1-Methyl-1-(6-cyclopropyl-pyridin-3-yl)-ethylamino]-5-(3,5-difluoro-phenyl)-1-(4-trifluoromethoxy-phenyl)-pyrrolidin-2-one dihydrochloride salt<br>$^1$H NMR (400.13 MHz, MeOD): δ 8.94 (d, J = 2.2 Hz, 1H), 8.77 (dd, J = 2.4, 8.8 Hz, 1H), 7.73 (d, J = 9.0 Hz, 1H), 7.46-7.43 (m, 2H), 7.23 (d, J = 8.3 Hz, 2H), 7.04-7.00 (m, 2H), 6.90-6.84 (m, 1H), 5.36 (dd, J = 6.4, 9.3 Hz, 1H), 4.41 (dd, J = 8.7, 11.1 Hz, 1H), 3.07-3.00 (m, 1H), 2.44-2.35 (m, 2H), 1.99 (d, J = 12.5 Hz, 6H), 1.54-1.49 (m, 2H), 1.31-1.27 (m, 2H).<br>MS (m/z): 532 (M + 1). | Yield 73%<br>Eluted with 15% isopropyl alcohol/DMEA in supercritical carbon dioxide, retention time 2.94 min |

TABLE 11-continued

| Ex N° | Compound, Name and Physical data | Yield and Comment |
|---|---|---|
| 27 | 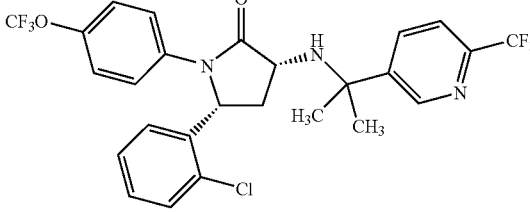<br>(3R,5R)-3-[1-Methyl-1-(6-trifluoromethyl-pyridin-3-yl)-ethylamino]-5-(2-chloro-phenyl)-1-(4-trifluoromethoxy-phenyl)-pyrrolidin-2-one<br>MS (m/z): 558.0 (M + 1).<br>$^1$H NMR (400.43 MHz, CDCl$_3$): δ 8.82 (s, 1H), 8.08 (d, J = 8.4 Hz, 1H), 7.61 (d, J = 8.4 Hz, 1H), 7.31-7.27 (m, 3H), 7.13-7.04 (m, 5H), 5.56-5.47 (m, 1H), 3.43 (dd, J = 8.4, 10.5 Hz, 1H), 2.77-2.65 (m, 2H), 1.81-1.76 (m, 1H), 1.56 (s, 3H), 1.53 (s, 3H).<br>Salt formation: tosylate - Add one equivalent p-toluenesulfonic acid monohydrate and crystallize from isopropanol. Yield 37%, MS (m/z): 558 (M + 1).<br>$^1$H NMR (400.43 MHz, MeOD): δ 9.03 (d, J = 2.6 Hz, 1H), 8.35 (dd, J = 2.6, 8.4 Hz, 1H), 7.91 (d, J = 7.9 Hz, 1H), 7.68-7.65 (m, 2H), 7.37-7.32 (m, 3H), 7.22-7.12 (m, 7H), 5.93-5.86 (m, 1H), 4.32 (dd, J = 9.0, 11.2 Hz, 1H), 2.88-2.81 (m, 1H), 2.33 (s, 3H), 2.23-2.19 (m, 1H), 1.95 (d, J = 2.6 Hz, 6H). | Yield 28.5%<br>Elute with 100% methanol with 0.2% DMEA in supercritical carbon dioxide, retention time 5.50 min. |
| 28 | 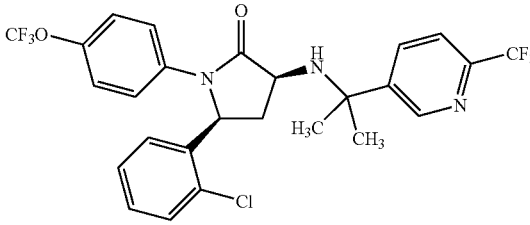<br>(3S,5S)-3-[1-Methyl-1-(6-trifluoromethyl-pyridin-3-yl)-ethylamino]-5-(2-chloro-phenyl)-1-(4-trifluoromethoxy-phenyl)-pyrrolidin-2-one<br>MS (m/z): 558.0 (M + 1).<br>$^1$H NMR (400.43 MHz, CDCl$_3$): δ 8.82 (s, 1H), 8.08 (d, J = 8.4 Hz, 1H), 7.61 (d, J = 8.4 Hz, 1H), 7.31-7.27 (m, 3H), 7.13-7.04 (m, 5H), 5.56-5.47 (m, 1H), 3.43 (dd, J = 8.4, 10.5 Hz, 1H), 2.77-2.65 (m, 2H), 1.81-1.76 (m, 1H), 1.56 (s, 3H), 1.53 (s, 3H). | Yield 28.5%<br>Elute with 100% methanol with 0.2% DMEA in supercritical carbon dioxide, retention time 5.50 min. |
| 30 | 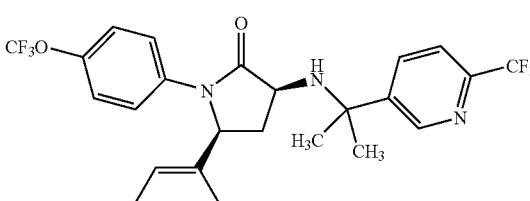<br>(3S,5S)-3-[1-Methyl-1-(6-trifluoromethyl-pyridin-3-yl)-ethylamino]-5-(3-ethyl-phenyl)-1-(4-trifluoromethoxy-phenyl)-pyrrolidin-2-one<br>MS (m/z): 552.0 (M + 1).<br>$^1$H NMR (400.43 MHz, CDCl$_3$): 8.82 (d, J = 2.2 Hz, 1H), 8.13 (d, J = 8.4 Hz, 1H), 7.62 (d, J = 7.9 Hz, 1H), 7.26-7.23 (m, 6H), 7.14-7.10 (m, 1H), 7.03-6.99 (m, 3H), 6.93-6.91 (m, 2H), 4.87 (dd, J = 5.9, 9.9 Hz, 1H), 3.38 (dd, J = 7.9, 11.0 Hz, 1H), 2.63-2.57 (m, 1H), 2.51 (q, J = 7.6 Hz, 2H), 2.00-1.94 (m, 1H), 1.58 (d, J = 10.1 Hz, 6H), 1.07 (t, J = 7.7 Hz, 3H). | Yield: 31%<br>Chiralcel OD-H 10% MeOH/0.2% IPAm/CO2, retention time 0.98 min. |

TABLE 11-continued

| Ex N° | Compound, Name and Physical data | Yield and Comment |
|---|---|---|
| 31 | 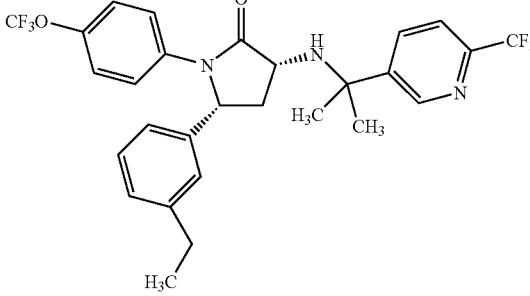<br>(3R,5R)-3-[1-Methyl-1-(6-trifluoromethyl-pyridin-3-yl)-ethylamino]-5-(3-ethyl-phenyl)-1-(4-trifluoromethoxy-phenyl)-pyrrolidin-2-one<br>MS (m/z): 552.0 (M + 1).<br>$^1$HNMR (400.43 MHz, CDCl$_3$): 8.81 (d, J = 2.2 Hz, 1H), 8.10 (dd, J = 1.8, 8.4 Hz, 1H), 7.61 (d, J = 8.4 Hz, 1H), 7.27-7.23 (m, 3H), 7.14-7.10 (m, 1H), 7.01 (t, J = 8.1 Hz, 3H), 6.92-6.91 (m, 2H), 4.87 (dd, J = 5.9, 9.9 Hz, 1H), 3.37 (dd, J = 7.9, 11.0 Hz, 1H), 2.64-2.58 (m, 1H), 2.54-2.48 (m, 2H), 1.88-1.80 (m, 1H), 1.55 (d, J = 9.7 Hz, 6H), 1.07 (t, J = 7.7 Hz, 3H). | Yield: 31%<br>Chiralcel OD-H 10%<br>MeOH/0.2%<br>IPAm/CO2 5<br>mL/min; retention time 1.86 min. |
| 32A | 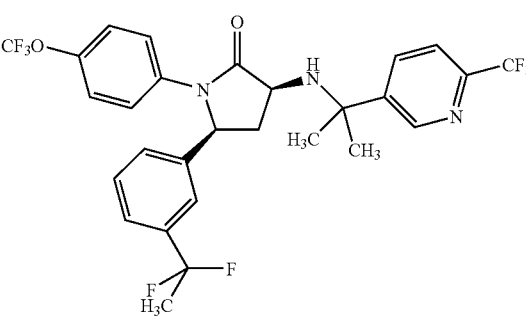<br>(3S,5S)-3-[1-Methyl-1-(6-trifluoromethyl-pyridin-3-yl)-ethylamino]-5-[3-(1,1-difluoro-ethyl)-phenyl]-1-(4-trifluoroethoxy-phenyl)-pyrrolidin-2-one<br>MS (m/z): 588 (M + 1).<br>$^1$HNMR (400.43 MHz, CDCl$_3$): 8.82-8.81 (m, 1H), 8.11 (dd, J = 1.8, 8.4 Hz, 1H), 7.62 (d, J = 8.4 Hz, 1H), 7.29-7.23 (m, 6H), 7.20-7.16 (m, 1H), 7.03 (d, J = 8.8 Hz, 2H), 4.95 (dd, J = 5.9, 9.9 Hz, 1H), 3.40 (dd, J = 7.9, 11.0 Hz, 1H), 2.67-2.61 (m, 1H), 1.89-1.83 (m, 1H), 1.80-1.71 (m, 3H), 1.57 (d, J = 8.4 Hz, 6H). | Yield: 34%<br>Chiralcel OD-H 10%<br>MeOH/0.2%<br>IPAm/CO2 5<br>mL/min; retention time 0.82 min. |
| 32B | 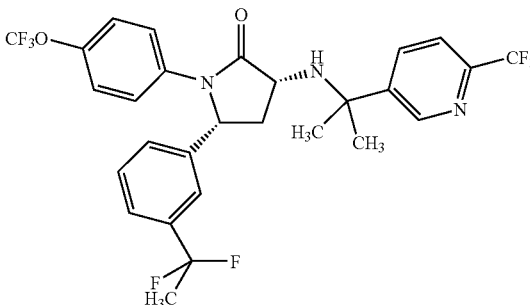<br>(3R,5R)-3-[1-Methyl-1-(6-trifluoromethyl-pyridin-3-yl)-ethyl-amino]-5-[3-(1,1-difluoro-ethyl)-phenyl]-1-(4-trifluoromethoxy-phenyl)-pyrrolidin-2-one<br>MS (m/z): 588 (M + 1).<br>$^1$HNMR (400.43 MHz, CDCl$_3$): 8.82 (d, J = 2.2 Hz, 1H), 8.11 (dd, J = 2.2, 8.4 Hz, 1H), 7.62 (d, J = 8.4 Hz, 1H), 7.30-7.23 (m, 6H), 7.17 (d, J = 7.0 Hz, 1H), 7.03 (d, J = 8.4 Hz, 2H), 4.95 (dd, J = 5.9, 9.9 Hz, 1H), 3.40 (dd, J = 7.9, 11.0 Hz, 1H), 2.67-2.61 (m, 1H), 1.89-1.83 (m, 1H), 1.80-1.71 (m, 3H), 1.56 (d, J = 9.2 Hz, 6H). | Yield: 34%<br>Chiralcel OD-H 10%<br>MeOH/0.2%<br>IPAm/CO2 5<br>mL/min; retention time 1.27 min. |

TABLE 11-continued

| Ex N° | Compound, Name and Physical data | Yield and Comment |
|---|---|---|
| 33A | ![structure]<br>(3S,5S)-3-[1-Methyl-1-(6-trifluoromethyl-pyridin-3-yl)-ethylamino]-5-(3-difluoromethoxy-phenyl)-1-(4-trifluoromethoxy-phenyl)-pyrrolidin-2-one<br>MS (m/z): 590.0 (M + 1). Method 2. | Yield 24.0%<br>Elute with 100% methanol with 0.2% DMEA in supercritical carbon dioxide |
| 33B | ![structure]<br>(3R,5R)-3-[1-Methyl-1-(6-trifluoromethyl-pyridin-3-yl)-ethylamino]-5-(3-difluoromethoxy-phenyl)-1-(4-trifluoromethoxy-phenyl)-pyrrolidin-2-one<br>MS (m/z): 590.0 (M + 1). Method 2 | Yield 26.0%<br>Elute with 100% methanol with 0.2% DMEA in supercritical carbon dioxide. |

EXAMPLE 34

(3R,5R)-3-[1-Methyl-1-(6-trifluoromethyl-pyridin-3-yl)-ethylamino]-5-[3-(2,2,2-trifluoro-ethoxy)-phenyl]-1-(4-trifluoromethyl-phenyl)-pyrrolidin-2-one

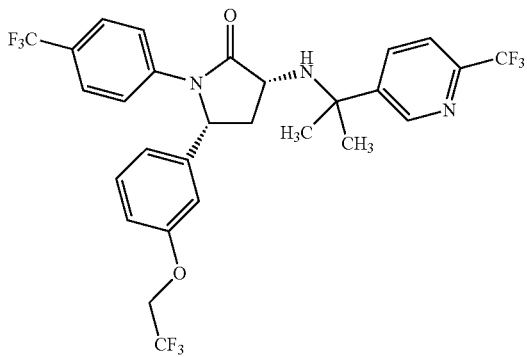

Add trifluoroacetic acid (3.5 mL, 46.1 mmol) dropwise to a biphasic mixture of (R)-3-((R)-1-phenyl-ethylamino)-5-[3-(2,2,2-trifluoro-ethoxy)-phenyl]-1-(4-trifluoromethyl-phenyl)-1,5-dihydro-pyrrol-2-one (4.8 g, 9.22 mmol) in toluene (24 mL) and water (9.6 mL). Stir at ambient temperature for 60 min. Observe significant formation of (R)-5-[3-(2,2,2-trifluoro-ethoxy)-phenyl]-1-(4-trifluoromethyl-phenyl)-pyrrolidine-2,3-dione (LC MS 77%, Ret. time=4.08 min., Method 3, MS (m/z): 416 (M−1). Separate the aqueous layer and wash the toluene layer with water, pH 7 buffer and saturated sodium chloride solution. Add acetic acid (4.23 mL, 73.8 mmol) and 1-methyl-1-(6-trifluoromethyl-pyridin-3-yl)-ethylamine (3.77 g, 18.4 mmol) to the toluene solution containing (R)-5-[3-(2,2,2-trifluoro-ethoxy)-phenyl]-1-(4-trifluoromethyl-phenyl)-pyrrolidine-2,3-dione. Heat to 55° C. for 18 hours. Observe significant formation of (R)-3-[1-methyl-1-(6-trifluoromethyl-pyridin-3-yl)-ethylamino]-5-[3-(2,2,2-trifluoro-ethoxy)-phenyl]-1-(4-trifluoromethyl-phenyl)-1,5-dihydro-pyrrol-2-one (LC MS 100%, Ret. time=5.26 min., Method 3, MS (m/z): 604 (M+1). Dilute reaction mixture with ethyl acetate and wash with water and saturated sodium chloride solution, dry over sodium sulfate, filter and concentrate to dryness. Dissolve the crude (R)-3-[1-methyl-1-(6-trifluoromethyl-pyridin-3-yl)-ethylamino]-5-[3-(2,2,2-trifluoro-ethoxy)-phenyl]-1-(4-trifluoromethyl-phenyl)-1,5-dihydro-pyrrol-2-one in acetic acid (46 mL) and add sodium cyanoborohydride (1.16 g. 18.4 mmol). Stir 15 min. at ambient temperature. Concentrate under reduced pressure. Dissolve the residue in ethyl acetate and wash with saturated sodium bicarbonate solution and saturated sodium chloride solution, dry over sodium sulfate, filter and concentrate under reduced pressure. Purify the residue by silica gel chromatography (5-50% ethyl acetate-hexane) and purify again by silica gel chromatography (0-1% methanol-dichloromethane) to obtain (3R,5R)-3-[1-methyl-1-(6-trifluoromethyl-pyridin-3-yl)-ethylamino]-5-[3-(2,2,2-trifluoro-ethoxy)-phenyl]-1-(4-trifluoromethyl-phenyl)-pyrrolidin-2-one (2.36 g, 42%) as a clear colorless oil. MS (m/z): 606 (M+1).

$^1$H NMR (DMSO-$d_6$, 400 MHz): δ 8.98 (d, 1H, J=2.2 Hz), 8.26 (dd, 1H, J=8.4, 2.2 Hz), 7.82 (d, 1H, J=8.4 Hz), 7.58 (d,

2H, J=8.8 Hz), 7.52 (d, 2H, J=8.4 Hz), 7.20 (dd, 1H, J=7.4, 7.4 Hz), 6.97 (dd, 1H, J=2.0, 2.0 Hz), 6.89 (d, 1H, J=7.9 Hz), 6.84 (dd, 1H, J=7.9, 2.2 Hz), 5.17 (dd, 1H, J=9.7, 6.2 Hz), 4.72-4.61 (m, 2H), 3.48-3.41 (m, 1H), 2.88 (d, 1H, J=4.8 Hz), 2.71-2.63 (m, 1H), 1.68 (dd, 1H, J=22.0, 10.5 Hz), 1.51 (s, 3H), 1.47 (s, 3H).

Salt formation: tosylate—Add one equivalent p-toluenesulfonic acid monohydrate and crystallize from methanol-isopropanol. Yield 82%, MS (m/z): 606.

Prepare the following Compounds essentially by the method of Example 34.

TABLE 12

| Ex N° | Compound, Name and Physical data | Yield and Comment |
|---|---|---|
| 35 | 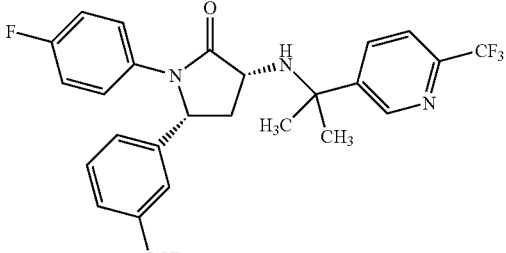<br>(3R,5R)-3-[Methyl-1-(6-trifluoromethyl-pyridin-3-yl)-ethylamino]-5-(3-trifluoromethoxy-phenyl)-1-(4-fluoro-phenyl)-pyrrolidin-2-one<br>$^1$H NMR (DMSO-d$_6$, 400 MHz): δ 8.98 (d, 1 H, J = 2.2 Hz), 8.26 (dd, 1 H, J = 8.1, 2.0 Hz), 7.82 (d, 1 H, J = 7.9 Hz), 7.36 (dd, 1 H, J = 7.9, 7.9 Hz), 7.30-7.24 (m, 3 H), 7.22 (s, 1 H), 7.16-7.12 (m, 1 H), 7.09-7.02 (m, 2 H), 5.18 (dd, 1 H, J = 9.5, 6.4 Hz), 3.40 (ddd, 1 H, J = 11.6, 7.2, 3.6 Hz), 2.88 (d, 1 H, J = 4.4 Hz), 2.70 (ddd, 1 H, J = 13.2, 6.8, 5.3 Hz), 1.66 (dd, 1 H, J = 21.7, 10.2 Hz), 1.51 (s, 3 H), 1.46 (s, 3 H).<br>Salt formation: tosylate-Add one equivalent p-toluenesulfonic acid monohydrate and crystallize from isopropanol. Yield 90%, MS (m/z): 542. | Use THF in place of toluene during the hydrolysis step. Remove THF under reduced pressure and replace with toluene and continue extractive work up.<br>Yield 41%. |
| 36 | 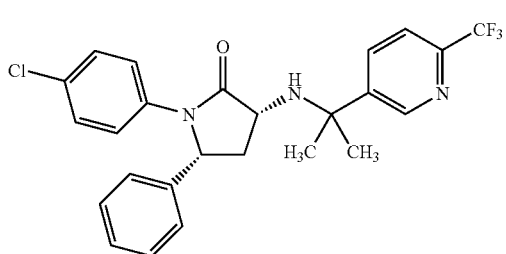<br>(3R,5R)-3-[1-methyl-1-(6-trifluoromethyl-pyridin-3-yl)-ethylamino]-5-(3-trifluoromethoxy-phenyl)-1-(4-chloro-phenyl)-pyrrolidin-2-one<br>$^1$H NMR (DMSO-d$_6$, 400 MHz): δ 8.98 (d, 1H, J = 2.2 Hz), 8.26 (dd, 1H, J = 8.4, 2.2Hz), 7.82 (d, 1H, J = 7.9Hz), 7.37 (t, 1H, J = 7.9Hz), 7.29-7.21 (m, 6H), 7.17-7.13 (m, 1H), 5.19 (dd, 1H, J = 9.7, 6.2Hz), 3.45-3.37 (m, 1H), 2.88 (d, 1H, J = 4.4Hz), 2.74-2.66 (m, 1H), 1.70-1.61 (m, 1H), 1.50 (s, 3H), 1.46 (s, 3H).<br>MS (m/z): 558.0 (M + 1).<br>HPLC Ret. time = 4.92 min.<br>Salt formation: tosylate-Add 1 equiv toluene sulfonic acid monohydrate and crystallize from isopropanol.<br>Yield 86%, MS (m/z): 558.0. | Yield 54%. |

TABLE 12-continued

| Ex N° | Compound, Name and Physical data | Yield and Comment |
|---|---|---|
| 37 | 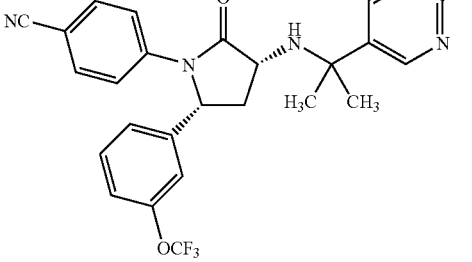<br>4-[(3R,5R)-3-[1-Methyl-1-(6-trifluoromethyl-pyridin-3-yl)-ethylamino]-2-oxo-5-(3-trifluoromethoxy-phenyl)-pyrrolidin-1-yl]-benzonitrile<br>$^1$H NMR (DMSO-d$_6$, 400 MHz): δ 8.98 (d, 1H, J = 2.2 Hz), 8.26 (dd, 1H, J = 8.4, 2.2Hz), 7.82 (d, 1H, J = 7.9Hz), 7.70 (d, 2H, J = 8.8Hz), 7.48 (d, 2H, J = 8.8Hz), 7.38 (t, 1H, J = 7.9Hz), 7.28 (d, 1H, J = 7.9Hz), 7.25 (s, 1H), 7.18-7.14 (m, 1H), 5.26 (dd, 1H, J = 9.7, 6.6Hz), 3.48-3.42 (m, 1H), 2.91 (d, 1H, J = 4.8Hz), 2.76-2.69 (m, 1H), 1.71-1.63 (m, 1H), 1.50 (s, 3H), 1.46 (s, 3H).<br>MS (m/z): 549.2 (M + 1).<br>HPLC Ret. time = 4.64 min<br>Salt formation: tosylate-Add 1 equiv toluene sulfonic acid monohydrate and crystallize from isopropanol. Yield 86%, MS (m/z): 549.2. | Yield 48%. |
| 38 | 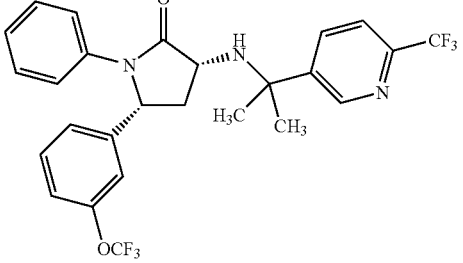<br>(3R,5R)-3-[1-Methyl-1-(6-trifluoromethyl-pyridin-3-yl)-ethylamino]-5-(3-trifluoromethoxy-phenyl)-1-phenyl-pyrrolidin-2-one<br>MS (m/z): 524 (M + 1).<br>$^1$H NMR (400 MHz, DMSO-d$_6$) δ 8.97 (s, 1H), 8.26 (d, 1H, J = 8.3Hz), 7.81 (d, 1H, J = 7.9Hz), , 7.35 (dd, 1H, J = 7.6, 7.6Hz), 7.27-7.17 (m, 6H), 7.12 (d, 1H, J = 7.9 Hz), 7.01 (dd, 1H, J = 7.1, 7.1Hz), 5.21 (dd, 1H, J = 9.4, 6.4Hz), 3.40 (dd, 1H, J = 9.2, 9.2Hz), 2.89 (s, 1H), 2.73-2.65 (m, 1H), 1.64 (dd, 1H, J = 22.0, 10.5Hz), 1.50 (s, 3H), 1.46 (s, 3H).<br>Salt formation: tosylate-Add one equivalent p-toluenesulfonic acid monohydrate and crystallize from isopropanol. Yield 82%, MS (m/z): 524. | Yield 45% |
| 39 | 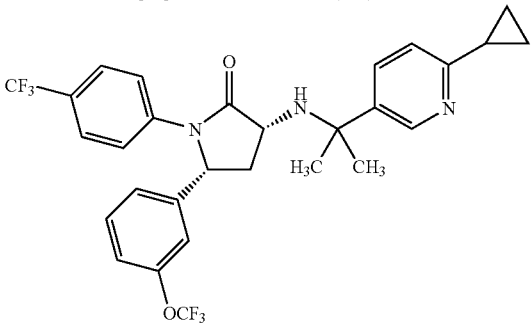<br>(3R,5R)-3-[1-Methyl-1-(6-cyclopropyl-pyridin-3-yl)-ethylamino]-5-(3-trifluoromethoxy-phenyl)-1-(4-trifluoromethyl-phenyl)-pyrrolidin-2-one | Yield 19% |

| Ex N° | Compound, Name and Physical data | Yield and Comment |
|---|---|---|
|  | MS (m/z) 564.2<br>Salt formation: tosylate-Add 1 equiv toluene sulfonic acid monohydrate in acetonitrile and evaporated to a weighable solid. Yield 82%, MS (m/z): 565.2. |  |
| 40 | 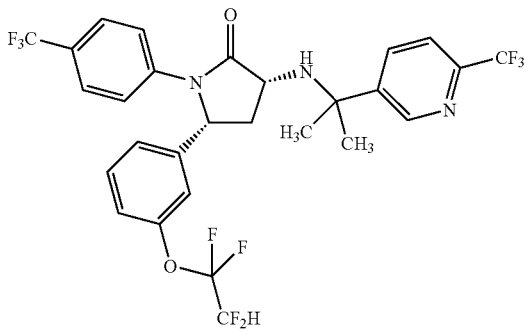<br>(3R,5R)-3-[1-Methyl-1-(6-trifluoromethyl-pyridin-3-yl)-ethylamino]-5-[3-(1,1,2,2-tetrafluoro-ethoxy)-phenyl]-1-(4-trifluoromethyl-phenyl)-pyrrolidin-2-one<br>$^1$H NMR (400 MHz, DMSO-$d_6$) δ 8.98 (s, 1H), 8.26 (d, 1H, J = 8.3Hz), 7.81 (d, 1H, J = 8.3Hz), 7.58 (d, 2H, J = 8.8Hz), 7.49 (d, 2H, J = 8.3Hz), 7.34 (dd, 1H, J = 7.8, 7.8Hz), 7.24 (d, 1H, J = 7.9Hz), 7.14 (s, 1H), 7.06 (d, 1H, J = 7.9Hz), 6.71 (t, 1H, J = 51.0 Hz), 5.26 (dd, 1H, J = 9.7, 6.6Hz), 3.48-3.40 (m, 1H), 2.91 (d, 1H, J = 4.8 Hz), 2.76-2.68 (m, 1H), 1.67 (ddd, 1H, J = 11.0, 11.0, 11.0 Hz), 1.50 (s, 3H), 1.46 (s, 3H).<br>MS (m/z): 624.<br>Salt formation: tosylate-Add one equivalent p-toluenesulfonic acid monohydrate and crystallize from isopropanol. Yield 89%. | Yield 52% |
| 41 | 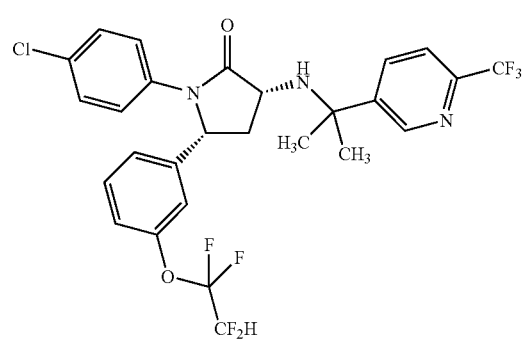<br>(3R,5R)-3-[1-Methyl-1-(6-trifluoromethyl-pyridin-3-yl)-ethylamino]-5-[3-(1,1,2,2-tetrafluoro-ethoxy)-phenyl]-1-(4-chloro-phenyl)-pyrrolidin-2-one<br>$^1$H NMR (400 MHz, DMSO-$d_6$) δ 8.97 (s, 1H), 8.25 (d, 1H, J = 7.9Hz), 7.81 (d, 1H, J = 7.9Hz), 7.33 (dd, 1H, J = 7.9, 7.9Hz), 7.27 (s, 4H), 7.22 (d, 1H, J = 7.9Hz), 7.12 (s, 1H), 7.06 (d, 1H, J = 8.3Hz), 6.72 (dd, 1H, J = 51.4, 51.4Hz), 5.18 (dd, 1H, J = 9.2, 6.6Hz), 3.44-3.36 (m, 1H), 2.89 (d, 1H, J = 4.4Hz), 2.74-2.65 (m, 1H), 1.64 (ddd, 1H, J = 11.0, 11.0, 11.0 Hz), 1.49 (s, 3H), 1.45 (s, 3H)<br>MS (m/z): 590.<br>Salt formation: tosylate-Add one equivalent p-toluenesulfonic acid monohydrate and crystallize from isopropanol. Yield 96%. | Yield 59% |

| Ex N° | Compound, Name and Physical data | Yield and Comment |
|---|---|---|
| 42 | 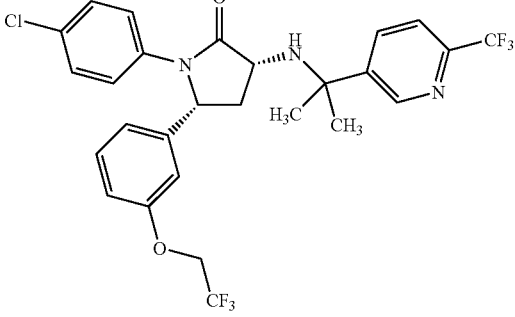<br>(3R,5R)-3-[1-Methyl-1-(6-trifluoromethyl-pyridin-3-yl)-ethylamino]-1-(4-chloro-phenyl)-5-[3-(2,2,2-trifluoro-ethoxy)-phenyl]-pyrrolidin-2-one<br>¹H NMR (400 MHz, DMSO-d₆) δ 8.97 (s, 1H), 8.25 (d, 1H, J = 7.9Hz), 7.81 (d, 1H, J = 8.3Hz), 7.28 (dd, 4H, J = 16.3, 9.2Hz), 7.18 (dd, 1H, J = 7.9, 7.8Hz), 6.93 (s, 1H), 6.88-6.81 (m, 2H), 5.08 (dd, 1H, J = 9.4, 6.4Hz), 4.71-4.60 (m, 2H), 3.43-3.36 (m, 1H), 2.84 (d, 1H, J = 4.0 Hz), 2.67-2.58 (m, 1H), 1.65 (ddd, 1H, J = 10.8, 10.8, 10.8 Hz), 1.49 (s, 3H), 1.45 (s, 3H).<br>MS (m/z): 572.<br>Salt formation: tosylate-Add one equivalent p-toluenesulfonic acid monohydrate and crystallize from isopropanol. Yield 92%. | Yield 52% |
| 43 | 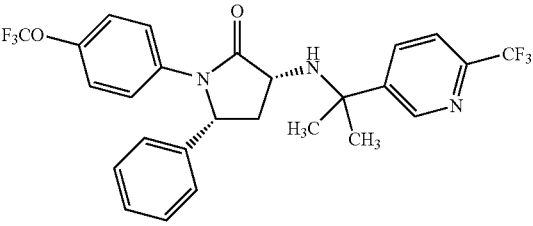<br>(3R,5R)-3-[1-Methyl-1-(6-trifluoromethyl-pyridin-3-yl)-ethylamino]-5-phenyl-1-(4-trifluoromethoxy-phenyl)-pyrrolidin-2-one<br>¹H NMR (400 MHz, DMSO-d₆) δ 8.97 (d, 1H, J = 2.2 Hz), 8.25 (dd, 1H, J = 8.4, 1.8Hz), 7.81 (d, 1H, J = 8.4 Hz), 7.37 (d, 2H, J = 9.2Hz), 7.25-7.12 (m, 7H), 5.12 (dd, 1H, J = 9.7, 6.6Hz), 3.44-3.37 (m, 1H), 2.88 (d, 1H, J = 4.0 Hz), 2.65 (ddd, 1H, J = 13.3, 6.9, 5.2Hz), 1.63 (ddd, 1H, J = 10.5, 10.5, 10.5Hz), 1.50 (s, 3H), 1.46 (s, 3H).<br>MS (m/z): 524 (M + 1).<br>Salt formation: tosylate-Add one equivalent p-toluenesulfonic acid monohydrate and crystallize from isopropanol. Yield 89%. | Yield 66% |
| 44 | 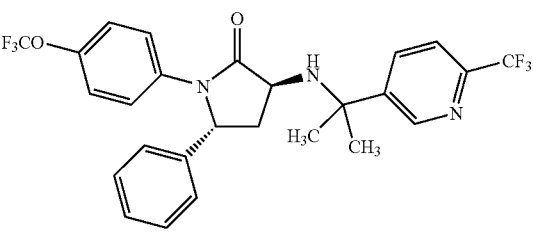<br>(3S,5R)-3-[1-Methyl-1-(6-trifluoromethyl-pyridin-3-yl)-ethylamino]-5-phenyl-1-(4-trifluoromethoxy-phenyl)-pyrrolidin-2-one<br>¹H NMR (400 MHz, DMSO-d₆) δ 8.93 (d, 1H, J = 2.2 Hz), 8.20 (dd, 1H, J = 8.1, 2.0 Hz), 7.78 (d, 1H, J = 8.4 Hz), 7.62 (d, 2H, J = 9.2Hz), 7.29-7.21 (m, 4H), 7.18-7.10 (m, 3H), 5.45 (dd, 1H, J = 8.6, 2.0 Hz), 3.53-3.46 (m, 1H), 2.80 (d, 1H, J = 3.5Hz), 2.39-2.30 (m, 1H), 2.01 | Yield 2% |

TABLE 12-continued

| Ex N° | Compound, Name and Physical data | Yield and Comment |
|---|---|---|
| | (ddd, 1H, J = 12.7, 8.1, 2.1Hz), 1.46 (s, 3H), 1.42 (s, 3H).<br>MS (m/z): 524 (M + 1).<br>Salt formation: tosylate-Add one equivalent p-toluenesulfonic acid monohydrate and concentrate from isopropanol. Yield 100%. | |
| 45 | (3R,5R)-3-[1-Methyl-1-(6-trifluoromethyl-pyridin-3-yl)-ethylamino]-5-(3-trifluoromethoxy-phenyl)-1-(4-bromo-phenyl)-pyrrolidin-2-one<br>MS (m/z): 602.0 (M + 1).<br>RP HPLC Tr = 5.01 min. (Method 3) | Yield 52% |
| 46 | (3R,5R)-3-[1-Methyl-1-(6-cyclopropyl-pyridin-3-yl)-ethylamino]-5-(3-trifluoromethoxy-phenyl)-1-(4-chloro-phenyl)-pyrrolidin-2-one<br>MS (m/z): 530.2 (M + 1).<br>RP HPLC Tr = 3.32 min. (Method 3) | Yield 19% |
| 47A | (3R,5R)-3-[1-Methyl-1-(6-trifluoromethyl-pyridin-3-yl)-ethylamino]-5-(3,4-difluoro-phenyl)-1-(4-trifluoromethoxy-phenyl)-pyrrolidin-2-one tosylate<br>MS (m/z): 560.0 (M + 1).<br>$^1$H NMR (400.43 MHz, MeOD): δ 9.03 (d, J = 2.6Hz, 1H), 8.35 (dd, J = 2.2, 8.4Hz, 1H), 7.90 (d, J = 8.4Hz, 1H), 7.67 (d, J = 8.4Hz, 2H), 7.35-7.33 (m, 2H), 7.19-7.12 (m, 7H), 5.21 (dd, J = 6.2, 9.2Hz, 1H), 4.29 (dd, J = 8.4, 11.4Hz, 1H), 2.83-2.76 (m, 1H), 2.33 (s, 3H), 2.10-2.02 (m, 1H), 1.95 (d, J = 3.5Hz, 6H). | Yield 45.3% |

TABLE 12-continued

| Ex N° | Compound, Name and Physical data | Yield and Comment |
|---|---|---|
| 47B | 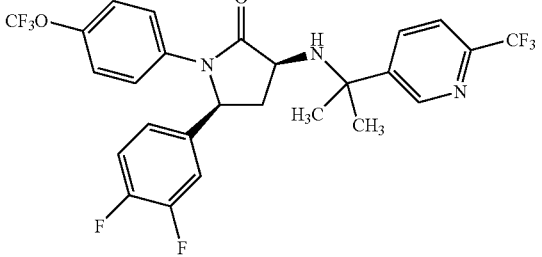<br><br>(3S,5S)-3-[1-Methyl-1-(6-trifluoromethyl-pyridin-3-yl)-ethylamino]-5-(3,4-difluoro-phenyl)-1-(4-trifluoromethoxy-phenyl)-pyrrolidin-2-one tosylate<br>MS (m/z): 560.0 (M + 1).<br>$^1$H NMR (400.43 MHz, MeOD): δ 9.03 (d, J = 2.6Hz, 1H), 8.35 (dd, J = 2.2, 8.4Hz, 1H), 7.90 (d, J = 8.4Hz, 1H), 7.67 (d, J = 8.4Hz, 2H), 7.35-7.33 (m, 2H), 7.19-7.12 (m, 7H), 5.21 (dd, J = 6.2, 9.2Hz, 1H), 4.29 (dd, J = 8.4, 11.4Hz, 1H), 2.83-2.76 (m, 1H), 2.33 (s, 3H), 2.10-2.02 (m, 1H), 1.95 (d, J = 3.5Hz, 6H). | Yield 38.7% |
| 48A | 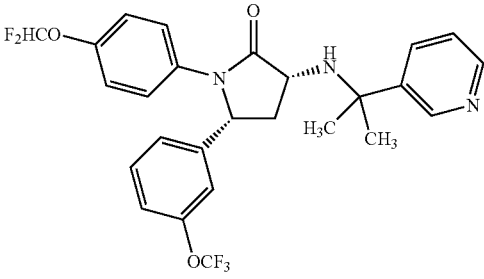<br><br>(3R,5R)-3-[1-methyl-1-(6-trifluoromethyl-pyridin-3-yl)-ethylamino]-1-(4-difluoromethoxy-phenyl)-5-(3-trifluoromethoxy-phenyl)-pyrrolidin-2-one<br>LC-MS ESI m/z: 590 (M + H)$^+$, retention time 4.73 min, Method 3.<br>Salt formation: tosylate-Add one equivalent p-toluenesulfonic acid monohydrate and concentrate from isopropanol. Yield 98%. | Yield 31%<br>Use 0.3 equivalents of HOAc and 3 equivalents of amine in enamine formation (second step). |
| 48B | 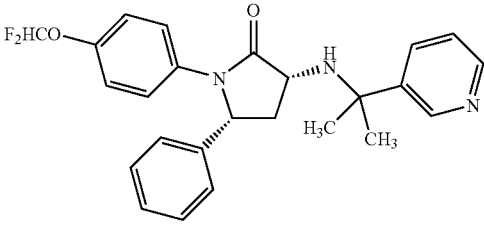<br><br>(3R,5R)-3-[1-methyl-1-(6-trifluoromethyl-pyridin-3-yl)-ethylamino]-1-(4-difluoromethoxy-phenyl)-5-phenyl-pyrrolidin-2-one<br>LC-MS ESI m/z: 506 (M + H)$^+$, retention time 4.16 min, Method 3. | Yield 39%<br>Use 0.3 equivalents of HOAc in enamine formation (second step). |

EXAMPLE 49

(3R,5R)-3-[1-Methyl-1-(6-trifluoromethyl-pyridin-3-yl)-ethylamino]-5-phenyl-1-(4-trifluoromethoxy-phenyl)-pyrrolidin-2-one tosylate

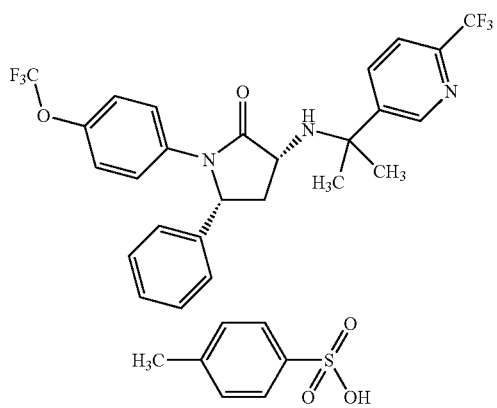

Add trifluoroacetic acid (83.5 mL, 1.10 mol) and sodium triacetoxyborohydride (175 g, 828 mmol) to a slurry of 3-[1-methyl-1-(6-trifluoromethyl-pyridin-3-yl)-ethylamino]-(R)-5-phenyl-1-(4-trifluoromethoxy-phenyl)-1,5-dihydro-pryrrol-2-one (288 g, 552 mmol) in toluene (2.80 L) under a nitrogen atmosphere. Stir for 45 min, and add acetic acid (200 mL). After stirring 3 h, add trifluoroacetic acid (100 mL) and sodium triacetoxyborohydride (56 g, 265 mmol). After stirring for 24 hours at ambient temperature, heat the slurry to 35° C. After 2 hours, cool the mixture to ambient temperature and transfer by cannula into water (3.0 L). Dilute with MTBE (2.0 L), agitate the biphasic mixture, and discard the aqueous phase. Wash the organic layer with water (2.0 L) and saturated sodium hydrogen carbonate solution (2.0 L). Concentrate the organic layer to an oil under reduced pressure (10 torr, 30° C.), and dissolve in isopropyl alcohol (2.0 L). To the resulting solution, charge para-toluene sulfonic acid monohydrate (100.7 g, 518 mmol) and water (200 mL). Heat the slurry to 65° C. then slowly cool to ambient temperature and stir for 12 hours. Filter the slurry and wash the precipitate with isopropyl acetate (250 mL). Dry the white solid on a nitrogen press for 5 hours to give (3R,5R)-3-[1-methyl-1-(6-trifluoromethyl-pyridin-3-yl)-ethylamino]-5-phenyl-1-(4-trifluoromethoxy-phenyl)-pyrrolidin-2-one tosylate (298 g, 82%):

$^1$H NMR (400 MHz, DMSO-$d_6$) δ 10.10 (1H, br), 9.08 (1H, d, J=4 Hz), 8.39 (1H, dd, J=4, 8 Hz), 8.04 (1H, d, J=8 Hz), 7.49 (2H, m), 7.38 (2H, m), 7.21-7.28 (7H, m), 7.10 (2H, m), 5.21 (1H, dd, J=4, 8 Hz), 4.27 (1H, br s), 2.69 (1H, m), 2.26 (3H, s), 2.02 (1H, m), 1.85 (6H, m); MS (m/z): 524.2 (M+1).

EXAMPLE 50

(3R,5R)-3-[1-Methyl-1-(6-trifluoromethylpyridin-3-yl)ethylamino]-5-(3-cyclopropoxy-phenyl)-1-(4-trifluoromethylphenyl)pyrrolidin-2-one

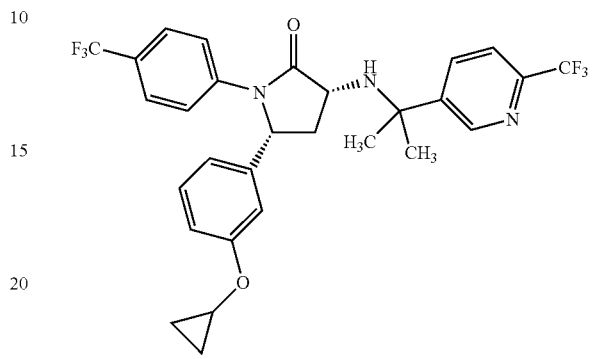

Add trifluoroacetic acid (1.5 mL, 20 mmol) to a mixture of (R)-3-((R)-1-phenyl-ethylamino)-5-(3-cyclopropoxy-phenyl)-1-(4-trifluoromethyl-phenyl)-1,5-dihydro-pyrrol-2-one (1.92 g, 4.01 mmol) in toluene (10 mL) and water (4 mL). Stir at ambient temperature for 60 min. Observe significant formation of (R)-5-(3-cyclopropoxy-phenyl)-1-(4-trifluoromethyl-phenyl)-pyrrolidine-2,3-dione. LCMS, Ret. time=4.14 min., Method 3, MS (m/z): 376.0 (M+), 374.0 (M−1). Add a solution of 1-methyl-1-(6-trifluoromethyl-pyridin-3-yl)-ethylamine (1.2 g, 5.9 mmol) in toluene (10 mL) to the reaction solution. Then add acetic acid (1.9 mL, 33 mmol). Heat at 50° C. for 14 hours. Concentrate under reduced pressure. Purify the residue by silica gel chromatography (0-10% ethyl acetate-hexane) to obtain (R)-3-[1-methyl-1-(6-trifluoromethyl-pyridin-3-yl)-ethylamino]-5-(3-cyclopropoxy-phenyl)-1-(4-trifluoromethyl-phenyl)-1,5-dihydro-pyrrol-2-one as a tan foam. LCMS, Ret. time=5.40 min., Method 3, MS (m/z): 562.0 (M+), 560.0 (M−1). Dissolve (R)-3-[1-methyl-1-(6-trifluoromethyl-pyridin-3-yl)-ethylamino]-5-(3-cyclopropoxy-phenyl)-1-(4-trifluoromethyl-phenyl)-1,5-dihydro-pyrrol-2-one (1.09 g, 1.94 mmol) in acetic acid (20 mL) and add sodium cyanoborohydride (240 mg. 3.8 mmol). Stir 1 hour at ambient temperature. Concentrate under reduced pressure. Dissolve the residue in dichloromethane and wash with saturated sodium bicarbonate solution, dry over sodium sulfate, filter and concentrate under reduced pressure. Purify the residue by silica gel chromatography (0-15% ethyl acetate-hexane) to obtain (3R,5R)-3-[1-methyl-1-(6-trifluoromethyl-pyridin-3-yl)-ethylamino]-5-(3-cyclopropoxy-phenyl)-1-(4-trifluoromethyl-phenyl)-pyrrolidin-2-one (645 mg, 59%) as a white foam. LCMS, Ret. time=5.04 min, Method 3 MS (m/z): 564.0 (M+1).

Prepare the following Compounds essentially by the method of Example 50.

TABLE 13

| Ex. N° | Compound, Name and Physical data | Yield |
|---|---|---|
| 51 | 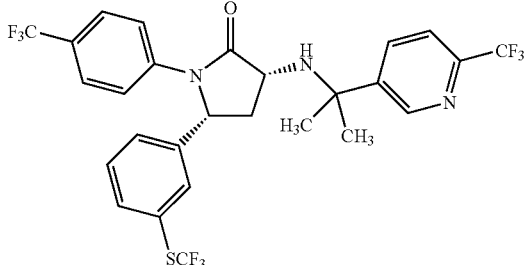<br>(3R,5R)-3-[1-Methyl-1-(6-trifluoromethyl-pyridin-3-yl)-ethylamino]-5-(3-trifluoromethylsulfanyl-phenyl)-1-(4-trifluoromethyl-phenyl)-pyrrolidin-2-one<br>Yield 22%; LC/MS Ret. time = 5.26, Method 3, MS (m/z): 608 (M + 1).<br>Salt formation: tosylate-quantative yield. Evaporation to dry, MS (m/z): 608 (M + 1). | Combine enamine and amine in dichloro-methane and heat at 40° C. for 17 hours. Use 5 equiv of NaBH$_3$CN for reduction (2 hours, ambient temperature). Purify by silica gel chromatography (25% EtOAc-hexane). |
| 52 | 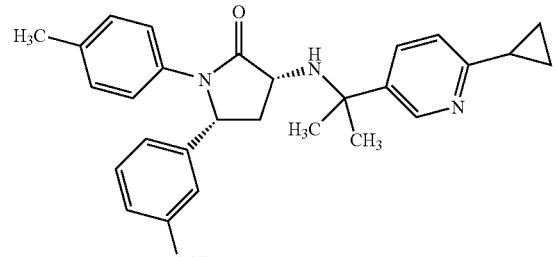<br>(3R,5R)-3-[1-Methyl-1-(6-cyclopropylpyridin-3-yl)-ethylamino]-5-(3-trifluoromethoxyphenyl)-1-p-tolyl-pyrrolidin-2-one<br>LCMS: 3.18 min. (Method 3); ESMS m/z 510.2 (M + 1). | Yield 22% |
| 53 | 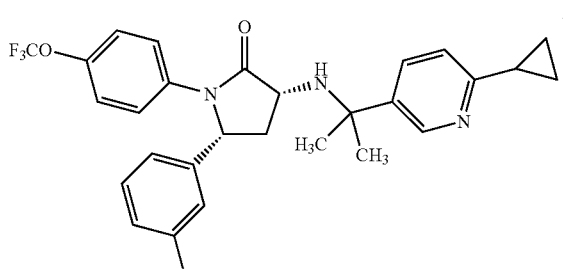<br>(3R,5R)-3-[1-Methyl-1-(6-cyclopropylpyridin-3-yl)-ethylamino]-5-(3-chlorophenyl)-1-(4-trifluoromethoxy-phenyl)pyrrolidin-2-one<br>LCMS: 3.38 min. (Method 3); ESMS m/z 530.0 (M + 1). | Yield 22%. |
| 54 | 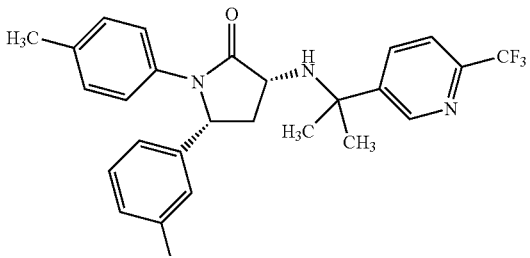<br>(3R,5R)-3-[1-Methyl-1-(6-trifluoromethylpyridin-3-yl)-ethylamino]-5-(3-trifluoromethoxyphenyl)-1-p-tolyl-pyrrolidin-2-one<br>LCMS: 4.75 min. (Method 3); ESMS m/z 538.2 (M + 1). | Yield 36%. |

EXAMPLE 55

(5R)-3-[1-Methyl-1-(6-chloro-pyridin-3-yl)-ethylamino]-5-(3-fluoro-phenyl)-1-(4-trifluoromethoxyphenyl)-pyrrolidin-2-one L-tartrate

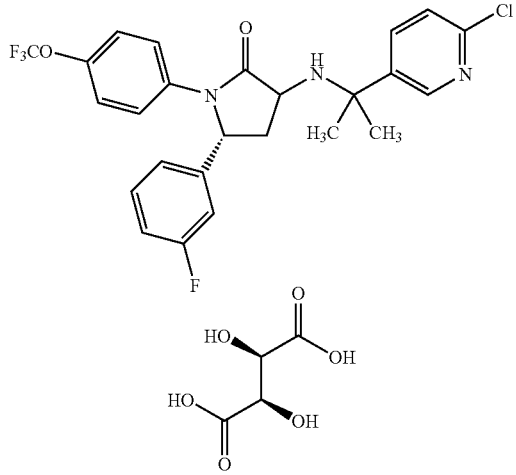

Dissolve (5R)-3-diazo-5-(3-fluoro-phenyl)-1-(4-trifluoromethoxy-phenyl)-pyrrolidin-2-one (295 mg, 0.81 mmol) and 1-methyl-1-(6-chloro-pyridin-3-yl)-ethylamine (0.6 g 3.5 mmol) in dry toluene (8 mL). Stir under nitrogen and heat to 45° C. Add rhodium acetate dimer dihydrate (40 mg, 0.09 mmol). Stir at 45° C. for 30 minutes then concentrate the reaction mixture under reduced pressure. Purify on an SCX-2 ion exchange resin cartridge (eluent methanol followed 2M $NH_3$ in methanol) and then by chromatography on a silica gel column (eluent dichloromethane/methanol) to give the titled compound as a diastereomer mixture (330 mg, 80%).
Instrumentation Perform Supercritical Fluid Chromatography (SFC) analysis on a Berger Minigram system configured with 6-way column and solvent switching. Perform SFC purification on a Berger Multigram II system. Equip both systems with a Knauer variable wavelength UV detector supplied by Mettler-Toledo AutoChem (Leicester, UK). Deliver liquid $CO_2$ to the laboratory by a Berger GDS-3000 system supplied also by Mettler-Toledo AutoChem.

Separate the diastereomer mixture by Supercritical Fluid Chromatography on an ADH column eluting with 25% methanol/propan-2-amine in supercritical carbon dioxide. Prepare the tartrate salt with tartaric acid (1 eq) in methanol and isolate the salt by evaporation of the solvent to give Example 56 and Example 57.

EXAMPLE 56

(3R,5R)-3-[1-methyl-1-(6-chloro-pyridin-3-yl)-ethylamino]-5-(3-fluoro-phenyl)-1-(4-trifluoromethoxyphenyl)-pyrrolidin-2-one L-tartrate

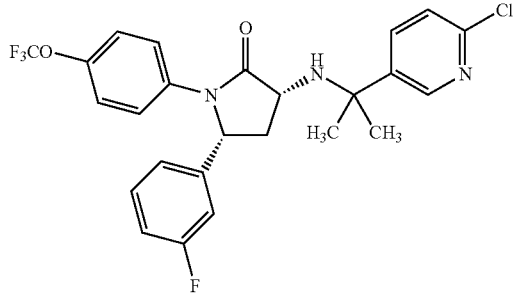

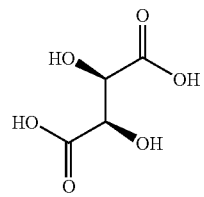

$^1$H NMR (400.13 MHz, MeOD): δ8.58 (s, 1H), 8.10 (d, J=8.3 Hz, 1H), 7.45-7.39 (m, 3H), 7.31-7.26 (m, 1H), 7.16 (d, J=8.3 Hz, 2H), 7.08 (d, J=7.8 Hz, 1H), 7.01 (d, J=9.8 Hz, 1H), 6.94 (t, J=8.3 Hz, 1H), 5.16 (t, J=7.6 Hz, 1H), 4.54 (s, 2H), 3.59 (t, J=9.3 Hz, 1H), 2.85-2.65 (m, 1H), 1.81 (q, J=10.9 Hz, 1H), 1.60 (s, 6H). Yield 63%, retention time 0.71 min. Tartrate salt.

EXAMPLE 57

(3S,5R)-3-[1-Methyl-1-(6-chloro-pyridin-3-yl)-ethylamino]-5-(3-fluoro-phenyl)-1-(4-trifluoromethoxyphenyl)-pyrrolidin-2-one L-tartrate

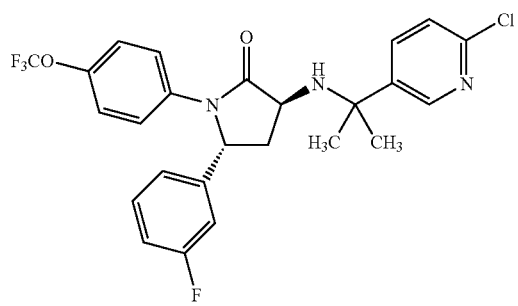

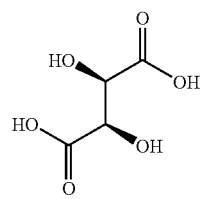

$^1$H NMR (400.13 MHz, MeOD): δ8.55 (s, 1H), 8.55 (s, 1H), 8.06 (d, J=8.1 Hz, 1H), 7.65 (d, J=7.8 Hz, 2H), 7.42 (d, J=8.3 Hz, 1H), 7.34-7.30 (m, 1H), 7.22 (d, J=8.3 Hz, 2H), 6.99-6.92 (m, 3H), 5.42 (d, J=9.0 Hz, 1H), 4.54 (s, 2H), 3.62 (t, J=8.9 Hz, 1H), 2.49-2.41 (m, 1H), 2.19-2.14 (m, 1H), 1.55 (s, 6H).

Yield 9.7%, retention time 1.26 min. Tartrate salt.

Prepare the following Compounds essentially by the method of Example 55, 56 and 57.

TABLE 14

| Ex. N° | Compound, Name, Physical Data | Yield Comments |
|---|---|---|
| 58 | 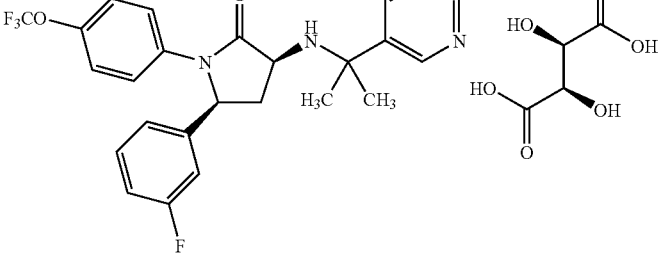<br>(3S,5S)-3-[1-Methyl-1-(6-chloro-pyridin-3-yl)-ethylamino]-5-(3-Fluoro-phenyl)-1-(4-trifluoromethoxy-phenyl)-pyrrolidin-2-one L-tartrate<br>$^1$H NMR (400.13 MHz, MeOD): δ 8.58 (d, J = 2.4Hz, 1H), 8.10 (dd, J = 2.7, 8.3Hz, 1H), 7.45-7.38 (m, 3H), 7.28 (td, J = 7.9, 5.9 Hz, 1H), 7.16 (d, J = 8.1Hz, 2H), 7.08 (d, J = 7.8Hz, 1H), 7.03-7.00 (m, 1H), 6.96-6.91 (m, 1H), 5.16 (dd, J = 6.2, 9.7Hz, 1H), 4.55 (s, 2H), 3.60 (dd, J = 8.1, 10.8Hz, 1H), 2.85-2.70 (m, 1H), 1.85-1.77 (m, 1H) 1.60 (d, J = 5.1Hz, 6H).<br>Tartrate salt, Elute with 50% methanol/propan-2-amine in supercritical carbon dioxide, retention time 0.51 min. | Yield 63% |
| 59 | 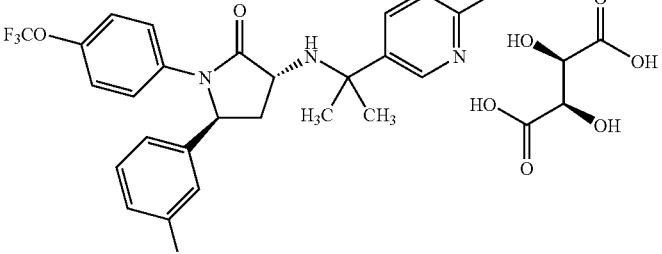<br>(3R,5S)-3-[1-Methyl-1-(6-chloro-pyridin-3-yl)-ethylamino]-5-(3 fluoro-phenyl)-1-(4-trifluoromethoxy-phenyl)-pyrrolidin-2-one L-tartrate<br>$^1$H NMR (400.13 MHz, MeOD): δ 8.43 (d, J = 2.2Hz, 1H), 7.94 (dd, J = 2.7, 8.6Hz, 1H), 7.55-7.51 (m, 2H), 7.30 (d, J = 8.3Hz, 1H), 7.19 (td, J = 7.9, 6.0 Hz, 1H), 7.10 (d, J = 8.6Hz, 2H), 6.87-6.79 (m, 3H), 5.31-5.29 (m, 1H), 4.42 (s, 2H), 3.50 (dd, J = 8.1, 10.0 Hz, 1H), 2.33 (dt, J = 13.2, 9.2Hz, 1H), 2.05 (ddd, J = 12.7, 8.1, 1.7Hz, 1H), 1.43 (d, J = 1.7Hz, 6H).<br>Tartrate salt, Elute with 50% methanol/propan-2-amine in supereritical carbon dioxide, retention time 1.67 min. | Yield 10% |
| 60 | 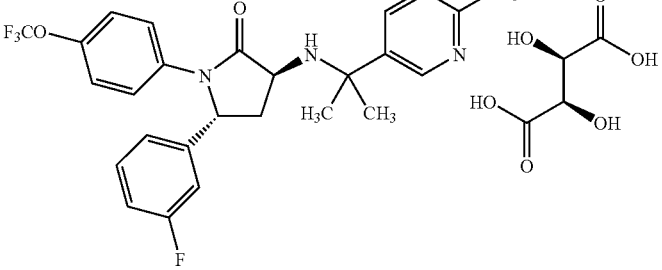<br>(3S,5R)-3-[1-methyl-1-(6-trifluoromethyl-pyridin-3-yl)-ethylamino]-5-(3-fluoro-phenyl)-1-(4-trifluoromethoxy-phenyl)-pyrrolidin-2-one L-tartrate<br>$^1$H NMR (400.13 MHz, MeOD): δ 8.94 (d, J = 2.0 Hz, 1H), 8.26 (dd, J = 2.0, 8.1Hz, 1H), 7.77 (d, J = 8.3Hz, 1H), 7.65-7.62 (m, 2H), 7.30 (td, J = 7.9, 6.0 Hz, 1H), 7.22 (d, J = 8.6Hz, 2H), 6.98-6.92 (m, 3H), 5.43-5.41 (m, 1H), 4.55 (s, 2H), 3.64 (dd, J = 7.9, 9.7Hz, 1H), 2.47 (dt, J = 12.7, 9.3Hz, 1H), 2.17 (ddd, J = 12.7, 8.1, 1.7Hz, 1H), 1.59 (d, J = 9.8Hz, 6H).<br>Tartrate salt, Elute with 10% methanol/propan-2-amine in supercritical carbon dioxide, retention time 0.66 min. | Yield 14.7% staring material: (R) lactam |

TABLE 14-continued

| Ex. N° | Compound, Name, Physical Data | Yield Comments |
|---|---|---|
| 61 | 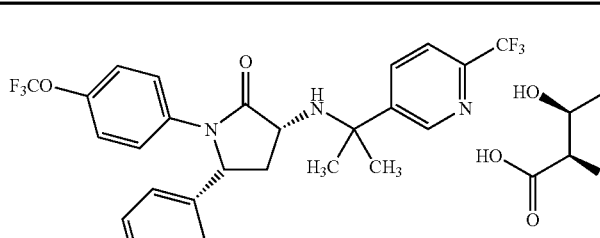<br>(3R, 5R) 3-[1-methyl-1-(6-trifluoromethyl-pyridin-3-yl)-ethylamino]-5-(3-fluoro-phenyl)-1-(4-trifluoromethoxy-phenyl)-pyrrolidin-2-one L-tartrate<br>$^1$H NMR (400.13 MHz, MeOD): δ 8.97 (d, J = 2.0 Hz, 1H), 8.32 (dd, J = 2.0, 8.3Hz, 1H), 7.80 (d, J = 8.3Hz, 1H), 7.42-7.38 (m, 2H), 7.28 (td, J = 7.9, 5.9Hz, 1H), 7.16 (d, J = 8.3Hz, 2H), 7.08 (d, J = 7.6Hz, 1H), 7.03-7.00 (m, 1H), 6.96-6.91 (m, 1H), 5.16 (dd, J = 6.4, 9.5Hz, 1H), 4.55 (s, 2H), 3.59 (dd, J = 8.2, 10.6Hz, 1H), 2.79-2.72 (m, 1H), 1.83 (dt, J = 12.2, 10.4Hz, 1H), 1.64 (d, J = 10.8Hz, 6H).<br>Tartrate salt, Elute with 10% methanol/propan-2-amine in supereritical carbon dioxide, retention time 0.96 min. | Yield 53.5%<br>Staring material:<br>(R) lactam |

EXAMPLE 62

(3R,5R)-3-[1'-Methyl-1-(6-trifluoromethyl-pyridin-3-yl)-ethylamino]-5-(3-trifluoromethoxy-phenyl)-1-(4-cyclopropyl-phenyl)-pyrrolidin-2-one

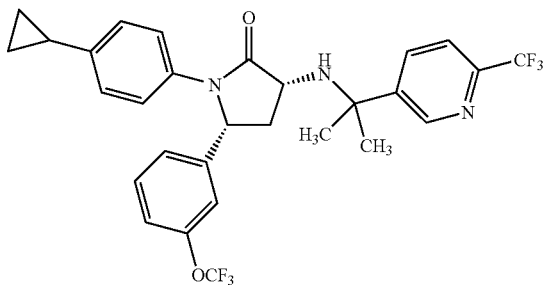

Dissolve (3R,5R)-3-[1-methyl-1-(6-trifluoromethyl-pyridin-3-yl)-ethylamino]-1-(4-bromo-phenyl)-5-(3-trifluoromethoxy-phenyl)-pyrrolidin-2-one (1.25 mmoles; 750 mg), cyclopropylboronic acid (1.62 mmoles; 139 mg), tribasic potassium phosphate N-hydrate (4.36 mmoles; 925 mg), and tricyclohexylphosphine (124.51 μmoles; 34 mg) in toluene (5 mL) and water (275 μL) and degas the solution for 5 minutes then place under a nitrogen atmosphere. Add Pd(OAc)$_2$ (62 μmoles; 14 mg) and heat the mixture at 90° C. overnight. Dilute with ethyl acetate (50 mL) and filter through celite. Wash the filtrate with water, 1N HCl, saturated aqueous sodium bicarbonate, brine, dry over anhydrous sodium sulfate, filter, and concentrate in vacuo to a brown residue. Purify the residue by flash chromatography on silica with gradient 0->50% ethyl acetate in hexane to afford the title compound (3R,5R)-3-[1-methyl-1-(6-trifluoromethyl-pyridin-3-yl)-ethylamino]-5-(3-trifluoromethoxy-phenyl)-1-(4-cyclopropyl-phenyl)-pyrrolidin-2-one (1.13 mmoles; 639.00 mg; 91.07% yield). LC/MS m/z 564.2 (M+1), Tr=4.87 min (Method 3).

CB$_1$ and CB$_2$ In Vitro Functional Assays

Antibody-Capture SPA GTP-γ-$^{35}$S Binding

Test exemplified compounds. Measure GTP-γ$^{35}$S binding in a 96 well format using a modified antibody capture technique previously described (DeLapp et al. 1999). Briefly incubate, CHO or Sf9 cell membranes expressing CB$_1$ or CB$_2$, respectively (Applied Cell Sciences, Gaithersburg, Md.; PerkinElmer Life Sciences, Boston, Mass.); prepare as previously described (DeLapp et al., 1999), exemplified compounds and 500 μM GTP-γ-$^{35}$S (PerkinElmer Life Sciences, Boston, Mass.) for 30 minutes (incubate all at room temperature) in GTP-binding assay buffer (20 mM Hepes, 100 mM NaCl, 5 mM MgCl$_2$, pH 7.4). Perform antagonist dose responses in the presence of a saturating dose of full agonist (methanandamide). Add a mixture containing 0.27% Nonidet P40 detergent (Roche, Indianapolis, Ind.), anti-Gi antibody (final dilution of 1:300; Covance, Princeton, N.J.), and 1.25 mg anti-rabbit antibody scintillation proximity assay beads (GE Healthcare, Piscataway, N.J.) and seal the plates and incubate for an additional 3 hours. Centrifuge the plates at 700×g for 10 minutes using a Beckman GS-6R centrifuge and count for 1 minute per well using a Wallac MicroBeta TriLux scintillation counter (PerkinElmer, Boston, Mass.).

To analyze data, first subtract background from all wells. Determine percent agonist efficacy by normalizing agonist/inverse agonist dose response data to a full agonist (methanandamide) response. Calculating antagonist percent inhibition data by normalizing to results generated with a saturating concentration of methanandamide. Analyze the data using a 4-parameter logistic reduced fit with Activity Base and XLFit3 (IDBS, Emeryville, Calif.). Determine K$_b$ values using a modification of the Cheng-Prusoff relationship: K$_b$=IC50/(1+[agonist]/EC50) where IC50 is determined from a four parameter fit of displacement curves, [agonist]= EC50 of full agonist, and EC50 is determined from a four parameter fit of a full agonist concentration response curve (Cheng and Prusoff 1973). Calculate mean K$_b$ values as a mean of at least three independent determinations±standard error of the mean (SEM).

Table 15 summarizes the antagonist/inverse agonist properties of Example 49 in CHO cells expressing human or rat $CB_1$ receptors or Sf9 cells expressing human $CB_2$ receptors. The data indicate that Example 49 is a potent $CB_1$ antagonist/inverse agonist at both rat and human receptors with low antagonism of human $CB_2$ receptors. Example 49 (Table 16) is an inverse agonist at the human $CB_1$ receptor as evidenced by agonist efficacy less than zero which indicates that the compound decreased basal constitutive activity of the $CB_1$ receptor in vitro.

The exemplified compounds (Table 17) exhibit potent human and rat $CB_1$ antagonism/inverse agonism with only low affinity antagonism/inverse agonism of the human $CB_2$ receptor.

Exemplified compounds of this invention are potent $CB_1$ antagonist/inverse agonist at both rat and human receptors with low antagonism of human $CB_2$ receptors. Exemplified compounds of this invention are inverse agonist at the human $CB_1$ receptor as evidenced by agonist efficacy less than zero which indicates that the compound decreased basal constitutive activity of the $CB_1$ receptor in vitro.

REFERENCES

DeLapp N W, McKinzie J H, Sawyer B D, Vandergriff A, Falcone J, McClure D and Felder C C (1999). Determination of [$^{35}$S]guanosine-5'-O-(3-thio)triphosphate binding mediated by cholinergic muscarinic receptors in membranes from Chinese hamster ovary cells and rat striatum using an anti-G protein scintillation proximity assay. *J Pharmacol Exp Ther* 289:946-955.

Cheng Y C and Prusoff W H. 1973. Relationship between the inhibition constant (Ki) and the concentration of inhibitor which causes 50 percent inhibition (I50) of an enzymatic reaction. Biochem Pharmacol 22:3099-3108.

TABLE 15

In Vitro $CB_1$ and $CB_2$ Antagonist/Inverse Agonist Functional GTP-Binding for Example 49 in CHO or Sf9 Cell Membranes Expressing Human and Rat Cannabinoid Receptors

| GTP Binding Assay (CHO or Sf9 cell membranes) | Inverse Agonist Potency [$K_b$ (nM)] |
|---|---|
| Human $CB_1$ (CHO cells) | 0.226 ± 0.01 |
| Rat $CB_1$ (CHO cells) | 0.264 ± 0.02 |
| Human $CB_2$ (Sf9 cells) | 587 ± 191 |

TABLE 16

In Vitro $CB_1$ and $CB_2$ Agonist GTP-Binding for Example 49 in Cell Membranes from Sf9 Cells Expressing Human Receptors

| GTP Binding Assay (Sf9 membranes) | Agonist Potency $EC_{50}$ (nM) | Agonist Efficacy % |
|---|---|---|
| Human $CB_1$ | 0.81 ± 0.19 | −38.3 ± 1.0 |
| Human $CB_2$ | >10000 | 0 |

Force Swim Test (FST)

Receive NIH male Swiss mice (Harlan Sprague-Dawley, weigh 20-25 g) 7-10 days prior to testing. House 12 mice/cage. Test animals that weigh 25-30 g. On the day of test, bring animals to the testing room at least 1 hr prior to dosing, when doing starts, 6-8 min. intervals between each dosing with mouse receiving either vehicle or exemplified compounds by p.o., and then put it into a clean cage afterwards (4 mice/cage). Depending on pretreatment time, start the test accordingly.

Mice FST: Place NIH-Swiss mice in clear plastic cylinders (diameter: 10 cm; height: 25 cm) filled to 6 cm with 22-25° C. water for six min. Record the duration of immobility during the last 4 min. of the six-minute trial. A mouse is regarded as immobile when floating motionless or making only those movements necessary to keep its head above the water.

Copy the data-immobility (second) into JMP data sheet, and analyze by ANOVA-Dunnett's test. Record the minimum effective dose (MED) as the lowest dose of compound at which statistically significant decrease in immobility time is observed versus a vehicle control.

Bioavailabilty

Methods for accessing bioavailabilty are well appreciated in the art. One such reference is Medicinal Research Reviews Vol 21 No. 5 382-396 (2001).

The exemplified compounds in Table 17 have the following biological data.

TABLE 17

| | Antibody-Capture SPA GTP-γ-$^{35}$S Binding Inverse AgonistPotency | | | | |
|---|---|---|---|---|---|
| Example No.: | $CB_1$ ($K_b$, nM)* | $CB_2$ ($K_b$, nM) | Bioavail. Rat | Bioavail. Dog | Forced Swim Test (MED, mg/kg, po) |
| Example 1 | 0.91 | 390 | 7% | 36% | Not Determined |
| Example 32B | 2.38 | >4000 | Not Determined | Not Determined | Not Determined |
| Example 40 | 0.71 | >6900 | 77% | 38% | Not Determined |
| Example 41 | 0.91 | >14200 | 36% | 47% | Not Determined |
| Example 4 | 107 | >7230 | Not Determined | Not Determined | Not Determined |
| Example 44 | 72.7 | 4030 | Not Determined | Not Determined | Not Determined |
| Example 49 | 2.6 | 587 | 36% | 40% | 3 |

*h$CB_1$ SPA GTPγ$^{35}$S Sf9 Mem 22.7 ug protein/well Antagonist

We claim:
1. The compound of the Formula

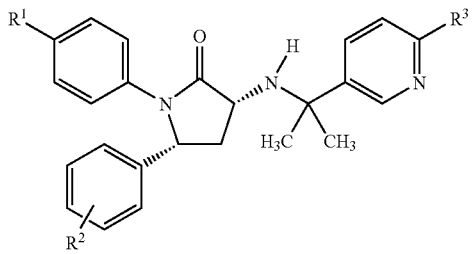

wherein:
R¹ is selected from the group consisting of:
  a) —OCF₃ and
  b) —CF₃;
R² is one or two substituents independently selected from the group consisting of:
  a) —H,
  b) halo,
  c) —CF₃,
  d) methyl, ethyl, and isopropyl; and
  e) —CN;
R³ is selected from the group consisting of:
  a) —CF₃,
  b) -cyclopropyl, and
  c) halo;
or a pharmaceutically acceptable salt thereof.

2. A pharmaceutical composition comprising a compound according to claim 1, or a pharmaceutically acceptable salt thereof, and a pharmaceutically acceptable carrier, diluent, or excipient.

3. The compound according to claim 1 which is (3R,5R)-3-[1-methyl-1-(6-trifluoromethyl-pyridin-3-yl)-ethylamino]-5-phenyl-1-(4-trifluoromethoxy-phenyl)-pyrrolidin-2-one or a pharmaceutically acceptable salt thereof.

* * * * *